United States Patent
Pattaropong et al.

(10) Patent No.: US 11,807,624 B2
(45) Date of Patent: Nov. 7, 2023

(54) SUBSTITUTED PYRIMIDINONES AS AGONISTS OF THE APJ RECEPTOR

(71) Applicant: AMGEN INC., Thousand Oaks, CA (US)

(72) Inventors: Vatee Pattaropong, Bedford, MA (US); Philip Dean Ramsden, Acton, MA (US)

(73) Assignee: Amgen Inc., Thousand Oaks, CA (US)

( * ) Notice: Subject to any disclaimer, the term of this patent is extended or adjusted under 35 U.S.C. 154(b) by 275 days.

(21) Appl. No.: 17/051,212

(22) PCT Filed: Apr. 30, 2019

(86) PCT No.: PCT/US2019/029780
§ 371 (c)(1),
(2) Date: Oct. 28, 2020

(87) PCT Pub. No.: WO2019/213006
PCT Pub. Date: Nov. 7, 2019

(65) Prior Publication Data
US 2021/0246118 A1    Aug. 12, 2021

Related U.S. Application Data

(60) Provisional application No. 62/665,244, filed on May 1, 2018.

(51) Int. Cl.
| C07D 239/545 | (2006.01) |
| C07D 401/12 | (2006.01) |
| C07D 401/14 | (2006.01) |
| C07D 403/12 | (2006.01) |
| C07D 405/14 | (2006.01) |

(52) U.S. Cl.
CPC ....... *C07D 401/14* (2013.01); *C07D 239/545* (2013.01); *C07D 401/12* (2013.01); *C07D 403/12* (2013.01); *C07D 405/14* (2013.01)

(58) Field of Classification Search
CPC .......... C07D 239/545; C07D 401/12; C07D 401/14; C07D 403/12; C07D 405/14
See application file for complete search history.

(56) References Cited

U.S. PATENT DOCUMENTS

| 4,844,730 A | 7/1989 | Moriya et al. |
| 4,941,912 A | 7/1990 | Kirsten et al. |
| 5,302,718 A | 4/1994 | Agback et al. |
| 5,328,803 A | 7/1994 | Fukijura et al. |
| 5,342,741 A | 8/1994 | Morimoto et al. |
| 5,411,839 A | 5/1995 | Harder et al. |
| 5,451,588 A | 9/1995 | Baker et al. |
| 5,510,362 A | 4/1996 | Matassa et al. |
| 5,563,026 A | 10/1996 | Singer |
| 5,910,504 A | 6/1999 | Hutchinson |
| 6,069,141 A | 5/2000 | Barbachyn et al. |
| 6,194,090 B1 | 2/2001 | Okada |
| 6,555,693 B2 | 4/2003 | Ge et al. |
| 6,586,423 B2 | 7/2003 | Bilodeau et al. |
| 6,727,364 B2 | 4/2004 | Tullis et al. |
| 6,787,555 B2 | 9/2004 | Tullis et al. |
| 6,790,846 B2 | 9/2004 | Clark et al. |
| 7,084,145 B2 | 8/2006 | Armour et al. |
| 7,084,164 B2 | 8/2006 | Tobe et al. |
| 7,169,797 B2 | 1/2007 | Xin et al. |
| 7,297,168 B2 | 11/2007 | Murphy et al. |
| 7,361,669 B2 | 4/2008 | Scarborough et al. |

(Continued)

FOREIGN PATENT DOCUMENTS

| AU | 199886243 B2 | 4/1999 |
| AU | 2012200157 A1 | 9/2012 |

(Continued)

OTHER PUBLICATIONS

Berry, M. F. et al., "Apelin Has In Vivo Inotropic Effects on Normal and Failing Hearts," Circulation 100, pp. II187-II193, (2004).

(Continued)

*Primary Examiner* — Brian E McDowell
(74) *Attorney, Agent, or Firm* — Glenn J. Foulds; Fenwick & West LLP

(57) ABSTRACT

Compounds of Formula I and Formula II, pharmaceutically acceptable salts thereof, stereoisomers of any of the foregoing, or mixtures thereof are agonists of the APJ Receptor and may have use in treating cardiovascular and other conditions. Compounds of Formula I and Formula II have the following structures: Figure I and Figure II where the definitions of the variables are provided herein.

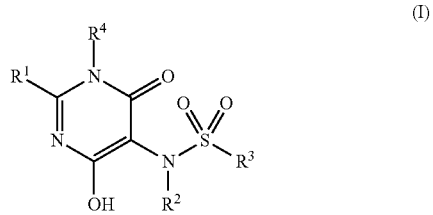

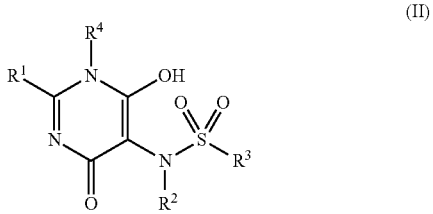

35 Claims, 3 Drawing Sheets

(56) References Cited

U.S. PATENT DOCUMENTS

| | | |
|---|---|---|
| 7,371,757 B2 | 5/2008 | Morningstar et al. |
| 7,615,569 B2 | 11/2009 | Fulp et al. |
| 7,635,751 B2 | 12/2009 | Kitada et al. |
| 7,638,541 B2 | 12/2009 | Chen et al. |
| 7,718,683 B2 | 5/2010 | Charvat et al. |
| 7,776,897 B2 | 8/2010 | Murakami et al. |
| 7,820,665 B2 | 10/2010 | Booker et al. |
| 8,034,834 B2 | 10/2011 | Du et al. |
| 8,053,456 B2 | 11/2011 | Sun et al. |
| 8,063,083 B2 | 11/2011 | Foley |
| 8,076,486 B2 | 12/2011 | Goutopoulos et al. |
| 8,101,618 B2 | 1/2012 | Kawamoto et al. |
| 8,252,822 B2 | 8/2012 | An et al. |
| 8,299,107 B2 | 10/2012 | Chimmanamada et al. |
| 8,318,790 B2 | 11/2012 | Ying et al. |
| 8,399,464 B2 | 3/2013 | Kuramochi et al. |
| 8,415,377 B2 | 4/2013 | Sun et al. |
| 8,426,602 B2 | 4/2013 | Meibom et al. |
| 8,431,604 B2 | 4/2013 | Netz et al. |
| 8,445,518 B2 | 5/2013 | Charvat et al. |
| 8,466,170 B2 | 6/2013 | Klein |
| 8,492,427 B2 | 7/2013 | Gancia et al. |
| 8,563,741 B2 | 10/2013 | Qian et al. |
| 8,648,104 B2 | 2/2014 | Du et al. |
| 8,673,848 B2 | 3/2014 | Zecri et al. |
| 8,742,133 B2 | 6/2014 | Ying et al. |
| 8,778,977 B2 | 7/2014 | Lind et al. |
| 8,835,464 B2 | 9/2014 | Sun et al. |
| 8,883,827 B2 | 11/2014 | Holsworth et al. |
| 9,156,796 B2 | 10/2015 | Hachtel et al. |
| 9,573,936 B2 | 2/2017 | Chen et al. |
| 9,656,997 B2 | 5/2017 | Chen et al. |
| 9,656,998 B2 | 5/2017 | Chen et al. |
| 9,745,286 B2 | 8/2017 | Chen et al. |
| 9,751,864 B2 | 9/2017 | Chen et al. |
| 9,845,310 B2 | 12/2017 | Chen et al. |
| 9,868,721 B2 | 1/2018 | Chen et al. |
| 9,988,369 B2 | 6/2018 | Chen et al. |
| 10,058,550 B2 | 8/2018 | Chen et al. |
| 10,100,059 B2 | 10/2018 | Runyon et al. |
| 10,150,760 B2 | 12/2018 | Chen et al. |
| 10,221,162 B2 | 3/2019 | Chen et al. |
| 10,344,016 B2 | 7/2019 | Dransfield et al. |
| 10,689,367 B2 | 6/2020 | Chen et al. |
| 10,736,883 B2 | 8/2020 | Brown et al. |
| 10,906,890 B2 | 2/2021 | Chen et al. |
| 11,020,395 B2 | 6/2021 | Chen et al. |
| 11,046,680 B1 | 6/2021 | Chen et al. |
| 2002/0107245 A1 | 8/2002 | Wagle et al. |
| 2003/0158238 A1 | 8/2003 | Hale et al. |
| 2004/0167188 A1 | 8/2004 | Xin et al. |
| 2005/0075275 A1 | 4/2005 | Albrecht et al. |
| 2005/0165015 A1 | 7/2005 | Ncube |
| 2005/0170431 A1 | 8/2005 | Ibrahim et al. |
| 2005/0288347 A1 | 12/2005 | Hodge et al. |
| 2006/0100235 A1 | 5/2006 | Andersen et al. |
| 2006/0156480 A1 | 7/2006 | Lim |
| 2006/0281749 A1 | 12/2006 | Wagle et al. |
| 2008/0153869 A1 | 6/2008 | Bressi et al. |
| 2008/0249131 A1 | 10/2008 | Girardet et al. |
| 2009/0318438 A1 | 12/2009 | Chen et al. |
| 2010/0130472 A1 | 5/2010 | Young et al. |
| 2010/0131472 A1 | 5/2010 | Zlotnick |
| 2010/0249185 A1 | 9/2010 | Du et al. |
| 2010/0280032 A1 | 11/2010 | Zhou et al. |
| 2011/0046125 A1 | 2/2011 | Ying |
| 2011/0158940 A1 | 6/2011 | Byrd et al. |
| 2011/0190257 A1 | 8/2011 | Heald et al. |
| 2011/0207788 A1 | 8/2011 | Amberg et al. |
| 2011/0265691 A1 | 11/2011 | Orth et al. |
| 2012/0094837 A1 | 4/2012 | Muhlthau et al. |
| 2012/0208828 A1 | 8/2012 | Holsworth et al. |
| 2012/0238576 A1 | 9/2012 | Tao et al. |
| 2013/0034536 A1 | 2/2013 | Gedulin |
| 2013/0040950 A1 | 2/2013 | Short et al. |
| 2013/0059807 A1 | 3/2013 | Gedulin et al. |
| 2013/0059845 A1 | 3/2013 | Song et al. |
| 2013/0108573 A1 | 5/2013 | Gedulin et al. |
| 2013/0109671 A1 | 5/2013 | Gedulin et al. |
| 2013/0150385 A1 | 6/2013 | Blackman et al. |
| 2013/0156755 A1 | 6/2013 | Blackman et al. |
| 2013/0266636 A1 | 10/2013 | Cheresh et al. |
| 2013/0303505 A1 | 11/2013 | Bollu et al. |
| 2014/0005181 A1 | 1/2014 | Smith et al. |
| 2014/0031374 A1 | 1/2014 | Holsworth et al. |
| 2016/0058705 A1 | 3/2016 | Rajadas et al. |
| 2016/0060349 A1 | 3/2016 | Van Schravendijk et al. |
| 2016/0340336 A1 | 11/2016 | Chen et al. |
| 2016/0355507 A1 | 12/2016 | Johnsen et al. |
| 2017/0035744 A1 | 2/2017 | Chen et al. |
| 2017/0037026 A1 | 2/2017 | Chen et al. |
| 2017/0042871 A1 | 2/2017 | Chen et al. |
| 2017/0042872 A1 | 2/2017 | Chen et al. |
| 2017/0042897 A1 | 2/2017 | Chen et al. |
| 2017/0044131 A1 | 2/2017 | Chen et al. |
| 2017/0281625 A1 | 10/2017 | Chen et al. |
| 2017/0320860 A1 | 11/2017 | Chen et al. |
| 2017/0355734 A1 | 12/2017 | Llorens-Cortez et al. |
| 2018/0118698 A1 | 5/2018 | Smith et al. |
| 2018/0282289 A1 | 10/2018 | Ikeda et al. |
| 2019/0100510 A1 | 4/2019 | Dransfield et al. |
| 2019/0275008 A1 | 9/2019 | Brown et al. |
| 2019/0284173 A1 | 9/2019 | Chen et al. |
| 2019/0290647 A1 | 9/2019 | Chen et al. |
| 2019/0290648 A1 | 9/2019 | Chen et al. |
| 2020/0308189 A1 | 10/2020 | Dransfield et al. |

FOREIGN PATENT DOCUMENTS

| | | |
|---|---|---|
| DE | 3928605 A1 | 3/1991 |
| DE | 4035141 A1 | 5/1992 |
| EP | 0121082 B1 | 10/1984 |
| EP | 0330959 A2 | 2/1989 |
| EP | 0419831 A2 | 8/1989 |
| EP | 0359505 A1 | 3/1990 |
| EP | 0409332 A2 | 1/1991 |
| EP | 0484750 A1 | 10/1991 |
| EP | 0580041 B1 | 10/2000 |
| IT | 1404729 B1 | 11/2013 |
| JP | 03172939 A | 7/1991 |
| JP | 06148841 A | 5/1994 |
| JP | 2003-5356 A | 8/2003 |
| JP | 2003-321456 A | 11/2003 |
| JP | 2005-170939 A | 6/2005 |
| WO | 91/11909 A1 | 8/1991 |
| WO | 99/43671 A1 | 9/1999 |
| WO | WO 99/46371 A2 | 9/1999 |
| WO | 01/87855 A1 | 11/2001 |
| WO | 2005/039569 A1 | 5/2005 |
| WO | 2006/026488 A1 | 3/2006 |
| WO | 2006/055760 A1 | 5/2006 |
| WO | 2006/080533 A1 | 8/2006 |
| WO | 2006/095783 A1 | 9/2006 |
| WO | 2006/100588 A1 | 9/2006 |
| WO | 2006/109817 A1 | 10/2006 |
| WO | 2007/007688 A1 | 1/2007 |
| WO | 2007/139952 A2 | 12/2007 |
| WO | 2007/139967 A2 | 12/2007 |
| WO | 2008/008375 A2 | 1/2008 |
| WO | 2008/021364 A2 | 2/2008 |
| WO | 2008/103352 A1 | 8/2008 |
| WO | 2009/075890 A2 | 6/2009 |
| WO | 2009/115503 A1 | 9/2009 |
| WO | 2010/017545 A2 | 2/2010 |
| WO | 2011/146801 A1 | 11/2011 |
| WO | 2012/076898 A1 | 6/2012 |
| WO | 2012/116247 A1 | 8/2012 |
| WO | 2013/067162 A1 | 5/2013 |
| WO | 2013/067165 A1 | 5/2013 |
| WO | 2013/074594 A1 | 5/2013 |
| WO | 2013/106437 A1 | 7/2013 |
| WO | 2013/106614 A1 | 7/2013 |
| WO | 2013/111110 A2 | 8/2013 |
| WO | 2013/148857 A1 | 10/2013 |

(56) References Cited

FOREIGN PATENT DOCUMENTS

| WO | 2013/184755 A2 | 12/2013 |
|---|---|---|
| WO | 2014/044738 A1 | 3/2014 |
| WO | 2014/099984 A1 | 6/2014 |
| WO | 2014/150326 A1 | 9/2014 |
| WO | 2014/194270 A1 | 12/2014 |
| WO | 2015/140296 A2 | 9/2015 |
| WO | 2015/163818 A1 | 10/2015 |
| WO | 2015/184011 A2 | 12/2015 |
| WO | 2015/188073 A1 | 12/2015 |
| WO | 2016/151018 A1 | 9/2016 |
| WO | 2016/187308 A1 | 11/2016 |
| WO | 2016/196771 A1 | 12/2016 |
| WO | 2017/066402 A1 | 4/2017 |
| WO | 2017/091513 A1 | 6/2017 |
| WO | 2017/096130 A1 | 6/2017 |
| WO | 2017/100558 A1 | 6/2017 |
| WO | 2017/106396 A1 | 6/2017 |
| WO | 2017/165640 A1 | 9/2017 |
| WO | 2017/174758 A1 | 10/2017 |
| WO | 2017/192485 A1 | 11/2017 |
| WO | 2017/218617 A1 | 12/2017 |
| WO | 2017/218633 A1 | 12/2017 |
| WO | 2018/071526 A1 | 4/2018 |
| WO | 2018/071622 A1 | 4/2018 |
| WO | WO 2018/074526 A1 | 4/2018 |
| WO | 2018/093576 A1 | 5/2018 |
| WO | 2018/093577 A1 | 5/2018 |
| WO | 2018/093579 A1 | 5/2018 |
| WO | 2018/095380 A1 | 5/2018 |
| WO | 2018/097944 A1 | 5/2018 |
| WO | 2018/097945 A1 | 5/2018 |
| WO | 2019/089335 A1 | 5/2019 |
| WO | WO 2019/169193 A1 | 9/2019 |
| WO | WO 2019/213006 A1 | 11/2019 |

OTHER PUBLICATIONS

Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett. 6b00038; lccn:2009200243; oclcnum:455500725; serissn:1948-5875; itc:84454717; itcp:10547084 (2016).

Chun, H. et al., "Apelin Signaling Antagonizes ANG II Effects in Mouse Models of Atherosclerosis," J. Clin. Invest. 118(10), pp. 3343-3354 (2008).

Japp, A. G. et al., "Acute Cardiovascular Effects of Apelin in Humans," Circulation 121, pp. 1818-1827 (2010).

Modzelewska-Banachiewicz et al., "Synthesis and Biological Action of 3-4-Disubstituted 5-Arylsulphonylamino-1,2,4-triazoles," Pharmazie 54, pp. 588-589 (1999).

Pauli, A. et al., "Toddler: An Embryonic Signal That Promotes Cell Movement via Apelin Receptors," Science 343, pp. 1248636-0-1248636-8 (2014).

Siddiquee, K. et al., "The Apelin receptor Inhibits the Angiotensin II Type 1 Receptor via Allosteric Trans-Inhibition," Br. J. Pharmacol. 168, pp. 1104-1117 (2013).

Siddiquee, K. et al., "Apelin Protects Against Angiotension II-Induced Cardiovascular Fibrosis and Decreases Plasminogen Activator Inhibitor Type-1 Production," J. Hypertension 29, pp. 724-731 (2011).

Tatemoto, K. et al., "Isolation and Characterization of a Novel Endogenous Peptide Ligand for the Human APJ Receptor," Bioch. Biophys. Res. Comm., 251, pp. 471-476 (1998).

Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).

Maguire, J. J. et al., "[Pyr$^1$]Apelin-13 Identified as the Predominant Apelin Isoform in the Human Heart: Vasoactive Mechanism and Inotropic Action in Disease," Hypertension 54(3), pp. 598-604, (2009).

Barnes, G. et al., "Translational Promise of the Apelin-APJ System," Heart 96(13), pp. 1011-1016 (2010).

Kawamata, Y. et al., "Molecular Properties of Apelin: Tissue Distribution and Receptor Binding," Biochemica et Biophysica Acta 1538(2-3), pp. 162-171 (2001).

Nishizawa, N. et al., "High Potency Analog of Apelin, A Ligand of Orphan GPCT APJ," T Shiori (ed.) Peptide Science 2000: Proceedings of the 37$^{th}$ Japanese Peptide Symposium, pp. 151-154 (2000).

Medhurst, A. D. et al., "Pharmacological and Immunohistochemical Characteization of the APJ Receptor and its Endogenous Ligand Apelin," J. Neurochem. 84(5), pp. 1162-1172 (2003).

Hamada, J. et al., "Evaluation of Noval Cyclic Analogoues of Apelin," Int. J. Mol. Med. 22, pp. 547-552 (2008).

Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).

Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).

Thomas, J.B. et al., "Identification of N-[5-{[(4-Methylphenyl)sulfonyl]amino}-3-(trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).

Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett. 25, pp. 2060-2064 (2015).

Thompson, M. E. "α,N-Alkanesulfonamide Dianions: Formation and Chemoselective C-Alkylation," J. Org. Chem. 49, pp. 1700-1703 (1984).

Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).

Singh, O. M. et al., "A Facile One-Pot Synthetic Method for 1,2,4-Triazoles and 1,3-Disubstituted Thioureas," J. Chem. Res. pp. 483-485 (2006).

Carlsen, P.J.J. et al., "Synthesis of Unsymmetrically Substituted 4H-1,2,4-Triazoles," J. Heterocyclic Chem. 31, pp. 805-807 (1994).

Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).

Hassan, A. A. et al., "Thiosemicarbazides in Heterocyclization," J. Heterocyclic Chem. 48, pp. 495-516 (2011).

Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).

Ivanova, N. V. et al., "A Convenient Synthesis of 4,5-Disubstituted 1,2,4-Triazoles Functionalized in Position 3," Synthesis 1, pp. 156-160 (2005).

Modzelewska-Banaschiewicz, B et al., "Antiviral Activity of the Products of Cyclization of Dimethyl 2-[1-arylamino-1-arylmethylideine)hydrazono]succinate," Eur. J. Med. Chem. 36, pp. 93-99 (2001).

Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).

Johnson, M. G. et al., "Convenient Route to Secondary Sulfinates: Application to the Stereospecific Synthesis of α-C-Chiral Sulfonamides," Organic Letters 16(23), pp. 6248-6251 (2014).

Enders, D. et al., "Asymmetric Synthesis of α-Substituted N-Methylsulfonamides," Helvetica Chimica Acta, 85, pp. 3657-3677 (2002).

Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).

(56) References Cited

OTHER PUBLICATIONS

Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).
Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).
International Search Report and Written Opinion for analogous PCT Application No. PCT/US2019/029780 dated Jun. 24, 2019.
Kuo, C.-L. et al., "Application of CoMFA and CoMSIA 3D-QSAR and Docking Studies in Optimization of Mercaptobenzenesulfonamides as HIV-1 Integrase Inhibitors," J. Med. Chem., 47(2), pp. 385-399 (2004).
SciFinder Structure Search 1with Substances Performed Jan. 9, 2018.
SciFinder Structure Search 1 with References Performed Jan. 1, 2018.
SciFinder Structure Search 2 with Substances Performed Jan. 9, 2018.
SciFinder Structure Search 2 with References Performed Jan. 9, 2018.
Shrimali, S.S. et al., "Studies on the Synthesis and Antimicrobial Properties of Aryl Barbitural Sulphones," J. Ind. Chem. Soc., pp. 424-440 (1988).
Kestner, M.M. et al., "Photographic Elements and Processes," Res. Disc., pp. 68-74 1976.
El-Zanfally, S. et al., "Attempted Preparation of 5-Saccharinobarbituric Acid," United Arab Republic Journal of Chemistry, pp. 99-102 (1970).
Dymek, W. et al., "Pyrimidine Derivatives", Acto Poloniae Pharmaceutica, pp. 199-204 (1970). Article is in Polish, but an English language abstract is attached.
Ganapathi, K. "Chemotherapy of Bacterial Infections," Proceedings Ind. Acad. Sci. Section A, pp. 386-389 (1941).
Pecorari, P. et al., "Antimycotic Action of Some N-(5-pyrimidinyl)benzenesulfonamides," Farmaco Edizione Scientifica, pp. 696-701 (1984).
Horig, H. et al., "From bench to clinic and back: Perspective on the 1st IQPC Translational Research conference," Journal of Translational Medicine 2(44), Dec. 2004, p. 1-8.
International Search Report and Written Opinion for analogous PCT Application No. PCT/US2016/033088, dated Aug. 24, 2016.
International Search Report and Written Opinion for analogous PCT Application No. PCT/US2017/030501, dated Jul. 31, 2017.
International Search Report and Written Opinion for analogous PCT Application No. PCT/US2017/059822, dated May 3, 2018.
International Search Report and Written Opinion for analogous PCT Application No. PCT/US2017/059824, dated May 3, 2018.
International Search Report and Written Opinion for analogous PCT Application No. PCT/US2017/059828, dated Mar. 26, 2018.
International Search Report and Written Opinion for analogous PCT Application No. PCT/US2017/059830, dated Mar. 2018.
International Search Report and Written Opinion for analogous PCT Application No. PCT/US2018/057466 dated Jan. 23, 2019.
International Search Report for analogous PCT Application No. PCT/US2017/059834, dated Apr. 1, 2018.
International Search Report for analogous PCT Application No. PCT/US2017/059839, dated Apr. 1, 2018.
Neamati, N. et al., "2-Mercaptobenzenesulphonamides as Novel Inhibitors of Human Immunodeficiency virus Type 1 Integrase and Replication," Antiviral Chemistry and Chemotherapy, Dec. 1, 1997, pp. 485-495.
O'Carroll, A-M. et al., "The apelin receptor APJ: journey from an orphan to a multifaceted regulator of homeostasis," Journal of Endocrinology 219(1), Sep. 2013, pp. R13-R35.
Okawa, T. et al., "Design, Synthesis, and Evaluation of the Highly Selective and Potent G-Protein-Coupled Receptor Kinase 2 (GRK2) Inhibitor for the Potential Treatment of Heart Failure," J. Med. Chem. 60(16, Jul. 12, 2017, pp. 6942-6990.
Read, C. et al., "Cardiac action of the first G protein biased small molecule apelin agonist," Biochemical Pharmacology, vol. 116, Sep. 2016, pp. 63-72.
Registry No. 245090-92-0, File Registry on STN, Oct. 25, 1999.
Rydzewski, Real World Drug Discovery 2008, 42-43.
Satoh, M. et al., "Combined effect of blood pressure and total cholesterol levels on long-term risks of subtypes of cardiovascular death: Evidence for Cardiovascular Prevention from Observational Cohorts in Japan," Hypertension 65(3), Mar. 2015, pp. 517-524.
Schafer, S. et al., "Failure is an option: learning from unsuccessful proof-of-concept trials," Drug Discovery Today, vol. 13, Iss. 21-22, Nov. 2008, pp. 913-916.
SciFinder Intermediate Structure Search with References Performed May 6, 2016.
SciFinder Intermediate Structure Search with Substances Performed May 6, 2016.
SciFinder Structure Search 1 with References Performed Jun. 29, 2017.
SciFinder Structure Search 1 with Substances Performed Jun. 29, 2017.
SciFinder Structure Search 2 with References Performed Jun. 29, 2017.
SciFinder Structure Search 2 with Substances Performed Jun. 29, 2017.
SciFinder Structure Search Sulfonamide Tail with Substance Performed May 12, 2016.
SciFinder Structure Search with alkyl at top with References Performed Jun. 3, 2016.
SciFinder Structure Search with alkyl at top with Substances Performed Jun. 3, 2016.
SciFinder Structure Search with References Performed Jun. 3, 2016.
SciFinder Structure Search with References Performed May 20, 2016.
SciFinder Structure Search with References Performed May 3, 2016.
SciFinder Structure Search with References Performed Sep. 1, 2016.
SciFinder Structure Search with References Performed Sep. 2, 2016.
SciFinder Structure Search with References Performed Sep. 8, 2016.
SciFinder Structure Search with Substances Performed Jun. 3, 2016.
SciFinder Structure Search with Substances Performed May 20, 2016.
SciFinder Structure Search with Substances Performed May 3, 2016.
SciFinder Structure Search with Substances Performed Sep. 2, 2016.
SciFinder Structure Search with Substances Performed Sep. 8, 2016.
SciFinder Structure Search with Substances Performed Sep. 1, 2016.

hAPJ-hAT1R Stable Cell Line

✱ Ang II alone
○ +30nM pyr apelin-13
□ +100nM pyr apelin-13
▽ +300nM pyr apelin-13
△ +1uM pyr apelin-13
◇ +3uM pyr apelin-13

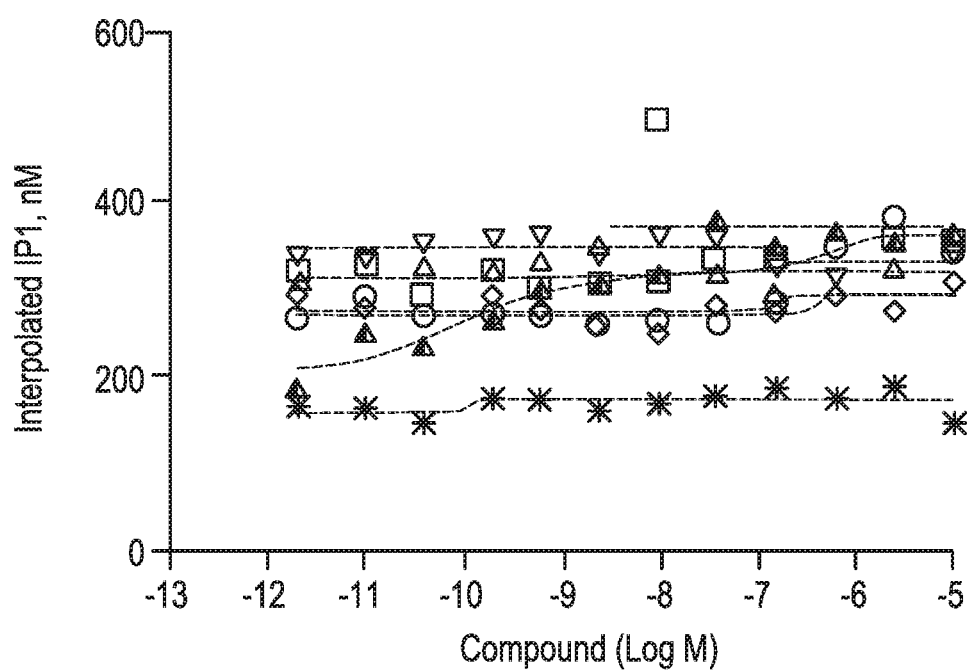

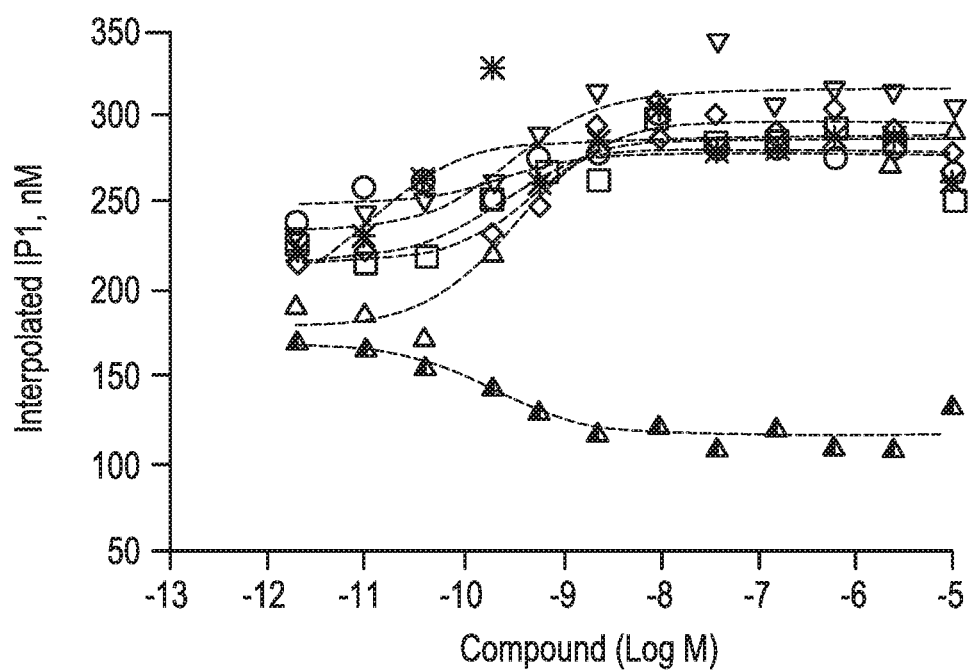

SUBSTITUTED PYRIMIDINONES AS AGONISTS OF THE APJ RECEPTOR

CROSS REFERENCES TO RELATED APPLICATIONS

This application claims the benefit of U.S. Provisional Application No. 62/665,244, filed on May 1, 2018, which is hereby incorporated by reference in its entirety and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to beat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77-also referred to as Apelin-36) and a smaller 13 residue polypeptide (Apelin 65-77-also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65] Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at sub-nanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275: 21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than apelin-13. Nishizawa et al., in: T. Shioiri (ed.), Peptide Science 2000: Proceedings of the $37^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule, but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. ChemMedChem 7:318-325, 2012. Additionally, PCT/US2013/075773 describes a group of modifications, including substitution of non-canonical amino acids and changes at the N- and C-terminal of the apelin molecule that can affect, inter alia, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor. Other small molecule agonists of the APJ receptor are disclosed in U.S. Pat. Appl. Pub. No. US 2016/0340336, WO 2016/187308, WO 2015/184011, WO 2015/188073, WO 2016/196771, WO 2017/192485, WO 2017/0066402, WO 2017/106396, WO 2017/165640, WO 2017/218617, and WO 2017/218633.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

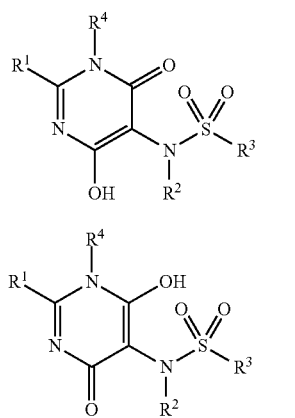

I

II or a pharmaceutically acceptable salt thereof, a tautomer thereof, a pharmaceutically acceptable salt of the tautomer, a stereoisomer of any of the foregoing, or a mixture thereof, wherein:

$R^1$ is selected from $R^{1a}$, $R^{1b}$, $R^{1c}$, $R^{1d}$, $R^{1e}$, $R^{1f}$, or $R^{1g}$;

$R^{1a}$ is an unsubstituted $C_1$-$C_8$ straight or branched chain alkyl or $R^{1a}$ is a $C_1$-$C_8$ straight or branched chain alkyl substituted with 1, 2, or 3 $R^{1a'}$ substituents;

$R^{1b}$ is an unsubstituted monocyclic $C_3$-$C_8$ cycloalkyl, an unsubstituted $C_5$-$C_8$ polycyclic cycloalkyl, an unsubstituted monocyclic $C_4$-$C_8$ cycloalkenyl, a monocyclic $C_3$-$C_8$ cycloalkyl substituted with 1, 2, 3, or 4 $R^{1b'}$ substituents, a $C_5$-$C_8$ polycyclic cycloalkyl substituted with 1, 2, or 3 $R^{1b'}$ substituents, or a monocyclic $C_4$-$C_8$ cycloalkenyl substituted with 1, 2, or 3 $R^{1b'}$ substituents;

$R^{1c}$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1c'}$ substituents;

$R^{1d}$ is a phenyl group that is unsubstituted or is substituted with 1, 2, or 3 $R^{1d'}$ substituents;

$R^{1e}$ is an unsubstituted furanyl, or is a furanyl substituted with 1, 2, or 3 $R^{1e'}$ substituents;

$R^{1f}$ is a 5- or 6-membered heteroaryl group that is unsubstituted or is substituted with 1, 2, or 3 $R^{1f'}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1g}$ is an unsubstituted pyridyl, pyridonyl, or pyridine N-oxide, or is a pyridyl, pyridonyl, or pyridine N-oxide substituted with 1, 2, 3, or 4 $R^{1g'}$ substituents;

$R^{1a'}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a'}$ groups that include a $C_6$-$C_{10}$ aryl group, the heteroaryl of any of the $R^{1a'}$ groups that include a heteroaryl group, the $C_3$-$C_8$ cycloalkyl of any of the $R^{1a'}$ groups that include a —$C_3$-$C_8$ cycloalkyl group, and the heterocyclyl of any of the $R^{1a'}$ groups that include a heterocyclyl group are unsubstituted or are substituted with 1, 2, or 3 $R^{1a''}$ substituents; and further wherein the $C_3$-$C_8$ cycloalkyl of any of the $R^{1a'}$ groups that include a —$C_3$-$C_8$ cycloalkyl group, and the heterocyclyl of any of the $R^{1a'}$ groups that include a heterocyclyl group may additionally be substituted with 1 or 2 oxo substituents, and the S atom of the heterocyclyl of any of the $R^{1a'}$ groups that include a heterocyclyl group may contain one or two oxo substituents, and still further wherein, the heteroaryl of any of the $R^{1a'}$ groups that include a heteroaryl group may include an N-oxide if the heteroaryl includes a N heteroatom;

$R^{1a''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1b}$ in each instance is independently selected from —F, —Cl, —Br, —I, —CN, —OH, =O, —O—($C_1$-$C_6$ alkyl), —O—($C_1$-$C_6$ haloalkyl), —O—($C_1$-$C_6$ perhaloalkyl), —$C_1$-$C_6$ alkyl, —$C_1$-$C_6$ haloalkyl, —$C_1$-$C_6$ perhaloalkyl, —$C_2$-$C_4$ alkenyl, =CH$_2$, =CH—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ haloalkyl)-OH, —($C_1$-$C_6$ haloalkyl)-O—($C_1$-$C_6$ alkyl), —($C_1$-$C_6$ perhaloalkyl)-OH, —($C_1$-$C_6$ perhaloalkyl)-O—($C_1$-$C_6$ alkyl), —O—($C_1$-

$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a phenyl group, or a monocyclic heteroaryl group with 5 or 6 ring members containing 1, 2, or 3 heteroatoms independently selected from N, O, or S, wherein the $R^{1b'}$ phenyl and $R^{1b'}$ heteroaryl groups are unsubstituted or are substituted with 1, 2, or 3, $R^{1b'}$ substituents; and further wherein two $R^{1b'}$ groups on a single carbon atom of a monocyclic $C_3$-$C_8$ cycloalkyl $R^{1b}$ group may join together with the carbon atom to which they are attached to form a heterocyclic ring having 3 to 6 members of which 1 or 2 are heteroatoms independently selected from O, N, and S;

$R^{1b''}$ is in each instance, independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_1$-$C_6$ alkyl, —$C_1$-$C_6$ haloalkyl, —$C_1$-$C_6$ perhaloalkyl, —$C_2$-$C_4$ alkenyl, —($C_1$-$C_6$ alkyl)-OH, —($C_1$-$C_6$ alkyl)-O—($C_1$-$C_6$ alkyl), —($C_1$-$C_6$ haloalkyl)-OH, —($C_1$-$C_6$ haloalkyl)-O—($C_1$-$C_6$ alkyl), —($C_1$-$C_6$ perhaloalkyl)-OH, —($C_1$-$C_6$ perhaloalkyl)-O—($C_1$-$C_6$ alkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl);

$R^{1c'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1c'}$ may also be oxo unless $R^{1c}$ is a 6-membered heterocyclic group that includes one N atom and includes at least one double bond, and further wherein two $R^{1c'}$ substituents on adjacent carbon atoms or on an adjacent carbon atom and an adjacent N atom of a 5- or 6-membered heterocyclic $R^{1c}$ group may join to form a 6 membered ring that may be saturated, partially saturated, or aromatic and may include 0, 1, or 2 N atoms and may further optionally be substituted with 1 or 2 $R^{1c''}$ substituent and may include an oxo substituent if the ring is not an aromatic ring and further wherein two $R^{1c'}$ substituents on adjacent carbon atoms or on an adjacent carbon atom and an adjacent N atom of a 5- or 6-membered heterocyclic $R^{1c}$ group may join to form a 5 membered ring that may be saturated, partially saturated, or aromatic and may include 0, 1, or 2 heteroatoms selected from N, O, or S and may further optionally be substituted with 1 or 2 $R^{1c''}$ substituent and may include an oxo substituent if the ring is not an aromatic ring;

$R^{1c''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1d'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2NH_2$, —S(=O)$_2$NH($C_1$-$C_6$ alkyl), —S(=O)$_2$N($C_1$-$C_6$ alkyl)$_2$, or —O-phenyl, wherein the phenyl of the —O-phenyl $R^{1d'}$ group may optionally be substituted with 1 or 2 $R^{1d''}$ substituents; and further wherein two $R^{1d'}$ substituents on adjacent carbon atoms of the phenyl $R^{1d}$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1d'''}$ substituent and may include an oxo substituent if the ring is not an aromatic ring;

$R^{1d''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1d'''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1e'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^{1f'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1f''}$ substituents; and further wherein two $R^{1f'}$ substituents on adjacent carbon atoms or on an adjacent carbon atom and an adjacent N atom of the 5- or 6-membered heteroaryl $R^{1f}$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1f'''}$ substituent and may include an oxo substituent if the ring is not an aromatic ring;

$R^{1f''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1f'''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1g'}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_1$-$C_6$ alkyl —OH, —$C_1$-$C_6$ haloalkyl-OH, —$C_1$-$C_6$ perhaloalkyl-OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —C(=O)-(heterocyclyl), a $C_3$-$C_6$ cycloalkyl group or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

$R^2$ is selected from —H, or $C_1$-$C_4$ alkyl;

$R^3$ is selected from an unsubstituted $C_1$-$C_{10}$ alkyl, a $C_1$-$C_{10}$ alkyl substituted with 1, 2, or 3 $R^{3a}$ substituents, an unsubstituted $C_3$-$C_8$ cycloalkyl, a $C_3$-$C_8$ cycloalkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3b}$=$CR^{3c}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, -Q, a group of formula —($C_3$-$C_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), $C_2$-$C_6$ alkenyl, $C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$ phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$, alkyl, or —C(=O)—(O—$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and $R^{4b}$ in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4b}$ group, the 3 to 6 membered heterocyclyl $R^{4b}$ group, the phenyl $R^{4b}$ group, and the a 5 or 6 membered heteroaryl $R^{4b}$ ring are unsubstituted or are substituted with 1 or 2 $R^{4c}$ substituents; and further wherein the 3 to 6 membered cycloalkyl $R^{4b}$ group and the 3 to 6 membered heterocyclyl $R^{4b}$ group may optionally be additionally substituted with an oxo substituent; and $R^{4c}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$.

Numerous other embodiments of the compound of Formula I and Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy or chronic kidney disease.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy or chronic kidney disease.

Other objects, features and advantages of the invention will become apparent to those skilled in the art from the following description and claims.

BRIEF DESCRIPTION OF THE DRAWINGS

FIG. 2 is a graph plotting different concentrations of angiotensin (AngII) with fixed concentration of pyr apelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyr apelin-13 when the human APJ receptor is expressed alone.

FIG. 3 is a graph plotting different concentrations of angiotensin (AngII) with fixed concentration of pyr apelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyr apelin-13 in the absence of APJ expression.

DETAILED DESCRIPTION OF THE INVENTION

Figure 1:
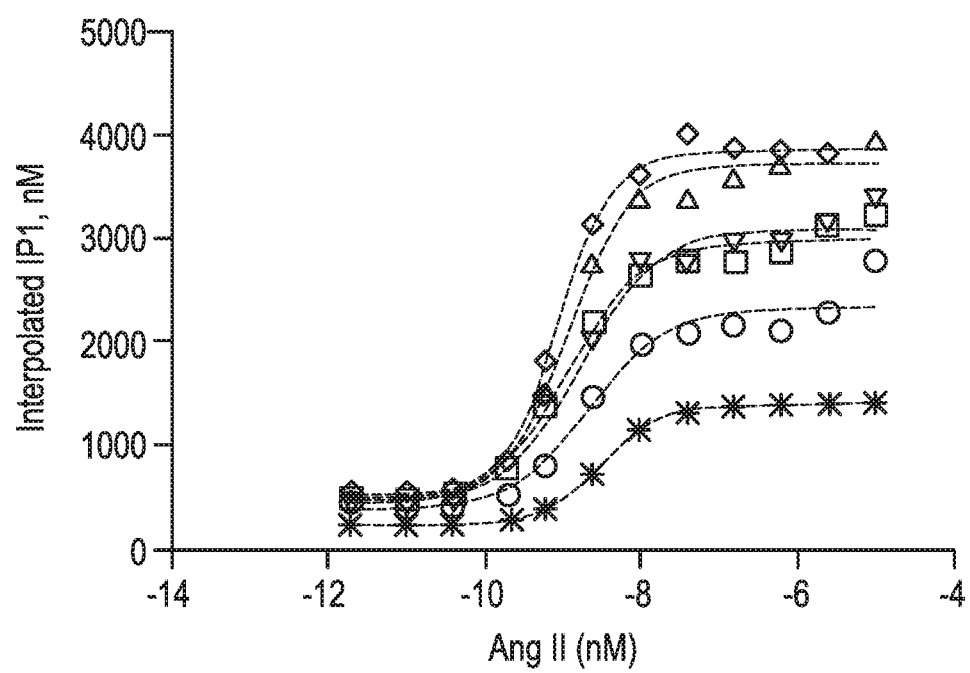
FIG. 1 is a graph plotting different concentrations of angiotensin (AngII) with fixed concentration of pyr apelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyr apelin-13 induces the positive cooperativity on the AT1R upon activation by APJ receptor.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when $R^4$ is a phenyl group and is substituted with two groups bonded to the C atoms adjacent to the point of attachment to the N atom of the pyrimidinone, then rotation of the phenyl may be restricted. In some instances, the barrier of rotation is high enough that the different atropisomers may be separated and isolated.

As used herein and unless otherwise indicated, the term "stereoisomer" or "stereomerically pine" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As described above, this invention encompasses the use of stereomerically pine forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

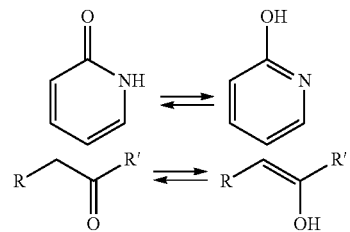

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$)alkyl group and an alkyl group having 1 to 4 carbon atoms may be referred to as a ($C_1$-$C_4$)alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—($C_1$-$C_6$ alkyl)-OH will be recognized as a group where an —O atom is bonded to a $C_1$-$C_6$ alkyl group and one of the H atoms bonded to a C atom of the $C_1$-$C_6$ alkyl group is replaced with a bond to the O atom of an —OH group. As another example, a group —O—($C_1$-$C_6$ alkyl)-O—($C_1$-$C_6$ alkyl) will be recognized as a group where an —O atom is bonded to a first $C_1$-$C_6$ alkyl group and one of the H atoms bonded to a C atom of the first $C_1$-$C_6$ alkyl group is replaced with a bond to a second O atom that is bonded to a second $C_1$-$C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or tram) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as —O—($C_1$-$C_6$ alkyl) groups. In some embodiments, an alkoxy group may include 1 to 4 carbon atoms and may be designated as —O—($C_1$-$C_4$) alkyl or as —O—($C_1$-$C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example, a cycloalkyl group having 3 to 8 ring members may be referred to as a ($C_3$-$C_8$)cycloalkyl, a cycloalkyl group having 3 to 7 ring members may be referred to as a (C$_3$-C$_7$)cycloalkyl and a cycloalkyl group having 4 to 7 ring members may be referred to as a (C$_4$-C$_7$)cycloalkyl. In certain embodiments, the cycloalkyl group can be a (C$_3$-C$_{10}$)cycloalkyl, a (C$_3$-C$_8$)cycloalkyl, a (C$_3$-C$_7$)cycloalkyl, a (C$_3$-C$_6$)cycloalkyl, or a (C$_4$-C$_7$)cycloalkyl group and these may be referred to as C$_3$-C$_{10}$ cycloalkyl, C$_3$-C$_8$ cycloalkyl, C$_3$-C$_7$ cycloalkyl, C$_3$-C$_6$ cycloalkyl, or C$_4$-C$_7$ cycloalkyl groups using alternative language. Cycloalkyl groups may be monocyclic or polycyclic. For the purposes of this application, the term "polycyclic" when used with respect to cycloalkyl will include bicyclic cycloalkyl groups such as, but not limited to, norbornane, bicyclo[1.1.1]pentane, and bicyclo[3.1.0]hexane, and cycloalkyl groups with more ring systems such as, but not limited to, cubane. The term "polycyclic" when used with respect to cycloalkyl will also include spirocyclic ring systems such as, but not limited to, spiro[2.2]pentane, spiro[2.3]hexane, spiro[3.3]heptane, and spiro[3.4]octane.

"Heterocyclyl" and "heterocyclic" refer to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

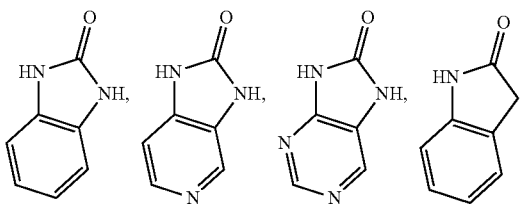

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (=O) or oxide (—O$^-$) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like. In heterocyclyl group containing a sulfur atom, the sulfur atom may be bonded to 0, 1, or 2 O atoms in addition to the adjacent ring members such that the sulfur may in various oxidation states. For example, a saturated 5-membered heterocycle containing one heteroatom which is a S may include the following heterocycles.

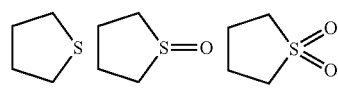

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, antiadherents, glidants, disintegrants, flavoring agents, coatings, binders, sweeteners, lubricants, sorbents, preservatives, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize this amount is typically not limited to a single dose, but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

EMBODIMENTS

The embodiments listed below are presented in numbered form for convenience and in ease and clarity of reference in referring back to multiple embodiments.

In a first embodiment, the invention provides a compound of Formula I or Formula II:

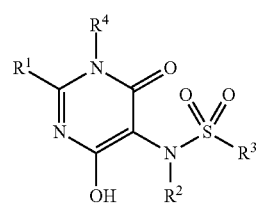

I

-continued $$\text{II}$$

[Structure II: pyrimidine with R¹ at position 2, R⁴ on N, OH, oxo, and sulfonamide group -N(R²)-S(=O)₂-R³]

or a pharmaceutically acceptable salt thereof, a tautomer thereof, a pharmaceutically acceptable salt of the tautomer, a stereoisomer of any of the foregoing, or a mixture thereof, wherein:

$R^1$ is selected from $R^{1a}$, $R^{1b}$, $R^{1c}$, $R^{1d}$, $R^{1e}$, $R^{1f}$, or $R^{1g}$;

$R^{1a}$ is an unsubstituted $C_1$-$C_8$ straight or branched chain alkyl or $R^{1a}$ is a $C_1$-$C_8$ straight or branched chain alkyl substituted with 1, 2, or 3 $R^{1a'}$ substituents;

$R^{1b}$ is an unsubstituted monocyclic $C_3$-$C_8$ cycloalkyl, an unsubstituted $C_5$-$C_8$ polycyclic cycloalkyl, an unsubstituted monocyclic $C_4$-$C_8$ cycloalkenyl, a monocyclic $C_3$-$C_8$ cycloalkyl substituted with 1, 2, 3, or 4 $R^{1b'}$ substituents, a $C_5$-$C_8$ polycyclic cycloalkyl substituted with 1, 2, or 3 $R^{1b'}$ substituents, or a monocyclic $C_4$-$C_8$ cycloalkenyl substituted with 1, 2, or 3 $R^{1b'}$ substituents;

$R^{1c}$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1c'}$ substituents;

$R^{1d}$ is a phenyl group that is unsubstituted or is substituted with 1, 2, or 3 $R^{1d'}$ substituents;

$R^{1e}$ is an unsubstituted furanyl, or is a furanyl substituted with 1, 2, or 3 $R^{1e'}$ substituents;

$R^{1f}$ is a 5- or 6-membered heteroaryl group that is unsubstituted or is substituted with 1, 2, or 3 $R^{1f'}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1g}$ is an unsubstituted pyridyl, pyridonyl, or pyridine N-oxide, or is a pyridyl, pyridonyl, or pyridine N-oxide substituted with 1, 2, 3, or 4 $R^{1g'}$ substituents;

$R^{1a'}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH₂, —NH($C_1$-$C_6$ alkyl), —N($C_1$-$C_6$ alkyl)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, —NHS(=O)₂—($C_1$-$C_6$ alkyl), —S(=O)₂—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a'}$ groups that include a $C_6$-$C_{10}$ aryl group, the heteroaryl of any of the $R^{1a'}$ groups that include a heteroaryl group, the $C_3$-$C_8$ cycloalkyl of any of the $R^{1a'}$ groups that include a —$C_3$-$C_8$ cycloalkyl group, and the heterocyclyl of any of the $R^{1a'}$ groups that include a heterocyclyl group are unsubstituted or are substituted with 1, 2, or 3 $R^{1a''}$ substituents; and further wherein the $C_3$-$C_8$ cycloalkyl of any of the $R^{1a'}$ groups that include a —$C_3$-$C_8$ cycloalkyl group, and the heterocyclyl of any of the $R^{1a'}$ groups that include a heterocyclyl group may additionally be substituted with 1 or 2 oxo substituents, and the S atom of the heterocyclyl of any of the $R^{1a'}$ groups that include a heterocyclyl group may contain one or two oxo substituents, and still further wherein, the heteroaryl of any of the $R^{1a'}$ groups that include a heteroaryl group may include an N-oxide if the heteroaryl includes a N heteroatom;

$R^{1a''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH₂, —NH($C_1$-$C_6$ alkyl), —N($C_1$-$C_6$ alkyl)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, or —S(=O)₂—($C_1$-$C_6$ alkyl);

$R^{1b'}$ in each instance is independently selected from —F, —Cl, —Br, —I, —CN, —OH, =O, —O—($C_1$-$C_6$ alkyl), —O—($C_1$-$C_6$ haloalkyl), —O—($C_1$-$C_6$ perhaloalkyl), —$C_1$-$C_6$ alkyl, —$C_1$-$C_6$ haloalkyl, —$C_1$-$C_6$ perhaloalkyl, —$C_2$-$C_4$ alkenyl, =CH₂, =CH—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ haloalkyl)-OH, —($C_1$-$C_6$ haloalkyl)-O—($C_1$-$C_6$ alkyl), —($C_1$-$C_6$ perhaloalkyl)-OH, —($C_1$-$C_6$ perhaloalkyl)-O—($C_1$-$C_6$ alkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH₂, —NH($C_1$-$C_6$ alkyl), —N($C_1$-$C_6$ alkyl)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, —NHS(=O)₂—($C_1$-$C_6$ alkyl), —S(=O)₂—($C_1$-$C_6$ alkyl), a phenyl group, or a monocyclic heteroaryl group with 5 or 6 ring members containing 1, 2, or 3 heteroatoms independently selected from N, O, or S, wherein the $R^{1b'}$ phenyl and $R^{1b'}$ heteroaryl groups are unsubstituted or are substituted with 1, 2, or 3, $R^{1b'}$ substituents; and further wherein two $R^{1b'}$ groups on a single carbon atom of a monocyclic $C_3$-$C_8$ cycloalkyl $R^{1b}$ group may join together with the carbon atom to which they are attached to form a heterocyclic ring having 3 to 6 members of which 1 or 2 are heteroatoms independently selected from O, N, and S;

$R^{1b''}$ is in each instance, independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_1$-$C_6$ alkyl, —$C_1$-$C_6$ haloalkyl, —$C_1$-$C_6$ perhaloalkyl, —$C_2$-$C_4$ alkenyl, —($C_1$-$C_6$ alkyl)-OH, —($C_1$-$C_6$ alkyl)-O—($C_1$-$C_6$ alkyl), —($C_1$-$C_6$ haloalkyl)-OH, —($C_1$-$C_6$ haloalkyl)-O—($C_1$-$C_6$ alkyl), —($C_1$-$C_6$ perhaloalkyl)-OH, —($C_1$-$C_6$ perhaloalkyl)-O—($C_1$-$C_6$ alkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl);

$R^{1c'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1c}$ may also be oxo unless $R^{1c}$ is a 6-membered heterocyclic group that includes one N atom and includes at least one double bond, and further wherein two $R^{1c'}$ substituents on adjacent carbon atoms or on an adjacent carbon atom and an adjacent N atom of a 5- or 6-membered heterocyclic $R^{1c}$ group may join to form a 6 membered ring that may be saturated, partially saturated, or aromatic and may include 0, 1, or 2 N atoms and may further optionally be substituted with 1 or 2 $R^{1c''}$ substituent and may include an oxo substituent if the ring is not an aromatic ring and further wherein two $R^{1c'}$ substituents on adjacent carbon atoms or on an adjacent carbon atom and an adjacent N atom of a 5- or 6-membered heterocyclic $R^{1c}$ group may join to form a 5 membered ring that may be saturated, partially saturated, or aromatic and may include 0, 1, or 2 heteroatoms selected from N, O, or S and may further optionally be substituted with 1 or 2 $R^{1c''}$ substituent and may include an oxo substituent if the ring is not an aromatic ring;

$R^{1c''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1d'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, or —O-phenyl, wherein the phenyl of the —O-phenyl $R^{1d'}$ group may optionally be substituted with 1 or 2 $R^{1d''}$ substituents; and further wherein two $R^{1d'}$ substituents on adjacent carbon atoms of the phenyl $R^{1d}$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1d'''}$ substituent and may include an oxo substituent if the ring is not an aromatic ring;

$R^{1d''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1d'''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1e'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-

O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), or —C(=O)N($C_1$-$C_6$ alkyl)$_2$;

$R^{1f}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1f'}$ substituents; and further wherein two $R^{1f}$ substituents on adjacent carbon atoms or on an adjacent carbon atom and an adjacent N atom of the 5- or 6-membered heteroaryl $R^{1f}$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1f'}$ substituent and may include an oxo substituent if the ring is not an aromatic ring;

$R^{1f'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)NH$_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1f''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1g'}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_1$-$C_6$ alkyl —OH, —$C_1$-$C_6$ haloalkyl-OH, —$C_1$-$C_6$ perhaloalkyl-OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —C(=O)-(heterocyclyl), a $C_3$-$C_6$ cycloalkyl group or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

$R^2$ is selected from —H, or $C_1$-$C_4$ alkyl;

$R^3$ is selected from an unsubstituted $C_1$-$C_{10}$ alkyl, a $C_1$-$C_{10}$ alkyl substituted with 1, 2, or 3 $R^{3a}$ substituents, an unsubstituted $C_3$-$C_8$ cycloalkyl, a $C_3$-$C_8$ cycloalkyl substituted with 1, 2, or 3 $R^{3a}$ substituents, a group of formula —(CR$^{3b}$R$^{3c}$)-Q, a group of formula —(CR$^{3d}$R$^{3e}$)—(CR$^{3f}$R$^{3g}$)-Q, a group of formula —(CR$^{3b}$=CR$^{3c}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, -Q, a group of formula —($C_3$-$C_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, $C_2$-$C_6$ alkynyl, —NH$_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—

($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_{2j}$ phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and $R^{4b}$ in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4b}$ group, the 3 to 6 membered heterocyclyl $R^{4b}$ group, the phenyl $R^{4b}$ group, and the a 5 or 6 membered heteroaryl $R^{4b}$ ring are unsubstituted or are substituted with 1 or 2 $R^{4c}$ substituents; and further wherein the 3 to 6 membered cycloalkyl $R^{4b}$ group and the 3 to 6 membered heterocyclyl $R^{4b}$ group may optionally be additionally substituted with an oxo substituent; and $R^{4c}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$.

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is $R^{1a}$.

3. The compound of embodiment 2 or the pharmaceutically acceptable salt thereof, the tautomer thereof, the pharmaceutically acceptable salt of the tautomer, the stereoisomer of any of the foregoing, or the mixture thereof, wherein $R^{1a}$ is an unsubstituted $C_2$-$C_6$ straight or branched chain alkyl or $R^{1a}$ is a $C_1$-$C_6$ straight or branched chain alkyl substituted with 1, 2, or 3 $R^{1a'}$ substituents, wherein $R^{1a'}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —NHS(=O)$_2$—(C$_1$-C$_6$ alkyl), or —S(=O)$_2$—(C$_1$-C$_6$ alkyl).

4. The compound of embodiment 3 or the pharmaceutically acceptable salt thereof, the tautomer thereof, the pharmaceutically acceptable salt of the tautomer, the stereoisomer of any of the foregoing, or the mixture thereof, wherein R$^{1a}$ is an unsubstituted C$_2$-C$_6$ straight or branched chain alkyl or R$^{1a}$ is a C$_1$-C$_6$ straight or branched chain alkyl substituted with 1, 2, or 3 R$^{1a'}$ substituents, wherein R$^{1a'}$ in each instance is independently selected from —F, —Cl, —Br, —I, —CN, —OH, —O—(C$_1$-C$_6$ alkyl), —O—(C$_1$-C$_6$ haloalkyl), or —O—(C$_1$-C$_6$ perhaloalkyl).

5. The compound of embodiment 4 or the pharmaceutically acceptable salt thereof, the tautomer thereof, the pharmaceutically acceptable salt of the tautomer, the stereoisomer of any of the foregoing, or the mixture thereof, wherein R$^{1a}$ is selected from

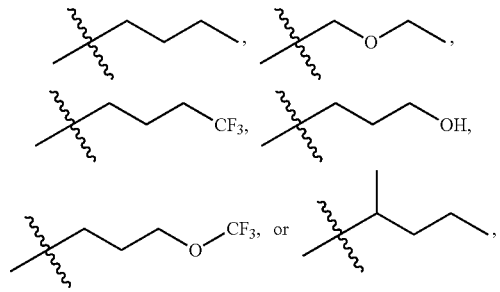

wherein the symbol ∽, when drawn across a bond, indicates the point of attachment to the rest of the molecule.

6. The compound of embodiment 1 or the pharmaceutically acceptable salt thereof, the tautomer thereof, the pharmaceutically acceptable salt of the tautomer, the stereoisomer of any of the foregoing, or the mixture thereof, wherein R$^1$ is R$^{1b}$.

7. The compound of embodiment 6 or the pharmaceutically acceptable salt thereof, the tautomer thereof, the pharmaceutically acceptable salt of the tautomer, the stereoisomer of any of the foregoing, or the mixture thereof, wherein R$^{1b}$ is an unsubstituted monocyclic C$_3$-C$_8$ cycloalkyl or is a monocyclic C$_3$-C$_8$ cycloalkyl substituted with 1, 2, or 3 R$^{1b'}$ substituents.

8. The compound of embodiment 7 or the pharmaceutically acceptable salt thereof, the tautomer thereof, the pharmaceutically acceptable salt of the tautomer, the stereoisomer of any of the foregoing, or the mixture thereof, wherein R$^{1b}$ is an unsubstituted monocyclic C$_3$-C$_6$ cycloalkyl or is a monocyclic C$_3$-C$_7$ cycloalkyl substituted with 1 or 2 R$^{1b'}$ substituents, wherein R$^{1b'}$ in each instance is independently selected from —F, —Cl, —Br, —I, —CN, —OH, =O, —O—(C$_1$-C$_6$ alkyl), —O—(C$_1$-C$_6$ haloalkyl), —O—(C$_1$-C$_6$ perhaloalkyl), —C$_1$-C$_6$ alkyl, —C$_1$-C$_6$ haloalkyl, or —C$_1$-C$_6$ perhaloalkyl.

9. The compound of embodiment 8 or the pharmaceutically acceptable salt thereof, the tautomer thereof, the pharmaceutically acceptable salt of the tautomer, the stereoisomer of any of the foregoing, or the mixture thereof, wherein R$^{1b}$ is selected from

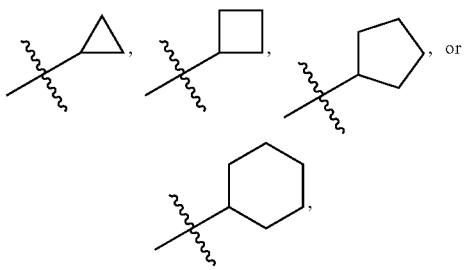

wherein the symbol ∽, when drawn across a bond, indicates the point of attachment to the rest of the molecule.

10. The compound of embodiment 1 or the pharmaceutically acceptable salt thereof, the tautomer thereof, the pharmaceutically acceptable salt of the tautomer, the stereoisomer of any of the foregoing, or the mixture thereof, wherein R$^1$ is R$^{1c}$.

11. The compound of embodiment 10 or the pharmaceutically acceptable salt thereof, the tautomer thereof, the pharmaceutically acceptable salt of the tautomer, the stereoisomer of any of the foregoing, or the mixture thereof, wherein R$^{1c}$ a 5- or 6-membered saturated or partially saturated heterocyclic group that includes 1, 2, or 3 heteroatoms independently selected from N, O, or S that is unsubstituted or is substituted with 1, 2, or 3 R$^{1c'}$ substituents.

12. The compound of embodiment 10 or the pharmaceutically acceptable salt thereof, the tautomer thereof, the pharmaceutically acceptable salt of the tautomer, the stereoisomer of any of the foregoing, or the mixture thereof, wherein R$^{1c}$ a 5- or 6-membered saturated or partially saturated heterocyclic group that includes 1, 2, or 3 heteroatoms independently selected from N, O, or S that is unsubstituted or is substituted with 1, 2, or 3 R$^{1c'}$ substituents, wherein the substituted or unsubstituted R$^{1c}$ is selected from tetrahydrofuranyl, pyrrolidinyl, tetrahydropyranyl, piperidinyl, piperazinyl, or morpholinyl.

13. The compound of embodiment 10 or the pharmaceutically acceptable salt thereof, the tautomer thereof, the pharmaceutically acceptable salt of the tautomer, the stereoisomer of any of the foregoing, or the mixture thereof, wherein R$^{1c}$ is selected from

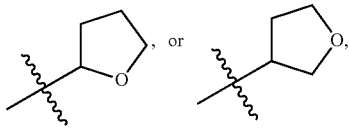 [SMILES: *C1CCCO1 ; *C1CCOC1]

wherein the symbol ∽, when drawn across a bond, indicates the point of attachment to the rest of the molecule.

14. The compound of embodiment 1 or the pharmaceutically acceptable salt thereof, the tautomer thereof, the pharmaceutically acceptable salt of the tautomer, the stereoisomer of any of the foregoing, or the mixture thereof, wherein R$^1$ is R$^{1d}$.

15. The compound of embodiment 14 or the pharmaceutically acceptable salt thereof, the tautomer thereof, the pharmaceutically acceptable salt of the tautomer, the stereoisomer of any of the foregoing, or the mixture thereof, wherein R$^{1d}$ is an unsubstituted phenyl or is a phenyl substituted with 1 or 2 R$^{1d'}$ substituents, wherein the R$^{1d'}$ substituents are independently selected from —F, —Cl, —Br, —I, —C$_1$-C$_6$ alkyl, —C$_1$-C$_6$ haloalkyl, —C$_1$-C$_6$ perhaloalkyl, —(C₁-C₆ alkyl)-OH, —(C₁-C₆ haloalkyl)-OH, —(C₁-C₆ perhaloalkyl)-OH, —(C₁-C₆ alkyl)-O—(C₁-C₆ alkyl), —CN, —OH, —O—(C₁-C₆ alkyl), —O—(C₁-C₆ haloalkyl), —O—(C₁-C₆ perhaloalkyl), —NH₂, —NH(C₁-C₆ alkyl), —N(C₁-C₆ alkyl)₂, —C(=O)—(C₁-C₆ alkyl), —C(=O)OH, —C(=O)—O—(C₁-C₆ alkyl), —C(=O)NH₂, —C(=O)NH(C₁-C₆ alkyl), —C(=O)N(C₁-C₆ alkyl)₂, —S(=O)₂—(C₁-C₆ alkyl), —S(=O)₂NH₂, —S(=O)₂NH(C₁-C₆ alkyl), or —S(=O)₂N(C₁-C₆ alkyl)₂.

16. The compound of embodiment 1 or the pharmaceutically acceptable salt thereof, the tautomer thereof, the pharmaceutically acceptable salt of the tautomer, the stereoisomer of any of the foregoing, or the mixture thereof, wherein R¹ is R¹ᶜ.

17. The compound of embodiment 16 or the pharmaceutically acceptable salt thereof, the tautomer thereof, the pharmaceutically acceptable salt of the tautomer, the stereoisomer of any of the foregoing, or the mixture thereof, wherein R¹ᵉ is an unsubstituted furanyl substituted with 1 or 2 R¹ᵉ′ substituents.

18. The compound of embodiment 16 or the pharmaceutically acceptable salt thereof, the tautomer thereof, the pharmaceutically acceptable salt of the tautomer, the stereoisomer of any of the foregoing, or the mixture thereof, wherein R¹ᵉ is an unsubstituted furanyl substituted with 1 or 2 R¹ᵉ′ substituents, wherein the R¹ᵉ′ substituents are independently selected from —F, —Cl, —Br, —I, —C₁-C₆ alkyl, —C₁-C₆ haloalkyl, —C₁-C₆ perhaloalkyl, —(C₁-C₆ alkyl)-O—(C₁-C₆ alkyl), —CN, —OH, —O—(C₁-C₆ alkyl), —O—(C₁-C₆ haloalkyl), or —O—(C₁-C₆ perhaloalkyl).

19. The compound of embodiment 16 or the pharmaceutically acceptable salt thereof, the tautomer thereof, the pharmaceutically acceptable salt of the tautomer, the stereoisomer of any of the foregoing, or the mixture thereof, wherein R¹ᵉ is selected from

wherein the symbol ∼∼∼, when drawn across a bond, indicates the point of attachment to the rest of the molecule.

20. The compound of embodiment 1 or the pharmaceutically acceptable salt thereof, the tautomer thereof, the pharmaceutically acceptable salt of the tautomer, the stereoisomer of any of the foregoing, or the mixture thereof, wherein R¹ is R¹ᶠ.

21. The compound of embodiment 20 or the pharmaceutically acceptable salt thereof, the tautomer thereof, the pharmaceutically acceptable salt of the tautomer, the stereoisomer of any of the foregoing, or the mixture thereof, wherein R¹ᶠ is selected from

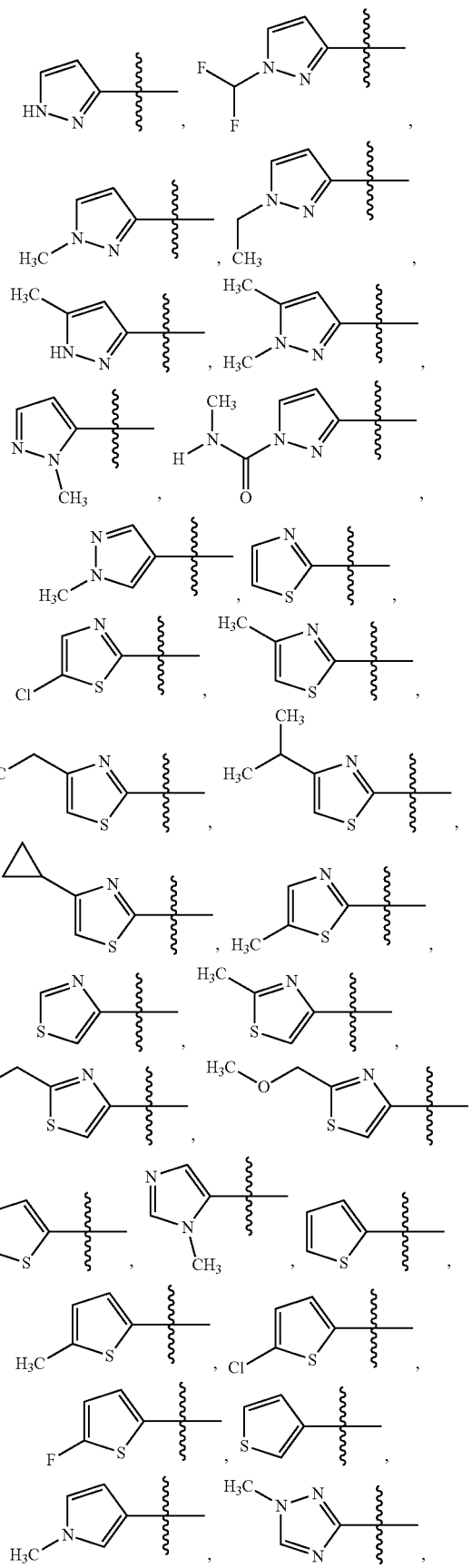

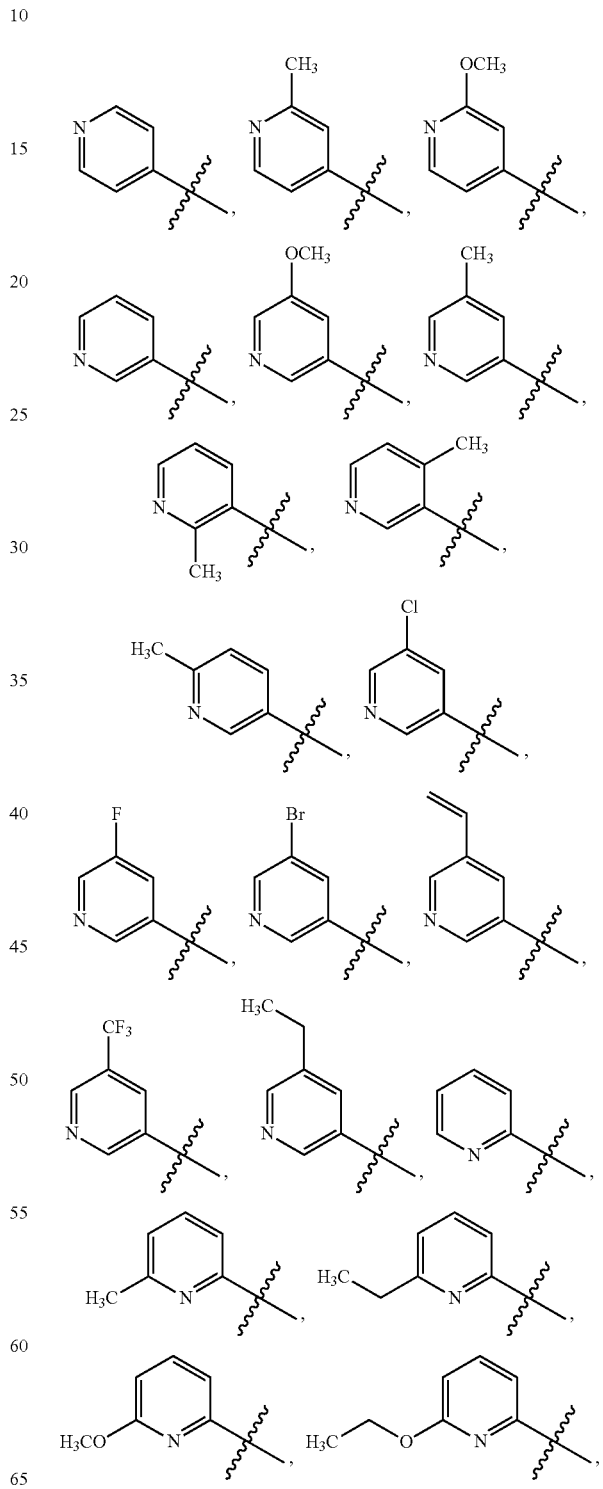

pharmaceutically acceptable salt of the tautomer, the stereoisomer of any of the foregoing, or the mixture thereof, wherein R¹ is R^{1g}.

23. The compound of embodiment 22 or the pharmaceutically acceptable salt thereof, the tautomer thereof, the pharmaceutically acceptable salt of the tautomer, the stereoisomer of any of the foregoing, or the mixture thereof, wherein R^{1g} is selected from wherein the symbol , when drawn across a bond, indicates the point of attachment to the rest of the molecule.

22. The compound of embodiment 1 or the pharmaceutically acceptable salt thereof, the tautomer thereof, the -continued

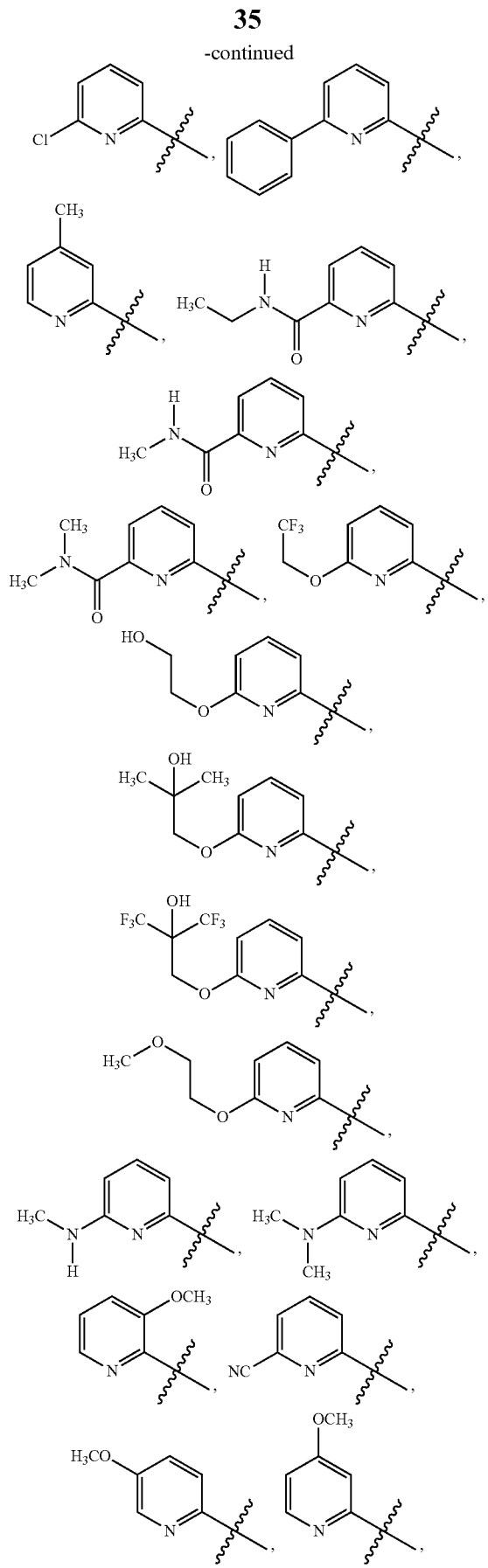

-continued

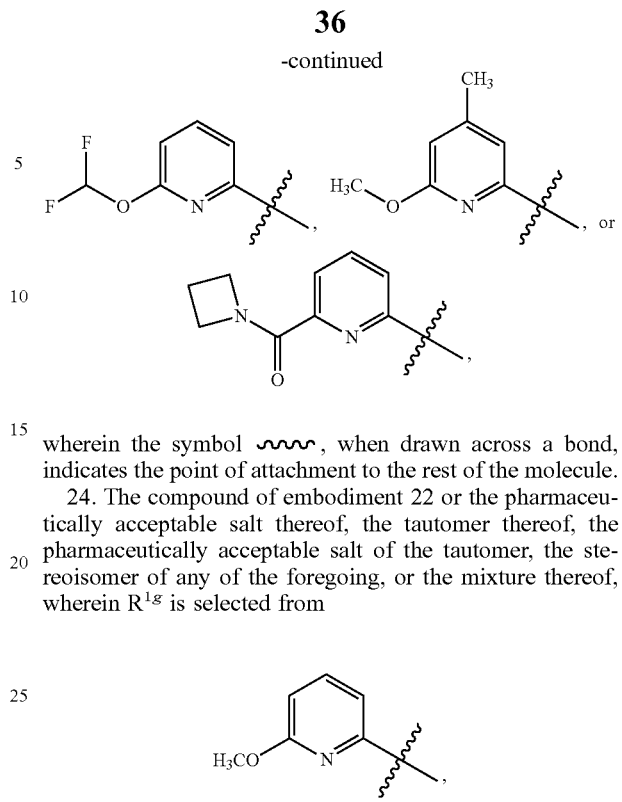

wherein the symbol ∿∿∿, when drawn across a bond, indicates the point of attachment to the rest of the molecule.

24. The compound of embodiment 22 or the pharmaceutically acceptable salt thereof, the tautomer thereof, the pharmaceutically acceptable salt of the tautomer, the stereoisomer of any of the foregoing, or the mixture thereof, wherein $R^{1g}$ is selected from wherein the symbol ∿∿∿, when drawn across a bond, indicates the point of attachment to the rest of the molecule.

25. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is an unsubstituted $C_1$-$C_{10}$ alkyl or is a $C_1$-$C_{10}$ alkyl substituted with 1, 2, or 3 $R^{3a}$ substituents.

26. The compound of embodiment 25 or the pharmaceutically acceptable salt thereof, the tautomer thereof, the pharmaceutically acceptable salt of the tautomer, the stereoisomer of any of the foregoing, or the mixture thereof, wherein $R^3$ is selected from —$CH_3$, —$CH_2CH_3$, —$CH_2CH_2CH_3$, —$CH_2CH_2CH_2CH_3$, or —$CH(CH_3)_2$.

27. The compound of embodiment 25 or the pharmaceutically acceptable salt thereof, the tautomer thereof, the pharmaceutically acceptable salt of the tautomer, the stereoisomer of any of the foregoing, or the mixture thereof, wherein $R^3$ is —$CH(CH_3)_2$.

28. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula a group of formula —$(CR^{3b}R^{3c})$-Q.

29. The compound of embodiment 28 or the pharmaceutically acceptable salt thereof, the tautomer thereof, the pharmaceutically acceptable salt of the tautomer, the stereoisomer of any of the foregoing, or the mixture thereof, wherein $R^3$ is —$CH_2$-Q.

30. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula a group of formula -(heterocyclyl)-Q.

31. The compound of embodiment 30 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a piperidinyl that is unsubstituted or is substituted with 1 or 2 $R^{3h}$ substituent.

32. The compound of embodiment 30 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula

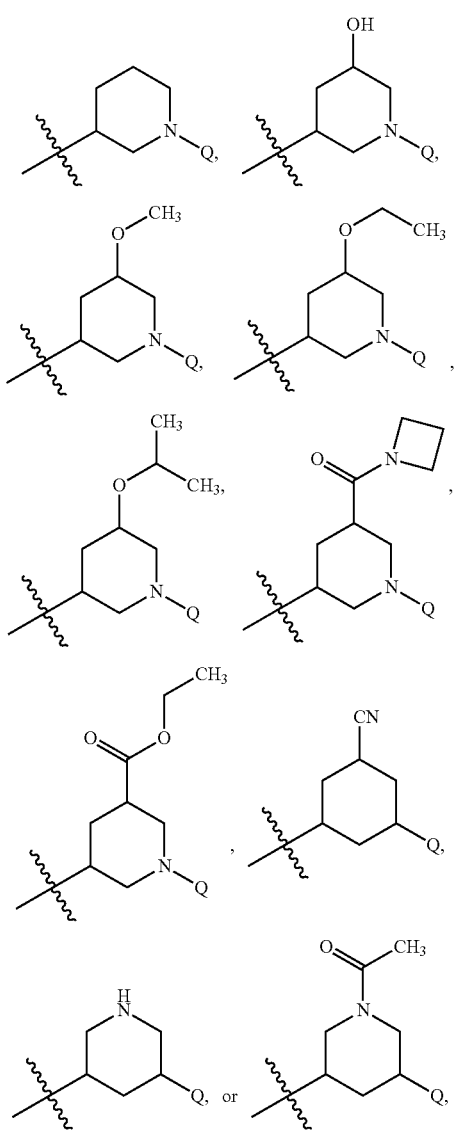

wherein the symbol ∿∿∿, when drawn across a bond, indicates the point of attachment to the rest of the molecule.

33. The compound of embodiment 30 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula

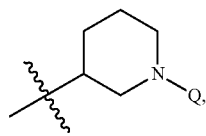

wherein the symbol ∿∿∿, when drawn across a bond, indicates the point of attachment to the rest of the molecule.

34. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -Q.

34. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q.

36. The compound of embodiment 35 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

37. The compound of embodiment 35 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, or —$C_1$-$C_6$ alkyl; and $R^{3f}$ and $R^{3g}$ are independently selected from —H, —$C_1$-$C_6$ alkyl, —OH, or —O—($C_1$-$C_6$ alkyl).

38. The compound of any one of embodiments 35-37 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is not —H.

39. The compound of any one of embodiments 35-37 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is a —$C_1$-$C_6$ alkyl.

40. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is selected from

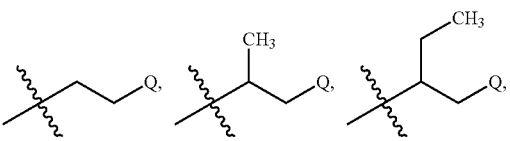

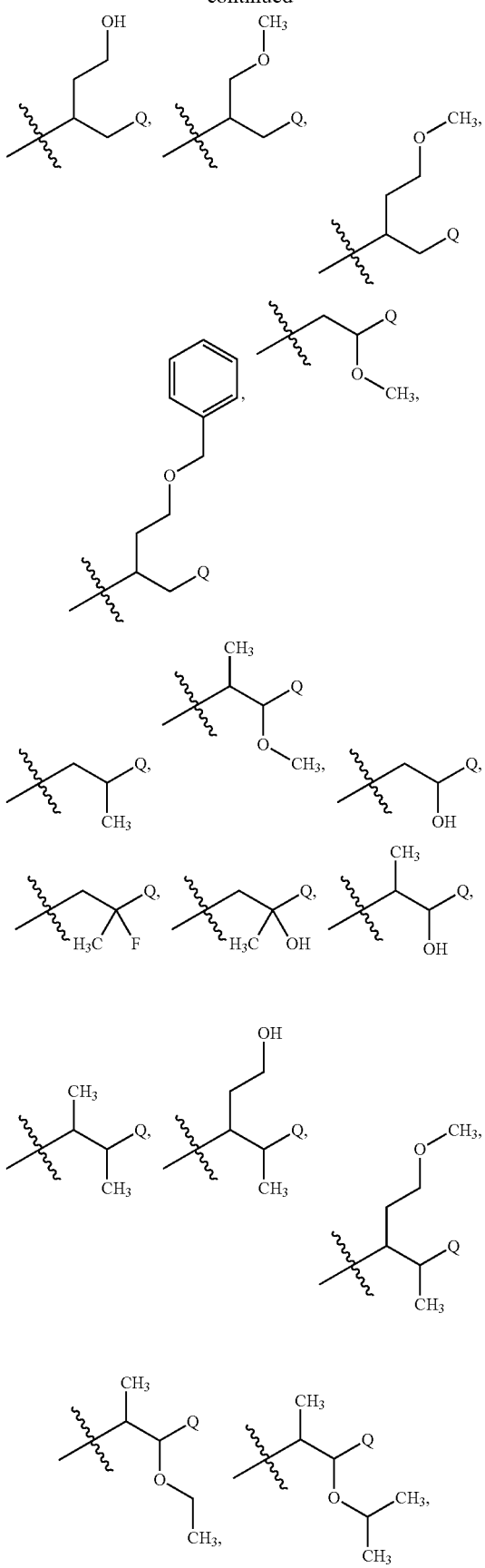

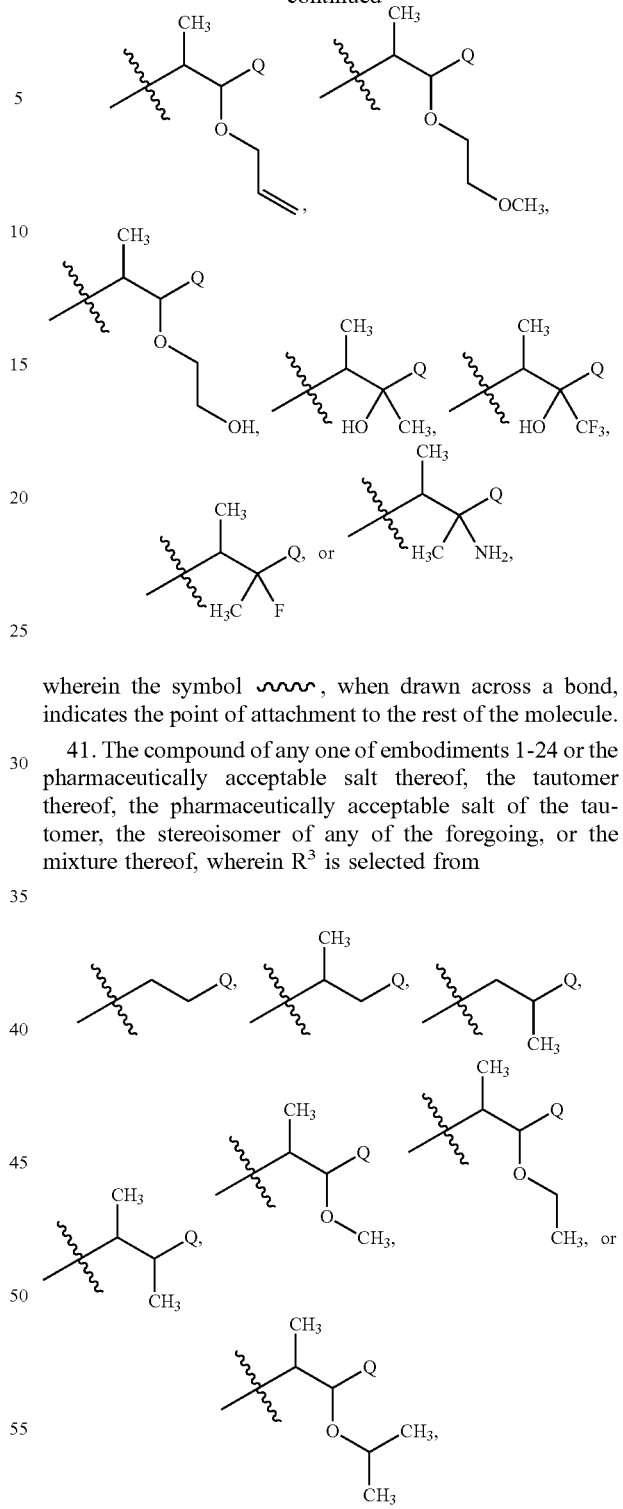

wherein the symbol ∿∿∿, when drawn across a bond, indicates the point of attachment to the rest of the molecule.

41. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is selected from

wherein the symbol ∿∿∿, when drawn across a bond, indicates the point of attachment to the rest of the molecule.

42. The compound of any one of embodiments 1-24 or the pharmaceutically acceptable salt thereof, the tautomer thereof, the pharmaceutically acceptable salt of the tautomer, the stereoisomer of any of the foregoing, or the mixture thereof, wherein $R^3$ is selected from

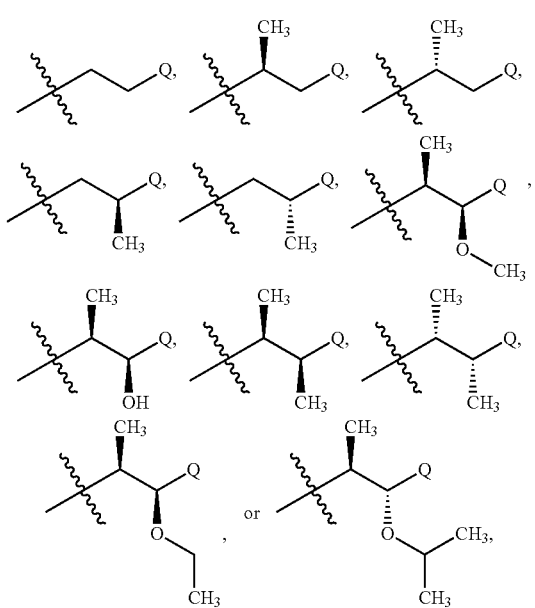

wherein the symbol ∿, when drawn across a bond, indicates the point of attachment to the rest of the molecule.

43. The compound of any one of embodiments 1-24 or 28-42 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, phenyl, naphthalenyl, or cyclohexyl any of which may be unsubstituted or substituted with 1, 2, or 3 $R^Q$ substituents.

44. The compound of embodiment 43 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, or phenyl any of which may be unsubstituted or substituted with 1, 2, or 3 $R^Q$ substituents.

45. The compound of embodiment 43 or the pharmaceutically acceptable salt thereof, the tautomer thereof, the pharmaceutically acceptable salt of the tautomer, the stereoisomer of any of the foregoing, or the mixture thereof, wherein Q is an unsubstituted phenyl or is a phenyl substituted with 1, 2, or 3 $R^Q$ substituents.

46. The compound of any one of embodiments 1-24 or 28-42 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

47. The compound of any of embodiments 1-24 or 28-42 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl or pyridinyl group and Q is unsubstituted or is substituted with 1, 2, or 3 $R^Q$ substituents.

48. The compound of any of embodiments 1-24 or 28-42 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl group and Q is unsubstituted or is substituted with 1, 2, or 3 $R^Q$ substituents.

49. The compound of any one of embodiments 1-24 or 28-48 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), or —O—($C_1$-$C_6$ perhaloalkyl).

50. The compound of any one of embodiments 1-24 or 28-48 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

51. The compound of any one of embodiments 1-24 or 28-42 the pharmaceutically acceptable salt thereof, the tautomer thereof, the pharmaceutically acceptable salt of the tautomer, the stereoisomer of any of the foregoing, or the mixture thereof, wherein Q is selected from

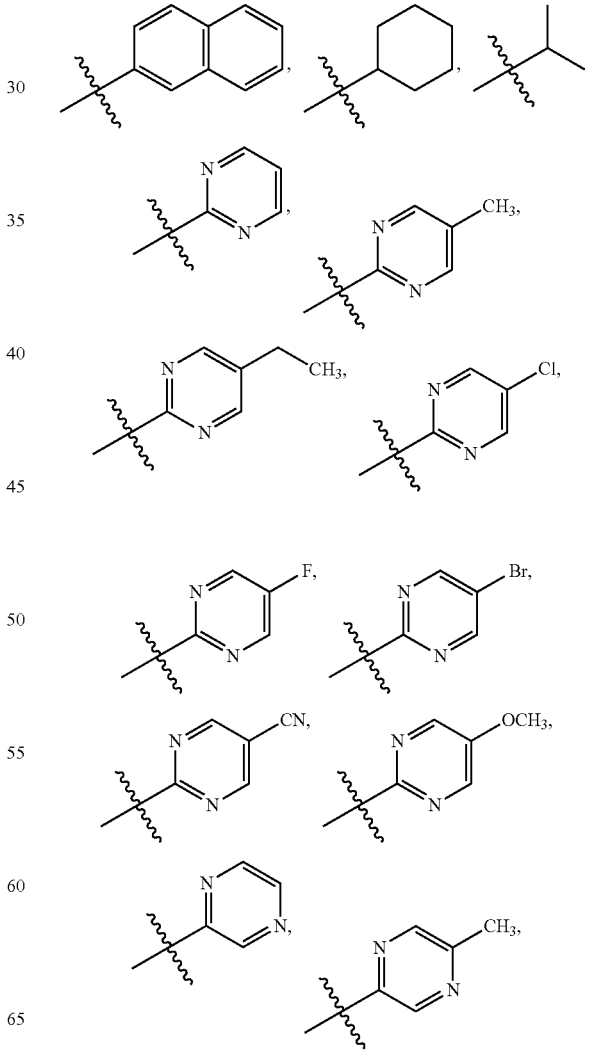

43

-continued

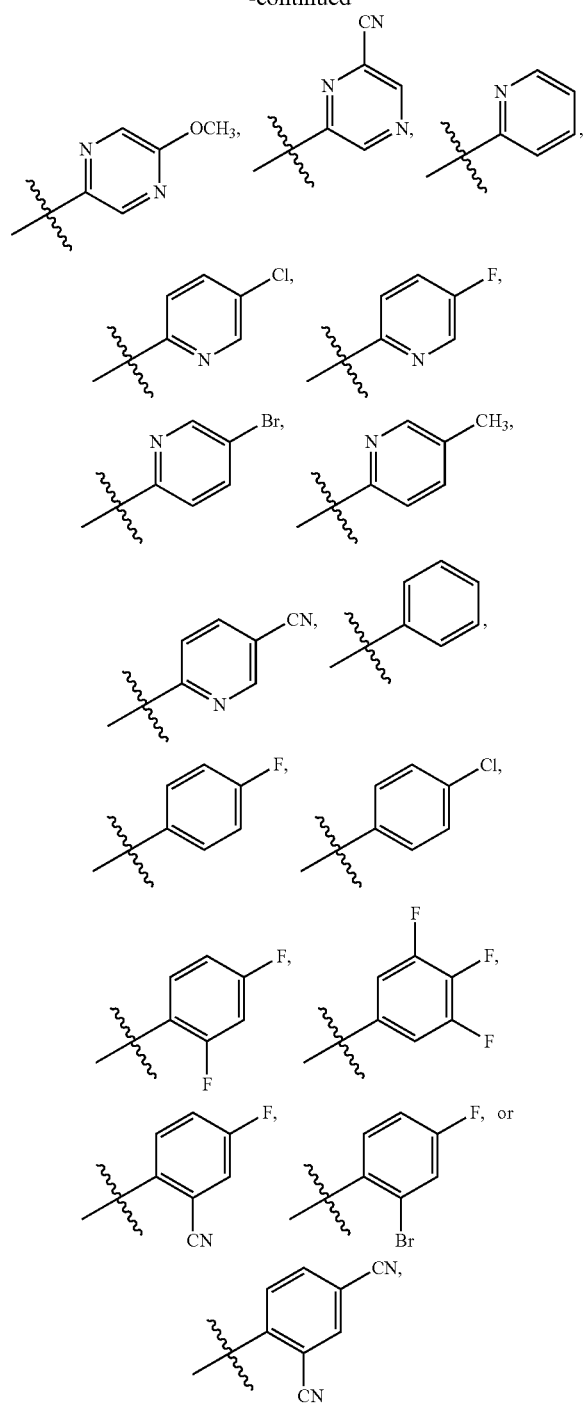

wherein the symbol ∿∿∿, when drawn across a bond, indicates the point of attachment to the rest of the molecule.

52. The compound of any one of embodiments 1-24 or 28-42 or the pharmaceutically acceptable salt thereof, the tautomer thereof, the pharmaceutically acceptable salt of the tautomer, the stereoisomer of any of the foregoing, or the mixture thereof, wherein Q is selected from

44

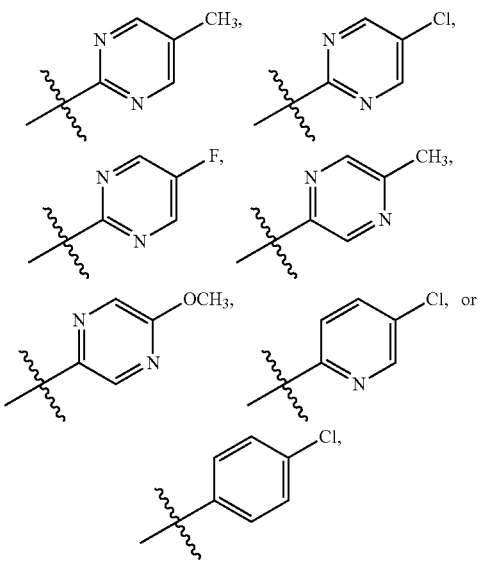

wherein the symbol ∿∿∿, when drawn across a bond, indicates the point of attachment to the rest of the molecule.

53. The compound of embodiment 52 or the pharmaceutically acceptable salt thereof, the tautomer thereof, the pharmaceutically acceptable salt of the tautomer, the stereoisomer of any of the foregoing, or the mixture thereof, wherein Q is

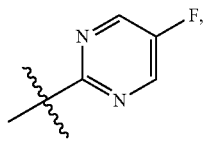 [SMILES: *c1ncc(F)cn1]

wherein the symbol ∿∿∿, when drawn across a bond, indicates the point of attachment to the rest of the molecule.

54. The compound of embodiment 52 or the pharmaceutically acceptable salt thereof, the tautomer thereof, the pharmaceutically acceptable salt of the tautomer, the stereoisomer of any of the foregoing, or the mixture thereof, wherein Q is

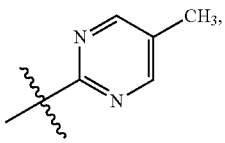

wherein the symbol ∿∿∿, when drawn across a bond, indicates the point of attachment to the rest of the molecule.

55. The compound of any one of embodiments 1-54 or the pharmaceutically acceptable salt thereof, the tautomer thereof, the pharmaceutically acceptable salt of the tautomer, the stereoisomer of any of the foregoing, or the mixture thereof, wherein $R^2$ is —H.

56. The compound of any one of embodiments 1-55 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, or 3 $R^{4a}$ substituents.

57. The compound of any one of embodiments 1-56 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, —NH($C_1$-$C_6$ alkyl-OH), —C(=O)$NH_2$, —C(=O)NH($C_1$-$C_6$ alkyl), or —C(=O)N($C_1$-$C_6$ alkyl)$_2$.

58. The compound of embodiment 57 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —$CH_3$, —F, —Cl, —Br, —CN, —$CF_3$, —$OCH_3$, or —$OCHF_2$.

59. The compound of embodiment 58 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F or, —$OCH_3$.

60. The compound of any one of embodiments 1-55 or the pharmaceutically acceptable salt thereof, the stereoisomer of any of the foregoing, or the mixture thereof, wherein $R^4$ is selected from

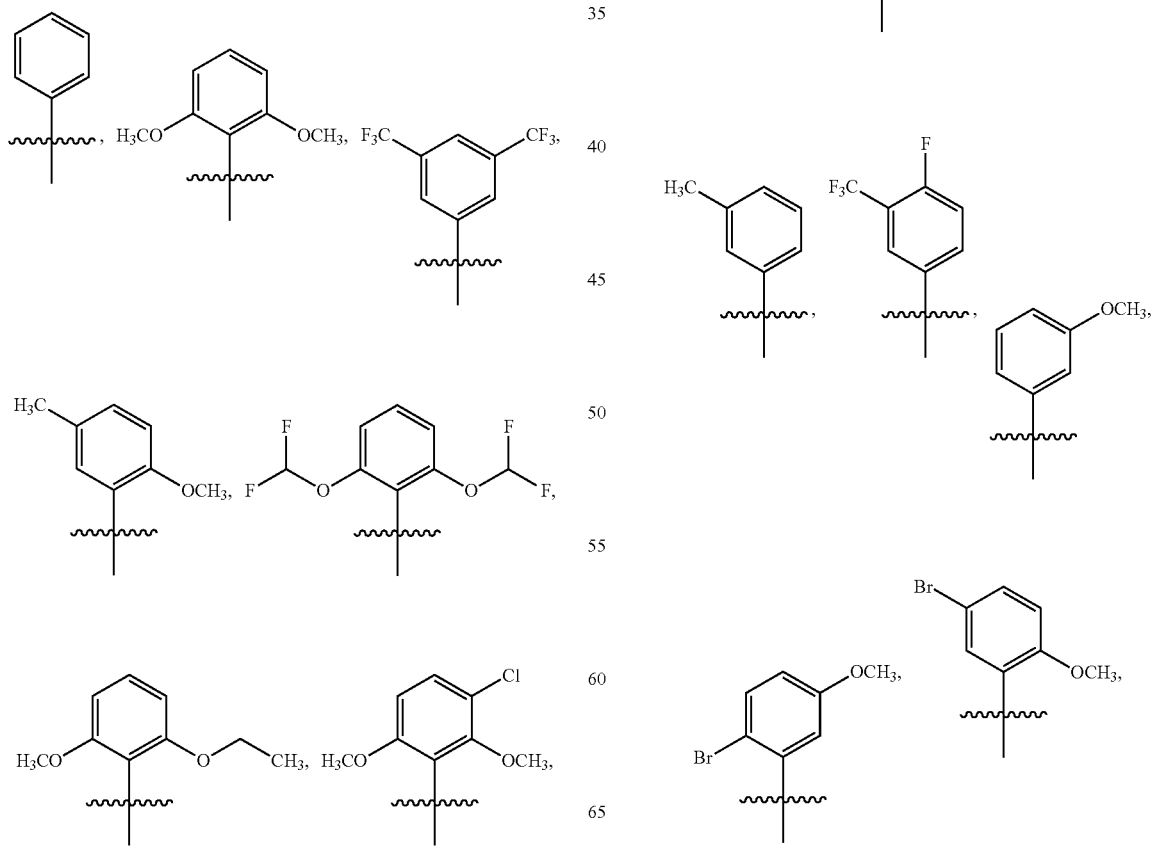
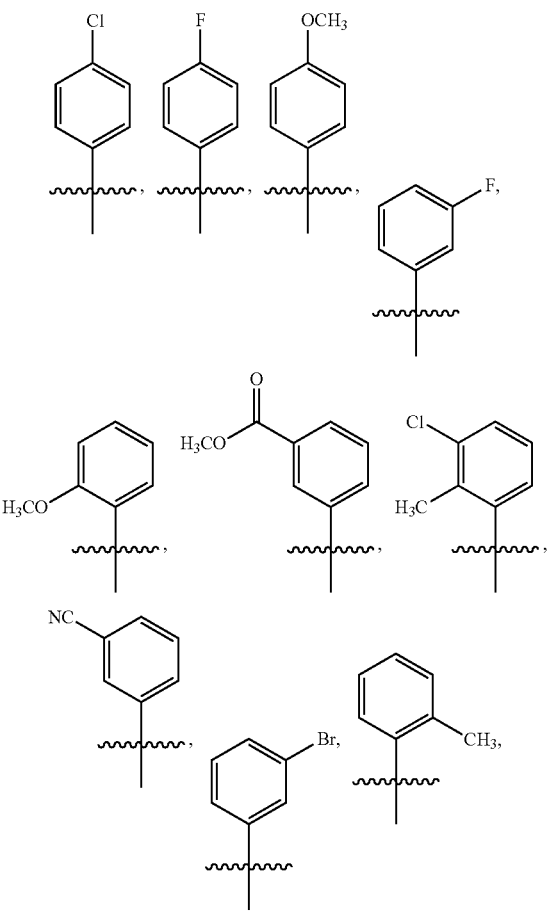

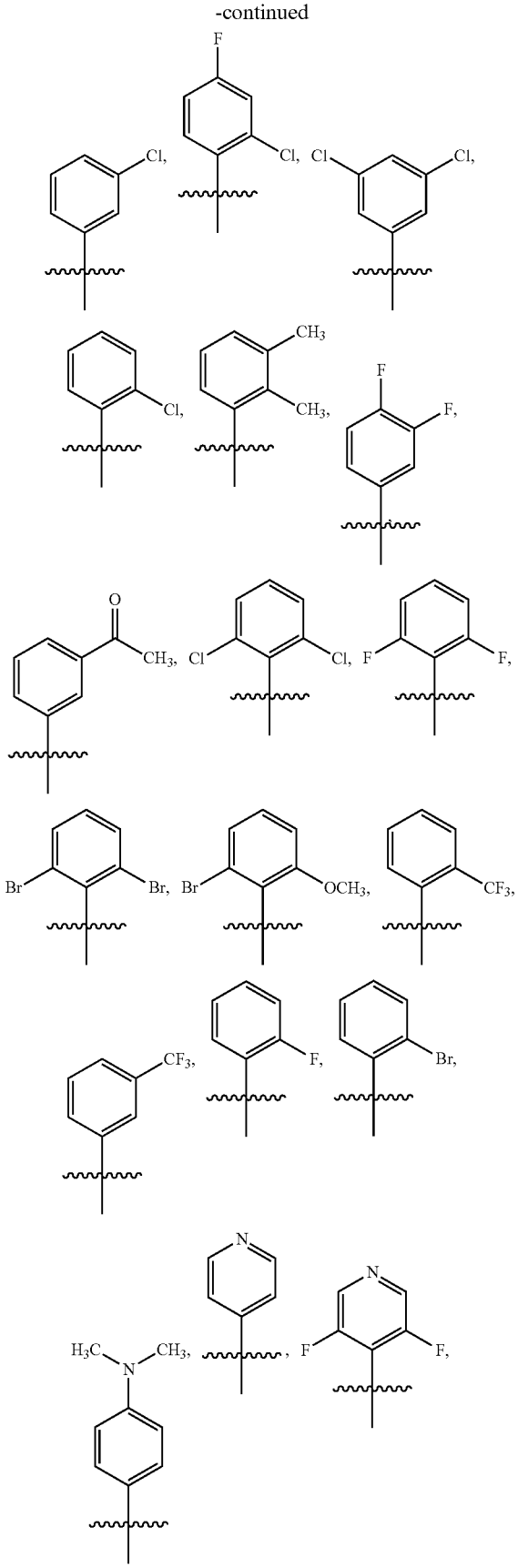
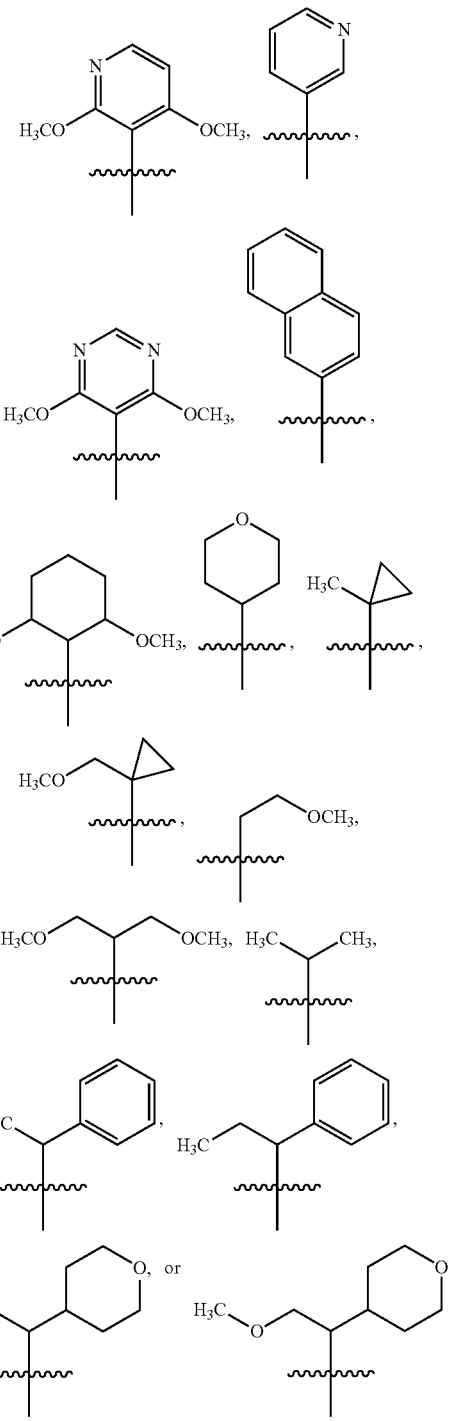
wherein the symbol ⌇⌇⌇, when drawn across a bond, indicates the point of attachment to the rest of the molecule.
61. The compound of any one of embodiments 1-55 or the pharmaceutically acceptable salt thereof, the stereoisomer of any of the foregoing, or the mixture thereof, wherein $R^4$ is selected from

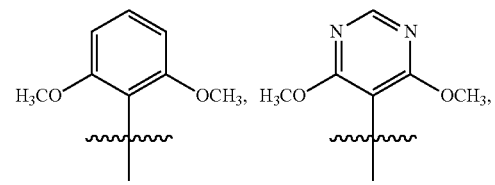

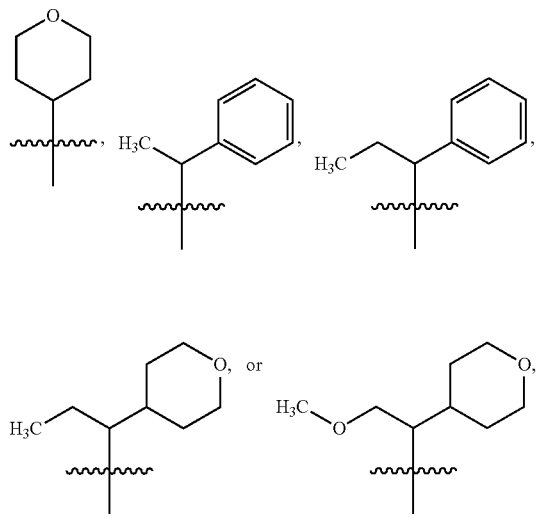

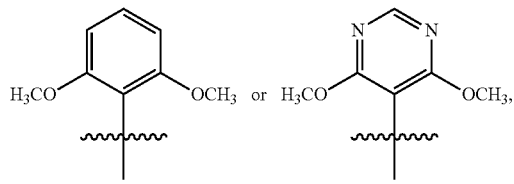 [SMILES: *c1c(OC)cccc1OC ; *c1c(OC)ncnc1OC]

wherein the symbol ⌇, when drawn across a bond, indicates the point of attachment to the rest of the molecule.

62. The compound of any one of embodiments 1-55 or the pharmaceutically acceptable salt thereof, the stereoisomer of any of the foregoing, or the mixture thereof, wherein R⁴ is selected from

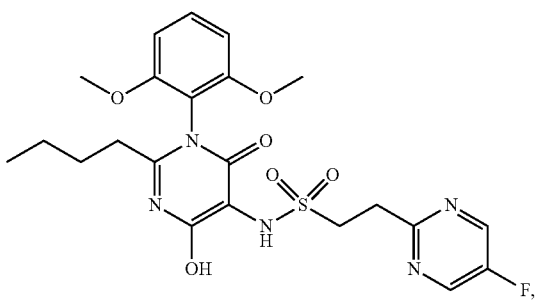

wherein the symbol ⌇, when drawn across a bond, indicates the point of attachment to the rest of the molecule.

63. The compound of any one of embodiments 1-55 or the pharmaceutically acceptable salt thereof, the tautomer thereof, the pharmaceutically acceptable salt of the tautomer, the stereoisomer of any of the foregoing, or the mixture thereof, wherein R⁴ is a phenyl or pyrimidinyl substituted with 1 or 2 R$^{4a}$ substituents.

64. The compound of embodiment 63 or the pharmaceutically acceptable salt thereof, the tautomer thereof, the pharmaceutically acceptable salt of the tautomer, the stereoisomer of any of the foregoing, or the mixture thereof, wherein the R$^{4a}$ substituents are —O—(C₁-C₂ alkyl) groups.

65. The compound of embodiment 1, wherein the compound is selected from

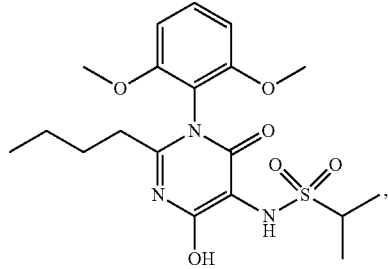

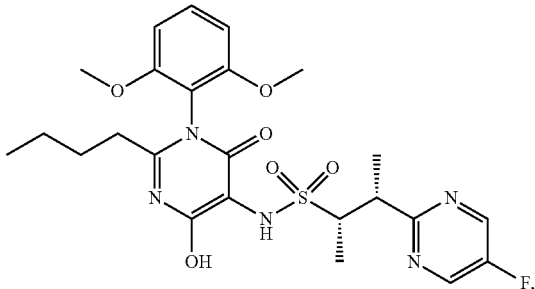

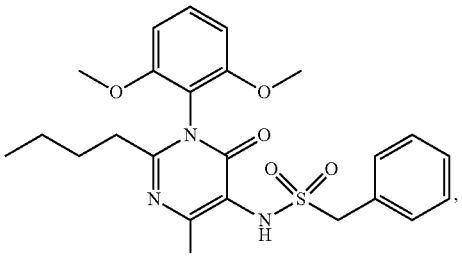

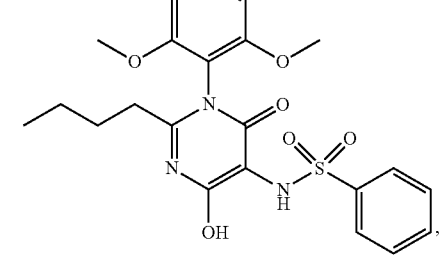

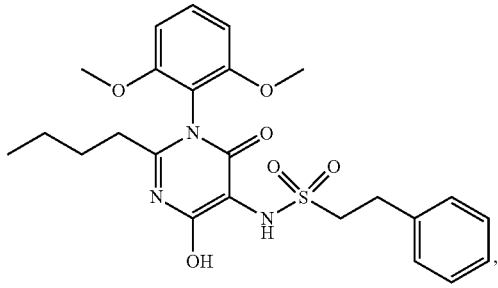

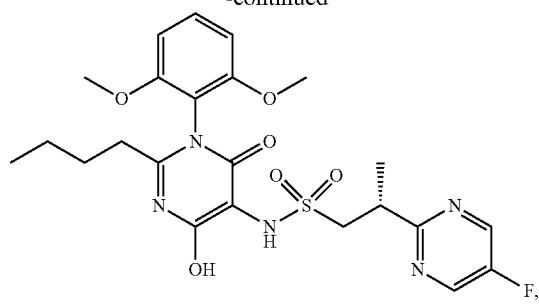
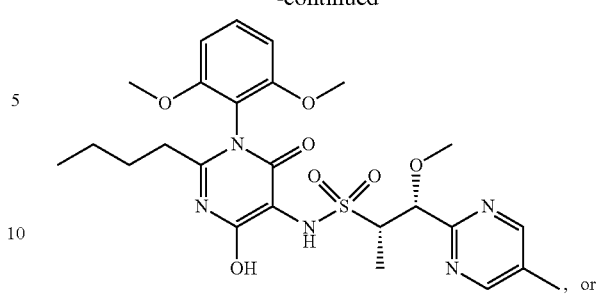
, or
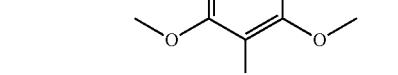
or
the pharmaceutically acceptable salt thereof, or the mixture thereof.
66. The compound of embodiment 1, wherein the compound is selected from
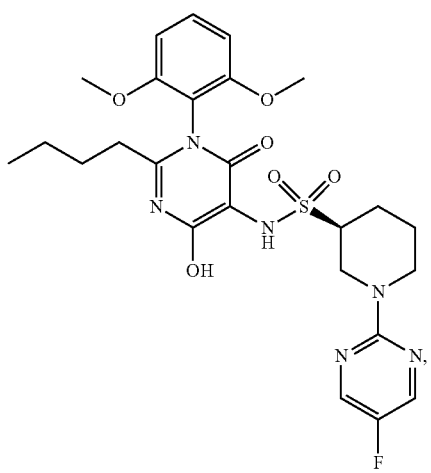
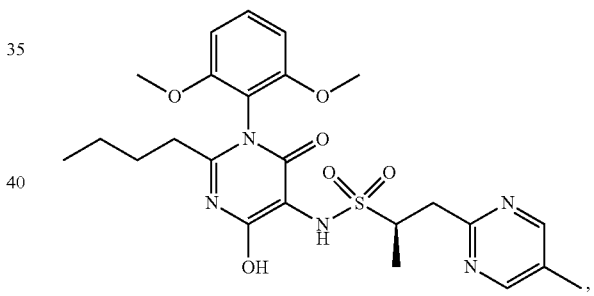
,
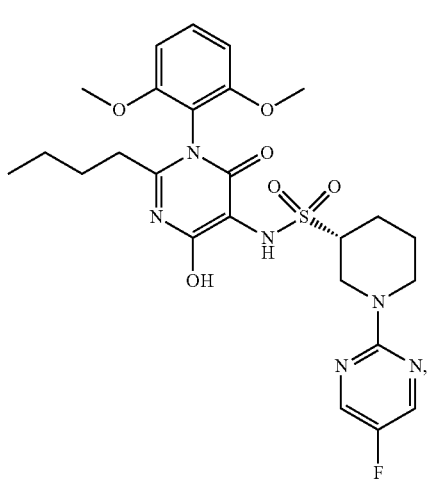
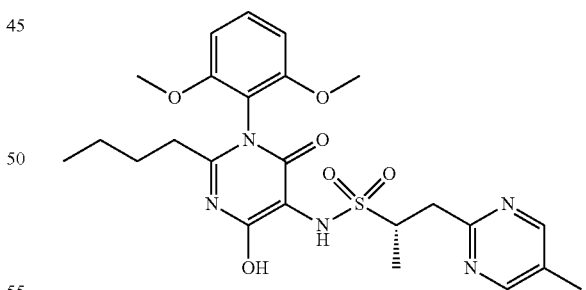
,
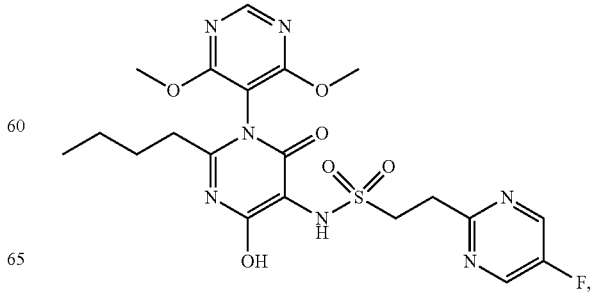
, 53
-continued
54
-continued
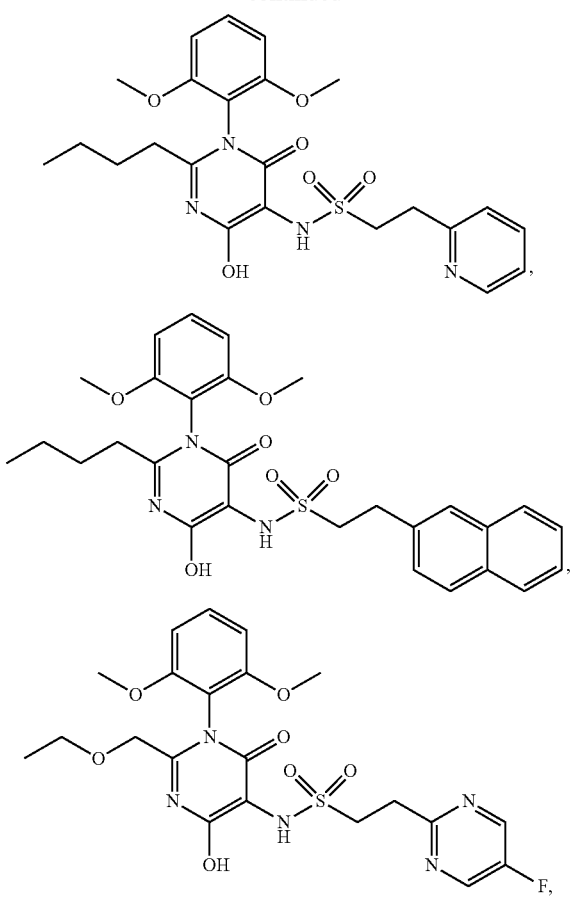
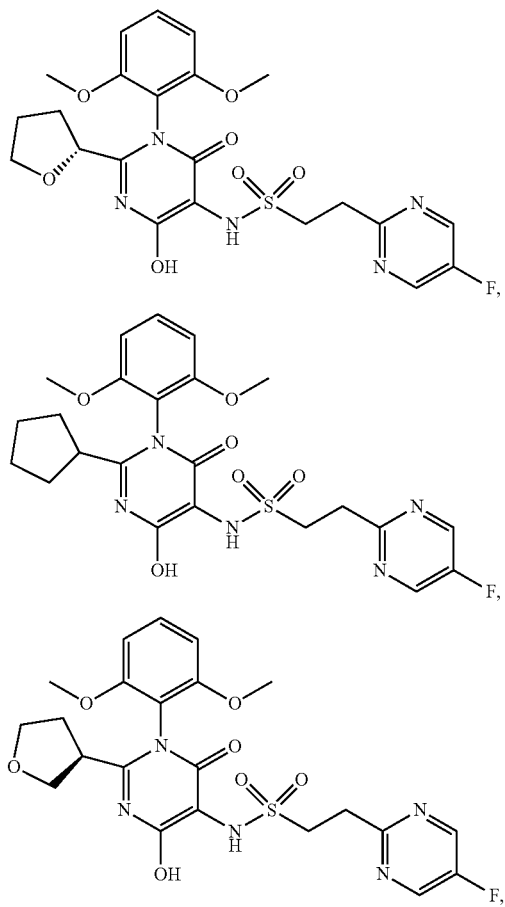
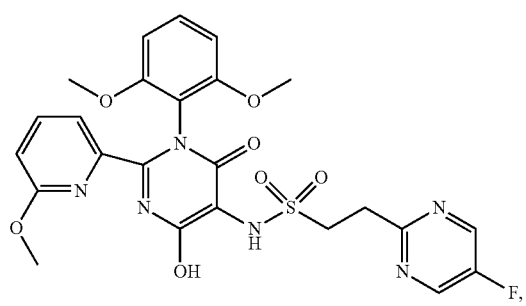
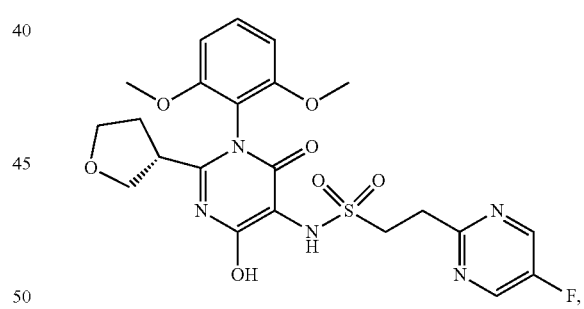
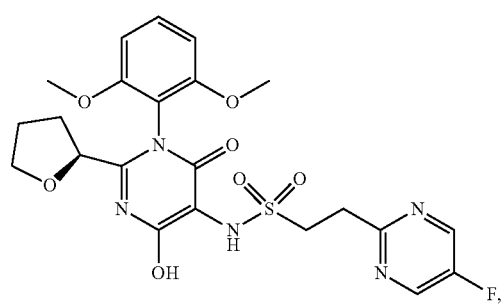
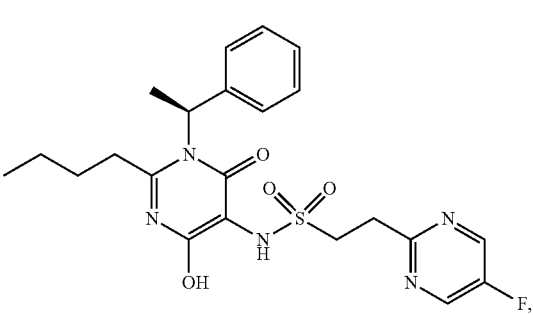

55
-continued
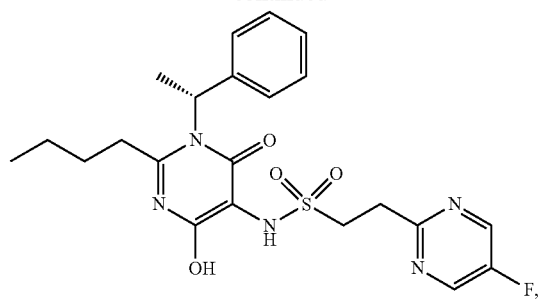
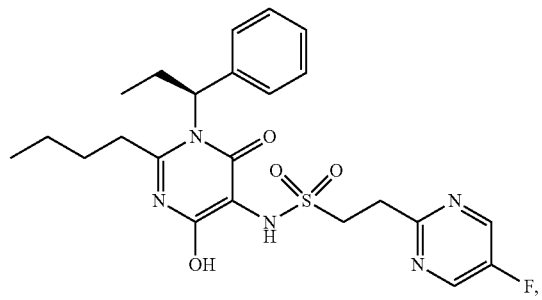
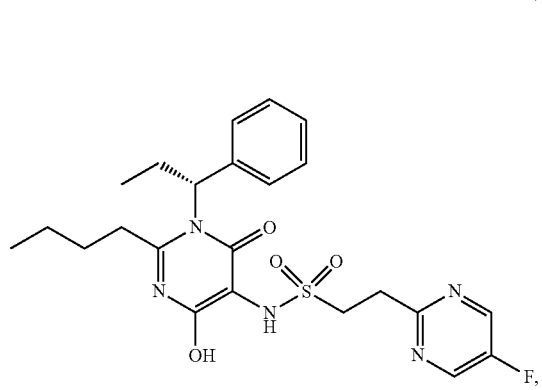
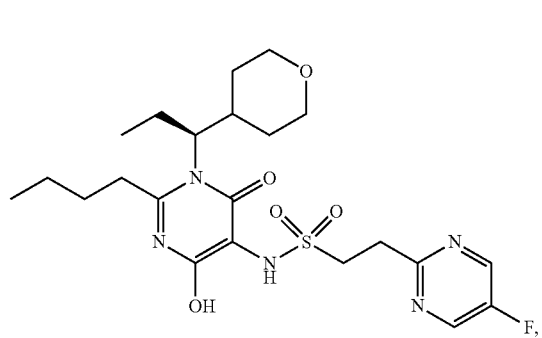
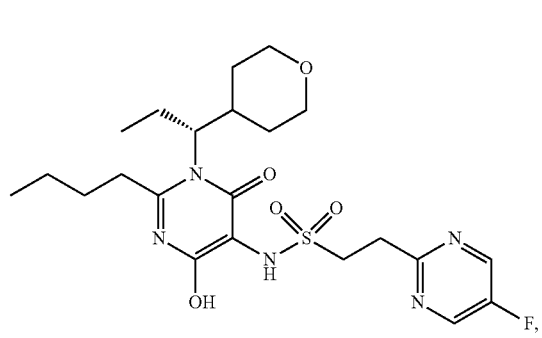
56
-continued
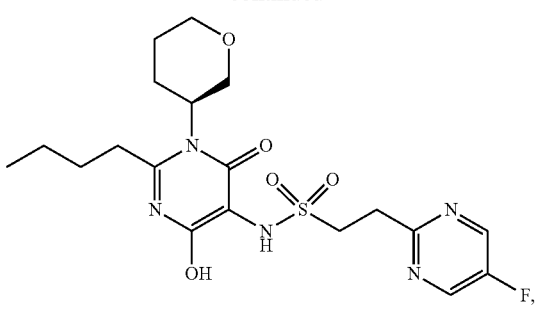
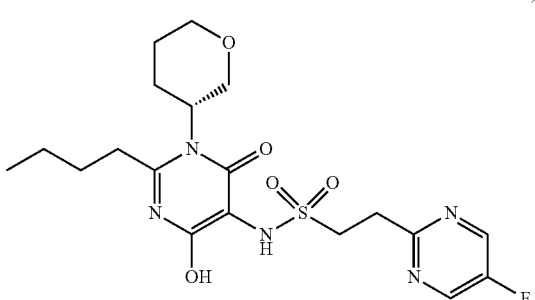
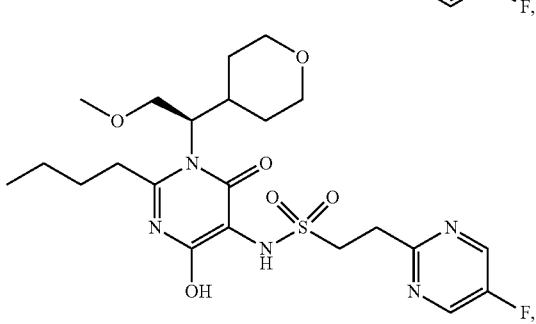
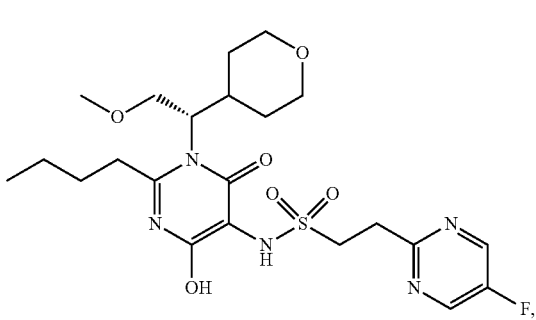
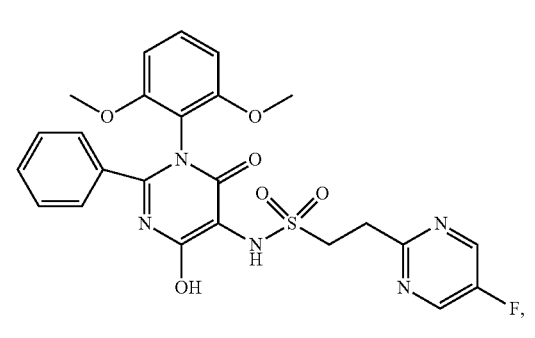

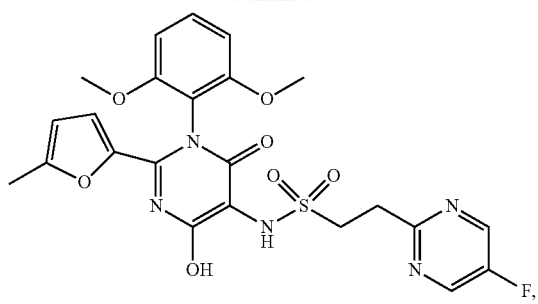

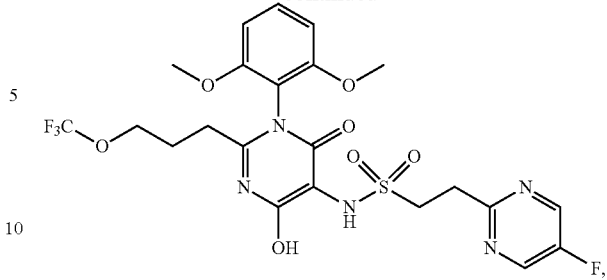

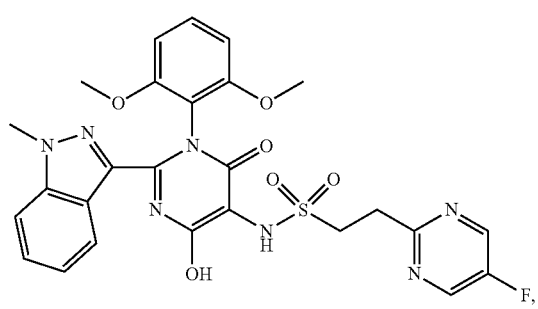

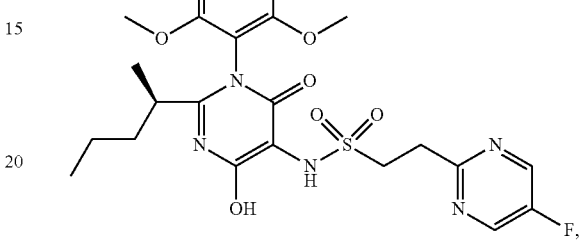

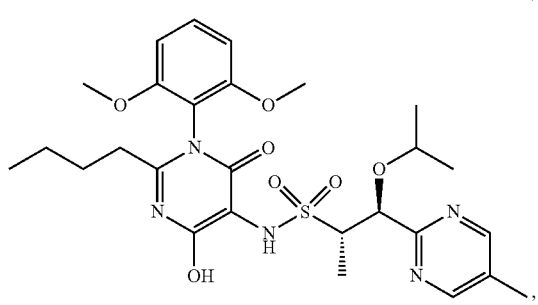

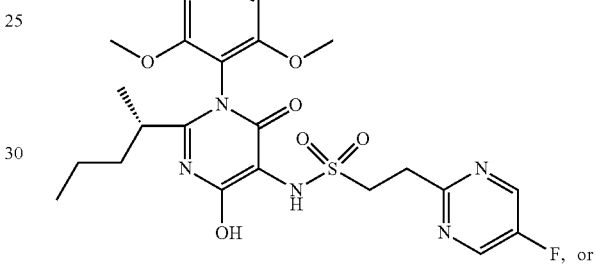

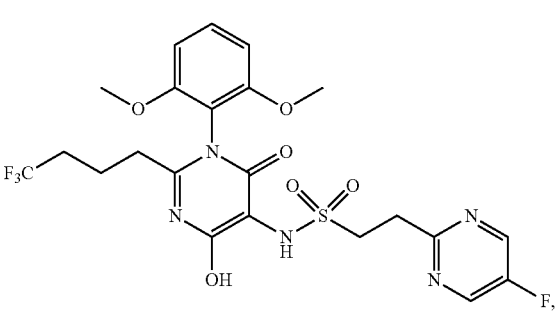

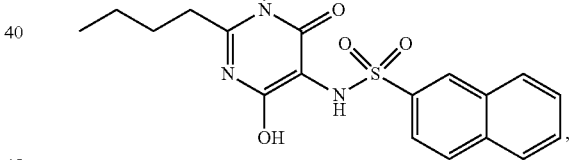

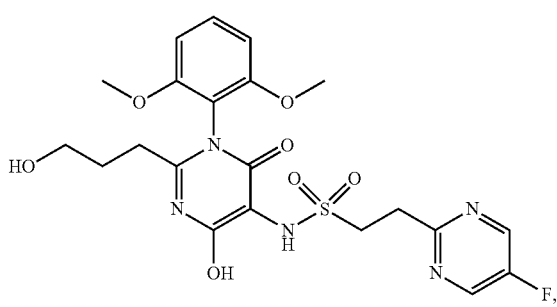

or the pharmaceutically acceptable salt thereof, or the mixture thereof.

67. A pharmaceutical composition, comprising the compound of any one of embodiments 1-66 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

68. A pharmaceutical composition, comprising the compound of any one of embodiments 1-68 or the pharmaceutically acceptable salt thereof and at least one pharmaceutically acceptable excipient.

69. The pharmaceutical composition of embodiment 67 or embodiment 68, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

70. The pharmaceutical composition of embodiment 67 or embodiment 68, further comprising a therapeutic agent selected from an angiotensin converting enzyme (ACE) inhibitor or an angiotensin-receptor blocker (ARB).

71. A method of treating a cardiovascular condition, the method comprising: administering to a subject an effective amount of the compound of any one of embodiments 1-66 or the pharmaceutically acceptable salt thereof, the stereoisomer of any of the foregoing, or the mixture thereof.

72. The method of embodiment 71, wherein the cardiovascular condition is heart failure.

73. The method of embodiment 71, wherein the cardiovascular condition is heart failure with reduced ejection fraction.

74. The method of embodiment 71, wherein the cardiovascular condition is heart failure with preserved ejection fraction.

75. The method of embodiment 71, wherein the cardiovascular condition is chronic systolic heart failure or chronic diastolic heart failure.

76. The method of embodiment 71, wherein the cardiovascular condition is acute heart failure.

77. The method of embodiment 71, wherein the cardiovascular condition is hypertension.

78. A method of improving cardiac contractility in a subject suffering from a cardiovascular condition, the method comprising: administering to the subject an effective amount of the compound of any one of embodiments 1-66 or the pharmaceutically acceptable salt thereof, the stereoisomer of any of the foregoing, or the mixture thereof, wherein cardiac contractility is improved in the subject after administration.

79. A method of increasing ejection fraction in a subject suffering from a cardiovascular condition, the method comprising: administering to the subject an effective amount of the compound of any one of embodiments 1-66 or the pharmaceutically acceptable salt thereof, the stereoisomer of any of the foregoing, or the mixture thereof, wherein the ejection fraction is increased in the subject after administration.

80. A method of beating a condition in a subject where it is desired to activate the APJ Receptor, the method comprising: administering to the subject an effective amount of the compound of any one of embodiments 1-66 or the pharmaceutically acceptable salt thereof, the stereoisomer of any of the foregoing, or the mixture.

81. The method of embodiment 80, wherein the condition is obesity or diabetes.

82. The method of embodiment 80, wherein the condition is diabetic nephropathy or chronic kidney disease.

83. The method of any one of embodiments 71-82, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

84. The method of any one of embodiments 71-82, wherein the method includes administering at least one additional therapeutic agent to the subject, wherein the additional therapeutic agent is selected from an angiotensin converting enzyme (ACE) inhibitor or an angiotensin-receptor blocker (ARB).

85. A compound of any one of embodiments 1-66 or the pharmaceutically acceptable salt thereof, the stereoisomer of any of the foregoing, or the mixture thereof for use in treating a cardiovascular condition.

86. The compound of embodiments 85, wherein the cardiovascular condition is heart failure.

87. The compound of embodiment 85, wherein the cardiovascular condition is heart failure with reduced ejection fraction.

88. The compound of embodiment 85, wherein the cardiovascular condition is heart failure with preserved ejection fraction.

89. The compound of embodiment 85, wherein the cardiovascular condition is chronic systolic heart failure or chronic diastolic heart failure.

90. The compound of embodiment 85, wherein the cardiovascular condition is acute heart failure.

91. The compound of embodiment 85, wherein the cardiovascular condition is hypertension.

92. A compound of any one of embodiments 1-66 or the pharmaceutically acceptable salt thereof, the stereoisomer of any of the foregoing, or the mixture thereof for use in activating the APJ Receptor or for treating a condition where it is desirable to activate the APJ Receptor.

93. The compound of embodiment 92, wherein the condition is obesity or diabetes.

94. The compound of embodiment 92, wherein the condition is diabetic nephropathy or chronic kidney disease.

95. A use of the compound of any one of embodiments 1-66 or the pharmaceutically acceptable salt thereof, the stereoisomer of any of the foregoing, or the mixture thereof in the preparation of a medicament for treating a cardiovascular condition.

96. The use of embodiment 95, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

97. The use of embodiment 95, further comprising a therapeutic agent selected from an angiotensin converting enzyme (ACE) inhibitor or an angiotensin-receptor blocker (ARB).

98. The use of the compound of any one of embodiments 95-97, wherein the cardiovascular condition is heart failure.

99. The use of the compound of any one of embodiments 95-97, wherein the cardiovascular condition is heart failure with reduced ejection fraction.

100. The use of the compound of any one of embodiments 95-97, wherein the cardiovascular condition is heart failure with preserved ejection fraction.

101. The use of the compound of any one of embodiments 95-97, wherein the cardiovascular condition is chronic systolic heart failure or chronic diastolic heart failure.

102. The use of the compound of any one of embodiments 95-97, wherein the cardiovascular condition is acute heart failure.

103. The use of the compound of any one of embodiments 95-97, wherein the cardiovascular condition is hypertension.

104. A use of the compound of any one of embodiments 1-66 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

105. The use of embodiment 104, wherein the condition is obesity or diabetes.

106. The use of embodiment 104, wherein the condition is diabetic nephropathy or chronic kidney disease.

107. A treatment regimen for a cardiovascular disease, the regimen comprising: the compound of any one of embodiments 1-66 or the pharmaceutically acceptable salt thereof, the stereoisomer of any of the foregoing, or the mixture thereof.

108. The treatment regimen of embodiment 107, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

109. The treatment regimen of embodiment 107, wherein the regimen further comprises a therapeutic agent selected from an angiotensin converting enzyme (ACE) inhibitor or an angiotensin-receptor blocker (ARB).

110. A kit, the kit comprising: the compound of any one of embodiments 1-66 or the pharmaceutically acceptable salt thereof, the stereoisomer of any of the foregoing, or the mixture thereof.

111. The kit of embodiment 110, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

112. The kit of embodiment 110, wherein the kit further comprises a therapeutic agent selected from an angiotensin converting enzyme (ACE) inhibitor or an angiotensin-receptor blocker (ARB).

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to beat a number of diseases and disorders. Thus, in some embodiments, the invention provides a method of beating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, edema, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for beating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for beating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes. In other embodiments, the condition is cardiac wasting.

The compounds of the invention may find utility in treating a number of other conditions. For example, the compounds of the invention may find utility in treating patients with conditions related to renal perfusion, hyperglycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activating stem cells and progenitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6×150 mm, 5 micron, 5 to 100% ACN in $H_2O$ with 0.1% TFA for 15 min at 1.5 mL/min; System B: Zorbax SB-C8, 4.6×75 mm, 10 to 90% ACN in $H_2O$ with 0.1% formic acid for 12 min at 1.0 mL/min). Silica gel chromatography was generally performed with prepacked silica gel cartridges (Biotage or Teledyne-Isco). $^1$H NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 µL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

A wide variety of sulfonamide tails and $R^4$ groups can be used to synthesize compounds of the invention such as those set forth in WO 2016/187308 and U.S. Pat. Appl. Pub. No. US 2016/0340336 which are hereby incorporated by reference in their entireties and for all purposes as if specifically set forth herein. Thus, compounds of the present invention may be prepared using any of the $R^3$, $R^4$, and Q groups taught in WO 2016/187308 and U.S. Pat. Appl. Pub. No. US 2016/0340336.

The following Abbreviations are used to refer to various reagents and solvents:
d day or days
DCM Dichloromethane
DMF N,N-Dimethylformamide
DMSO Dimethylsulfoxide
EtOAc Ethyl Acetate
EtOH Ethanol
h hour or horns
IPA Isopropanol
min minute or minutes
MeOH Methanol
MS Mass spectrum
RT Room temperature
SFC Supercritical fluid chromatography
TEA Triethylamine
TFA Trifluoroacetic acid
THF Tetrahydrofuran
TFC Thin Layer Chromatography Example 4.0. Preparation of N-(2-butyl-1-(2,6-dimethoxyphenyl)-4-hydroxy-6-oxo-1,6-dihydropyrimidin-5-yl)-2-(5-fluoropyrimidin-2-yl)ethane-1-sulfonamide N-(2,6-Dimethoxyphenyl)pentanimidamide, Intermediate 1.0. A solution of 2,6-dimethoxyaniline (60.0 g, 392.0 mmol) and pentanenitrile (130.0 g, 1567.0 mmol) in toluene (1560.0 mL) was cooled to 0° C. under an atmosphere of nitrogen. Trimethylaluminum (392.0 mL, 784.0 mmol) was then added dropwise over 30 min and the internal temperature was maintained at 0° C. The reaction mixture was warmed to RT and heated to 110° C. After 16 h, the mixture was cooled to −10° C. and quenched with careful addition of a saturated aqueous solution of Rochelle's salt (1.0 L) over 30 min. The layers were separated and the aqueous layer was extracted with EtOAc (2×500 mL). The combined organic layer was washed with brine (500 mL), dried over anhydrous sodium sulphate, filtered and concentrated under reduced pressure. Purification by column chromatography (silica gel (60-120 mesh) column, eluting with 5 to 10% MeOH in DCM with added 0.5% TEA) gave Intermediate 1.0 (70.0 g, 296.0 mmol). $^1$H NMR (400 MHz, CDCl$_3$) δ 7.04 (t, J=8.3 Hz, 1H), 6.60 (d, J=8.3 Hz, 2H), 4.65 (bs, 2H), 3.80 (m, 6H), 2.47-2.24 (m, 2H), 1.70-1.59 (m, 2H), 1.50-1.29 (m, 2H), 0.95 (dd, J=6.8 Hz, 3H). LCMS-ESI (pos.) m/z: 237.2 (M+H)⁺.

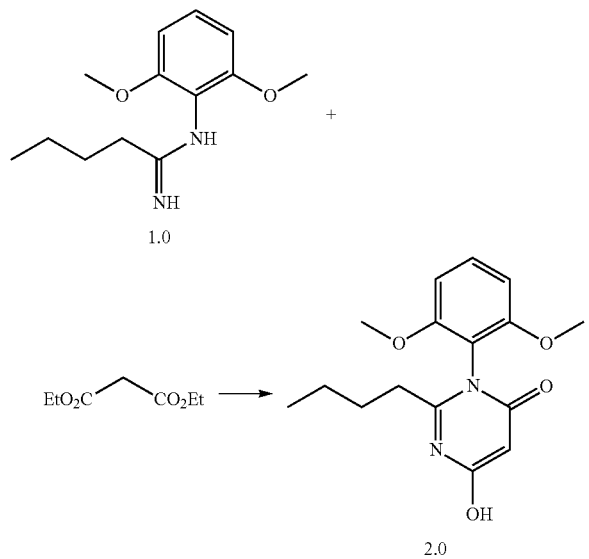 [SMILES: CCCCC(=N)Nc1c(OC)cccc1OC ; CCOC(=O)CC(=O)OCC ; CCCCc1nc(O)cc(=O)n1-c1c(OC)cccc1OC]

2-Butyl-3-(2,6-dimethoxyphenyl)-6-hydroxypyrimidin-4(3H)-one, Intermediate 2.0. A solution of Intermediate 1.0 (80.0 g, 338.5 mmol) and diethyl malonate (516.0 mL, 3385.0 mmol) in 1-butanol (1.2 L) was stirred at 0° C. under an atmosphere of nitrogen. Sodium hydride (60% dispersion in oil, 135.0 g, 3385.0 mmol) was added portionwise over 90 min to maintain an internal temperature of 0° C. The reaction mixture was warmed to RT and then heated to 100° C. After 16 h, the reaction mixture was cooled to 0° C. and quenched with addition water (1.0 L) and the resulting solution was concentrated under reduced pressure. The aqueous layer was acidified with aqueous 1.5N HCl and extracted with EtOAc (2×1.0 L). The combined organic layers were washed with brine (500 mL), dried over anhydrous sodium sulphate, filtered and concentrated under reduced pressure. The residue was diluted with EtOAc (200 mL) and stirred for 15 mins. The resulting white precipitate was collected by vacuum filtration and dried under vacuum to provide Intermediate 2.0 (48.0 g, 158.0 mmol0, 47% yield). ¹H NMR (400 MHz, DMSO-d₆) δ 11.39 (bs, 1H), 7.44 (t, J=8.5 Hz, 1H), 6.82 (dd, J=8.6, 3.2 Hz, 2H), 5.25 (s, 1H), 3.74 (m, 6H), 2.17 (t, J=7.5 Hz, 2H), 1.58-1.24 (m, 2H), 1.15 (h, J=7.5 Hz, 2H), 0.71 (t, J=7.3 Hz, 3H). LCMS-ESI (pos.) m/z: 305.2 (M+H)⁺.

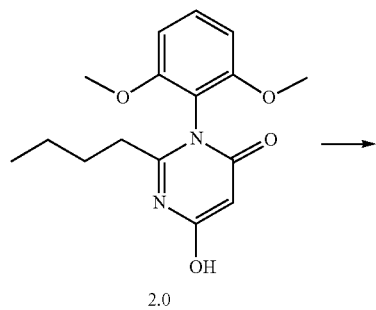

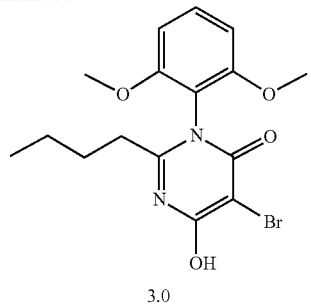

5-Bromo-2-butyl-3-(2,6-dimethoxyphenyl)-6-hydroxypyrimidin-4(3H)-one, Intermediate 3.0. To a solution of Intermediate 2.0 (48.0 g, 158.0 mmol) in DCM (480.0 mL) at 0° C., was added N-bromosuccinimide (28.1 g, 158.0 mmol) portionwise. The reaction mixture was warmed to RT and stirred. After 2 h, the reaction mixture was diluted with water (150 mL) and the layers were separated. The organic layer was washed with brine (150 mL), dried over anhydrous sodium sulphate, filtered and concentrated under reduced pressure. Purification by column chromatography (silica gel (60-120 mesh), eluting 0-10% MeOH in DCM) provided Intermediate 3.0 (48.0 g, 125.0 mmol, 79% yield). ¹H NMR (400 MHz, DMSO-d₆) δ 12.66 (s, 1H), 7.48 (t, J=8.5 Hz, 1H), 6.85 (d, J=8.5 Hz, 2H), 3.76 (m, 6H), 2.31-2.11 (m, 2H), 1.56-1.34 (m, 2H), 1.15 (h, J=13 Hz, 2H), 0.71 (t, J=7.3 Hz, 3H). LCMS-ESI (pos.) m/z: 383.0 (M+H)⁺.

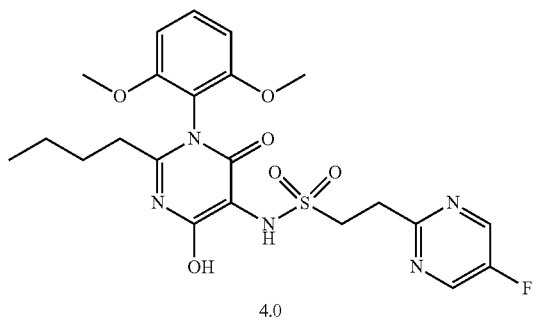 [SMILES: CCCCc1nc(O)c(NS(=O)(=O)CCc2ncc(F)cn2)c(=O)n1-c1c(OC)cccc1OC]

N-(2-Butyl-1-(2,6-dimethoxyphenyl)-4-hydroxy-6-oxo-1,6-dihydropyrimidin-5-yl)-2-(5-fluoropyrimidin-2-yl)ethane-1-sulfonamide, Example 4.0. A vial containing Intermediate 5.0 (127 mg, 0.619 mmol), Intermediate 3.0 (356 mg, 0.930 mmol), copper (I) iodide (66.4 mg, 0.349 mmol), (1R,2R)-(−)-N,N"-dimethylcyclohexane-1,2-diamine (0.200 mL, 1.27 mmol), and cesium carbonate (612 mg, 1.88 mmol) was degassed and backfilled with nitrogen (three times). Anhydrous 1,4-dioxane (2.5 mL) was added and the mixture was stirred at 80° C. After 16 h, the reaction was cooled to RT and diluted with water. The mixture was neutralized by dropwise addition of aqueous 1N HCl (pH ~7). The mixture was extracted with DCM (4×) and the organic layers were combined and washed with 1M sodium thiosulfate (1×). The organic layer was dried over anhydrous magnesium sulfate, filtered and concentrated under reduced pressure. Purification by column chromatography (silica gel, eluting 0-25% 3:1 EtOAc: EtOH in DCM) gave the desired product that was further purified by preparative SFC method (Column: Chiralpak IC (2×25 cm), Mobile Phase: 60:40 (A:B) A: Liquid CO₂, B: MeOH, Flow Rate: 80 mL/min, 2H), 1.23-1.10 (m, J=7.3 Hz, 2H), 0.70 (t, J=7.3 Hz, 3H). LCMS-ESI (pos.) m/z: 508.1 (M+H)$^+$.

The compounds set forth in the following table were synthesized following the procedure described in Example 4.0 using the known starting material as described.

220 nm, 100 bar inlet pressure) to yield Example 4.0. $^1$H NMR (400 MHz, DMSO-d$_6$) δ 12.16-11.67 (m, 1H), 8.80 (d, J=0.8 Hz, 2H), 8.38 (br s, 1H), 7.44 (t, J=8.4 Hz, 1H), 6.83 (d, J=8.5 Hz, 2H), 3.73 (m, 6H), 3.61-3.55 (m, 2H), 3.42-3.36 (m, 2H), 2.19 (t, J=7.7 Hz, 2H), 1.43 (quin, J=7.5 Hz,

TABLE 1

| Example | Reagents | Structure, Name and Data |
|---|---|---|
| 4.1 | 5-bromo-2-butyl-3-(2,6-dimethoxyphenyl)-6-hydroxypyrimidin-4(3H)-one (Intermediate 3.0), isopropylsulfonamide (Nanjing King-Pharm Co., Ltd). Purification was performed by flash chromatography (0-25% 3:1 EtOAc:EtOH in DCM) followed by preparative SFC method (Column: Regis Whelk-O s,s IC (2 × 25 cm), Mobile Phase: 70:30 (A:B) A: Liquid CO$_2$, B: MeOH, Flow Rate: 80 mL/min, 220 nm, 100 bar inlet pressure). The resulting solid was then triturated from MeOH. | 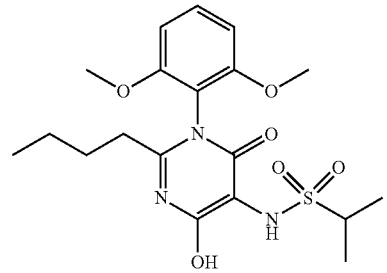 [SMILES: CCCCc1nc(O)c(NS(=O)(=O)C(C)C)c(=O)n1-c1c(OC)cccc1OC]<br>N-(2-butyl-1-(2,6-dimethoxyphenyl)-4-hydroxy-6-oxo-1,6-dihydropyrimidin-5-yl)propane-2-sulfonamide.<br>$^1$H NMR (500 MHz, DMSO-d$_6$) δ 12.02-11.35 (m, 1H), 8.21-7.91 (m, 1H), 7.45 (t, J = 8.4 Hz, 1H), 6.84 (d, J = 8.6 Hz, 2H), 3.74 (s, 6H), 3.30-3.27 (m, 1H), 2.19 (br t, J = 7.7 Hz, 2H), 1.43 (quin, J = 7.5 Hz, 2H), 1.30-1.23 (m, J = 6.7 Hz, 6H), 1.23-1.10 (m, J = 7.4 Hz, 2H), 0.71 (t, J = 7.4 Hz, 3H). LCMS-ESI (pos.) m/z: 426.2 (M + H)$^+$. |
| 4.2 | 5-bromo-2-butyl-3(2,6-dimethoxyphenyl)-6-hydroxypyrimidin-4(3H)-one (Intermediate 3.0) (2S,3R)-3-(5-fluoropyrimidin-2-yl)butane-2-sulfonamide (Intermediate 5.1). Purification was performed by flash chromatography (0-30% 3:1 EtOAc:EtOH in DCM) followed by preparative HPLC: 50 u Silica Gel 19 × 100 mm + XSelect CSH Prep C18 10 u ODB 19 × 100 mm, A: Water 0.1% formic acid B: ACN 0.1% formic acid, Gradient: 20% (2 min), 20-70% (12 min), Flow Rate: 40 mL/min, monitored @ 215 nm. | 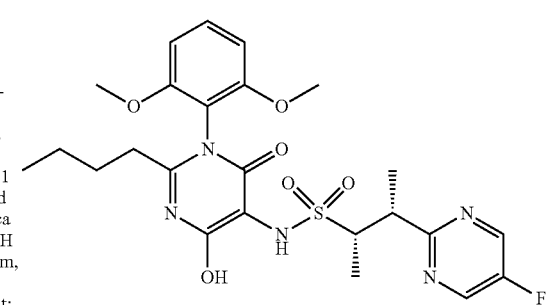<br>(2S,3R)-N-(2-butyl-1-(2,6-dimethoxyphenyl)-4-hydroxy-6-oxo-1,6-dihydropyrimidin-5-yl)-3-(5-fluoropyrimidin-2-yl)butane-2-sulfonamide.<br>$^1$H NMR (500 MHz, DMSO-d$_6$) δ 11.78 (br s, 1H), 8.80 (d, J = 0.8 Hz, 2H), 8.12 (br s, 1H), 7.43 (t, J = 8.4 Hz, 1H), 6.87-6.79 (m, 2H), 3.91-3.84 (m, 1H), 3.80 (dq, J = 4.0, 7.0 Hz, 1H), 3.76-3.68 (m, 6H), 2.16 (br t, J = 7.7 Hz, 2H), 1.43 (td, J = 7.5, 15.2 Hz, 2H), 1.32 (d, J = 7.0 Hz, 3H), 1.27 (d, J = 6.7 Hz, 3H), 1.18-1.10 (m, 2H), 0.70 (t, J = 7.4 Hz, 3H). LCMS-ESI (pos.) m/z: 536.2 (M + H)$^+$. |
| 4.3 | 5-bromo-2-butyl-3-(2,6-dimethoxyphenyl)-6-hydroxypyrimidin-4(3H)-one (Intermediate 3.0), phenylmethanesulfonamide (Frontier Scientific Services Inc). Purification was performed by flash chromatography (5-25% 3:1 EtOAc:EtOH in DCM) followed by preparative HPLC: 50 u Silica Gel 19 × 100 mm + XSelect CSH Prep C18 10 u ODB 19 × 100 mm, A: Water 0.1% formic acid B: ACN 0.1% formic acid, Gradient: 20% (2 min), 20-70% (12 min), Flow Rate: 40 mL/min, monitored @ 215 nm. | 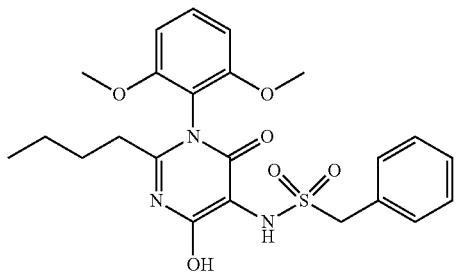 [SMILES: CCCCc1nc(O)c(NS(=O)(=O)Cc2ccccc2)c(=O)n1-c1c(OC)cccc1OC]<br>N-(2-butyl-1-(2,6-dimethoxyphenyl)-4-hydroxy-6-oxo-1,6-dihydropyrimidin-5-yl)-1-phenylmethanesulfonamidesulfonamide.<br>$^1$H NMR (500 MHz, DMSO-d$_6$) δ 11.99 (br s, |

TABLE 1-continued

| Example | Reagents | Structure, Name and Data |
|---|---|---|
| | | 1H), 8.20 (br s, 1H), 7.50-7.39 (m, 3H), 7.37-7.29 (m, 3H), 6.86 (d, J = 8.3 Hz, 2H), 4.44 (s, 2H), 3.83-3.74 (m, 6H), 2.23 (t, J = 7.7 Hz, 2H), 1.46 (quin, J = 7.5 Hz, 2H), 1.22-1.12 (m, 2H), 0.72 (t, J = 7.4 Hz, 3H). LCMS-ESI (pos.) m/z: 474.2 (M + H)+. |
| 4.4a | 5-bromo-2-butyl-3-(2,6-dimethoxyphenyl)-6-hydroxypyrimidin-4(3H)-one (Intermediate 3.0), benzenesulfonamide (Acros Organics). Purification was performed using the method described in Example 4.3. | 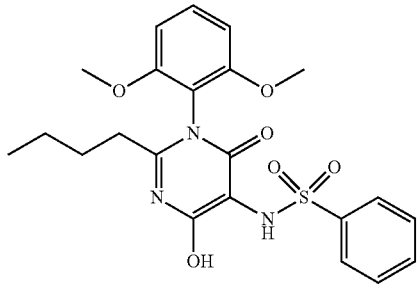 [SMILES: CCCCc1nc(O)c(NS(=O)(=O)c2ccccc2)c(=O)n1-c1c(OC)cccc1OC]<br>N-(2-butyl-1-(2,6-dimethoxyphenyl)-4-hydroxy-6-oxo-1,6-dihydropyrimidin-5-yl)benzenesulfonamide.<br>¹H NMR (500 MHz, DMSO-d₆) δ 11.71 (br s, 1H), 8.63 (br s, 1H), 7.83-7.78 (m, 2H), 7.54-7.48 (m, 1H), 7.47-7.39 (m, 3H), 6.80 (d, J = 8.6 Hz, 2H), 3.75-3.69 (m, 6H), 2.15 (t, J = 7.7 Hz, 2H), 1.42 (quin, J = 7.5 Hz, 2H), 1.18-1.10 (m, 2H), 0.70 (t, J = 7.4 Hz, 3H). LCMS-ESI (pos.) m/z: 460.1 (M + H)+. |
| 4.4b | 5-bromo-2-butyl-3-(2,6-dimethoxyphenyl)-6-hydroxypyrimidin-4(3H)-one (Intermediate 3.0), 2-phenylethane-1-sulfonamide (Enamine). Purification was perfomed by flash chromatography (0-20% 3:1 EtOAc:EtOH in DCM). | 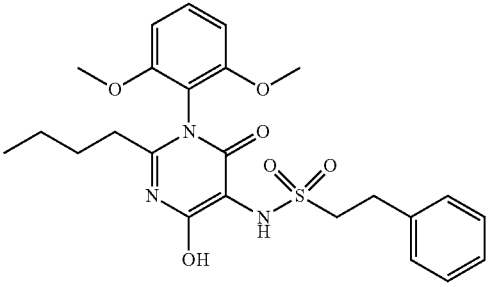 [SMILES: CCCCc1nc(O)c(NS(=O)(=O)CCc2ccccc2)c(=O)n1-c1c(OC)cccc1OC]<br>N-(2-butyl-1-(2,6-dimethoxyphenyl)-4-hydroxy-6-oxo-1,6-dihydropyrimidin-5-yl)-2-phenylethane-1-sulfonamide.<br>¹H NMR (500 MHz, DMSO-d₆) δ 7.46 (t, J = 8.4 Hz, 1H), 7.31-7.16 (m, 5H), 6.84 (d, J = 8.6 Hz, 2H), 3.75-3.68 (m, 6H), 3.34-3.22 (m, 2H), 3.15-3.00 (m, 2H), 2.26-2.14 (m, 2H), 1.45 (quin, J = 7.5 Hz, 2H), 1.16 (qd, J = 7.4, 14.8 Hz, 2H), 0.72 (t, J = 7.3 Hz, 3H), 2 protons not observed. LCMS-ESI (pos.) m/z: 488.0 (M + H)+. |
| 4.5 | 5-bromo-2-butyl-3-(2,6-dimethoxyphenyl)-6-hydroxypyrimidin-4(3H)-one (Intermediate 3.0), (R)-2-(5-fluoropyrimidin-2-yl)propane-1-sulfonamide or (S)-2-(5-fluoropyrimidin-2-yl)propane-1-sulfonamide (Intermediate 5.2). Purification was performed by flash chromatography (0-10% MeOH in DCM) followed by preparative HPLC: 50 u Silica Gel 19 × 100 mm +XSelect CSH Prep C18 10 u ODB 19 × 100 mm, A: Water 0.1% formic acid B: ACN 0.1% formic acid, Gradient: 20% (2 min), 20-70% (12 min), Flow | 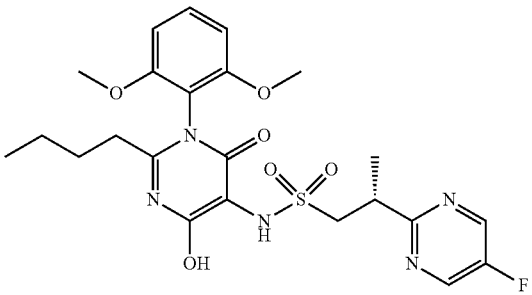 [SMILES: CCCCc1nc(O)c(NS(=O)(=O)C[C@H](C)c2ncc(F)cn2)c(=O)n1-c1c(OC)cccc1OC]<br>or |

| Example | Reagents | Structure, Name and Data |
|---|---|---|
| | Rate: 40 mL/min, monitored @ 215 nm. | 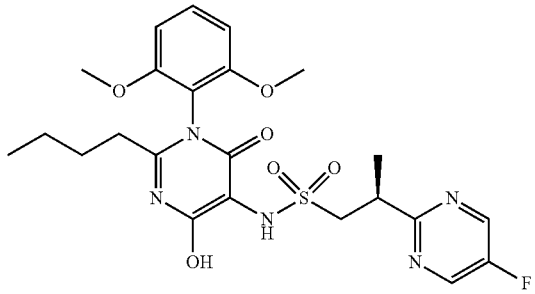 [SMILES: CCCCc1nc(O)c(NS(=O)(=O)C[C@@H](C)c2ncc(F)cn2)c(=O)n1-c1c(OC)cccc1OC]

(R)-N-(2-butyl-1-(2,6-dimethoxyphenyl)-4-hydroxy-6-oxo-1,6-dihydropyrimidin-5-yl)-2-(5-fluoropyrimidin-2-yl)propane-1-sulfonamide or (S)-N-(2-butyl-1-(2,6-dimethoxyphenyl)-4-hydroxy-6-oxo-1,6-dihydropyrimidin-5-yl)-2-(5-fluoropyrimidin-2-yl)propane-1-sulfonamide. $^1$H NMR (500 MHz, DMSO-$d_6$) δ 11.85 (br s, 1H), 8.81 (d, J = 0.8 Hz, 2H), 8.28 (br s, 1H), 7.45 (t, J = 8.4 Hz, 1H), 6.84 (d, J = 8.6 Hz, 2H), 3.80-3.75 (m, 4H), 3.75-3.73 (m, 3H), 3.71-3.64 (m, 1H), 3.38 (dd, J = 5.7, 14.0 Hz, 1H), 2.19 (t, J = 7.7 Hz, 2H), 1.44 (quin, J = 7.5 Hz, 2H), 1.30 (d, J = 7.0 Hz, 3H), 1.20-1.11 (m, J = 7.4 Hz, 2H), 0.71 (t, J = 7.4 Hz, 3H). LCMS-ESI (pos.) m/z: 522.2 (M + H)$^+$. |
| 4.6 | 5-bromo-2-butyl-3-(2,6-dimethoxyphenyl)-6-hydroxypyrimidin-4(3H)-one (Intermediate 3.0), (S)-2-(5-fluoropyrimidin-2-yl)propane-1-sulfonamide or (R)-2-(5-fluoropyrimidin-2-yl)propane-1-sulfonamide (Intermediate 5.3). Purification was perfomed by flash chromatography (0-3% MeOH in DCM). | 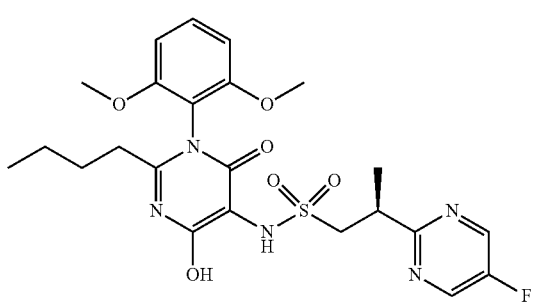 [SMILES: CCCCc1nc(O)c(NS(=O)(=O)C[C@@H](C)c2ncc(F)cn2)c(=O)n1-c1c(OC)cccc1OC]

or

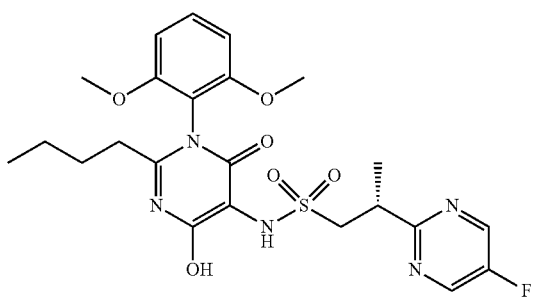 [SMILES: CCCCc1nc(O)c(NS(=O)(=O)C[C@H](C)c2ncc(F)cn2)c(=O)n1-c1c(OC)cccc1OC]

(S)-N-(2-butyl-1-(2,6-dimethoxyphenyl)-4-hydroxy-6-oxo-1,6-dihydropyrimidin-5-yl)-2-(5-fluoropyrimidin-2-yl)propane-1-sulfonamide or (R)-N-(2-butyl-1-(2,6-dimethoxyphenyl)-4-hydroxy-6-oxo-1,6-dihydropyrimidin-5-yl)-2-(5-fluoropyrimidin-2-yl)propane-1-sulfonamide. $^1$H NMR (500 MHz, DMSO-$d_6$) δ = 11.85 (br s, 1H), 8.82 (s, 2H), 8.31 (br s, 1H), 7.46 (t, J = 8.4 Hz, 1H), 6.85 (d, J = 8.3 Hz, 2H), 3.80-3.75 (m, 4H), 3.75 (s, 3H), 3.72-3.63 (m, 1H), 3.39 (dd, J = 5.7, 14.0 Hz, 1H), 2.51 (td, J = 1.8, 3.8 Hz, 2H), 2.26-2.15 (m, 2H), 1.45 (quin, J = 7.5 Hz, 2H), 1.31 (d, J = 7.0 Hz, 3H), 1.20-1.13 (m, J = 7.4 Hz, 2H), 0.72 (t, J = 7.3 Hz, 3H). LCMS-ESI (pos.) m/z: 522.0 (M + H)$^+$. |

TABLE 1-continued

| Example | Reagents | Structure, Name and Data |
|---|---|---|
| 4.7 | 5-bromo-2-butyl-3-(2,6-dimethoxyphenyl)-6-hydroxypyrimidin-4(3H)-one (Intermediate 3.0), (R)-2-(5-fluoropyrimidin-2-yl)propane-1-sulfonamide or (S)-2-(5-fluoropyrimidin-2-yl)propane-1-sulfonamide (Intermediate 5.4). The purification was performed using the method in Example 4.2. | 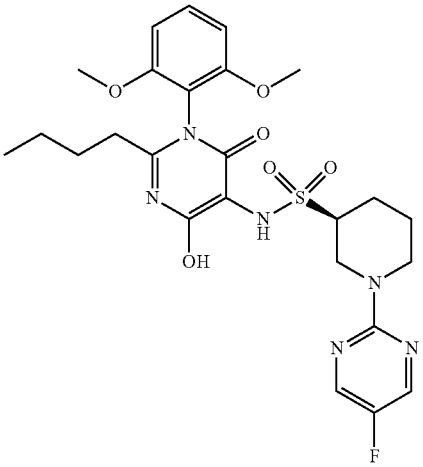 [SMILES: CCCCc1nc(O)c(NS(=O)(=O)[C@H]2CCCN(c3ncc(F)cn3)C2)c(=O)n1-c1c(OC)cccc1OC]<br>or<br>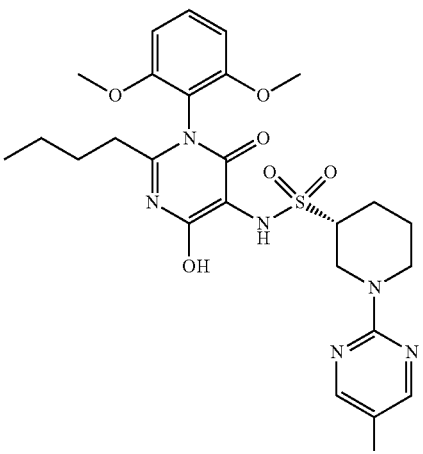<br>(S)-N-(2-butyl-1-(2,6-dimethoxyphenyl)-4-hydroxy-6-oxo-1,6-dihydropyrimidin-5-yl)-1-(5-fluoropyrimidin-2-yl)piperidine-3-sulfonamide or (R)-N-(2-butyl-1-(2,6-dimethoxyphenyl)-4-hydroxy-6-oxo-1,6-dihydropyrimidin-5-yl)-1-(5-fluoropyrimidin-2-yl)piperidine-3-sulfonamide.<br>$^1$H NMR (500 MHz, DMSO-$d_6$) δ 8.43 (s, 2H), 8.32 (br s, 1H), 7.43 (t, J = 8.4 Hz, 1H), 6.82 (dd, J = 2.9, 8.6 Hz, 2H), 4.99-4.94 (m, 1H), 4.50 (br d, J = 12.5 Hz, 1H), 3.71 (s, 3H), 3.65 (s, 3H), 3.20 (tt, J = 3.6, 11.3 Hz, 1H), 3.06-3.00 (m, 1H), 2.84-2.77 (m, 1H), 2.43-2.36 (m, 1H), 2.18 (br t, J = 7.7 Hz, 2H), 1.80-1.68 (m, 2H), 1.43 (quin, J = 7.5 Hz, 2H), 1.38-1.28 (m, 1H), 1.19-1.11 (m, J = 7.4 Hz, 2H), 0.70 (t, J = 7.4 Hz, 3H). LCMS-ESI (pos.) m/z: 563.2 (M + H)$^+$. |

TABLE 1-continued

| Example | Reagents | Structure, Name and Data |
|---|---|---|
| 4.8 | 5-bromo-2-butyl-3-(2,6-dimethoxyphenyl)-6-hydroxypyrimidin-4(3H)-one (Intermediate 3.0), (1R,2S)-1-methoxy-1-(5-methylpyrimidin-2-yl)propane-2-sulfonamide (Intermediate 5.5). The purification was performed using the method in Example 4.5. | 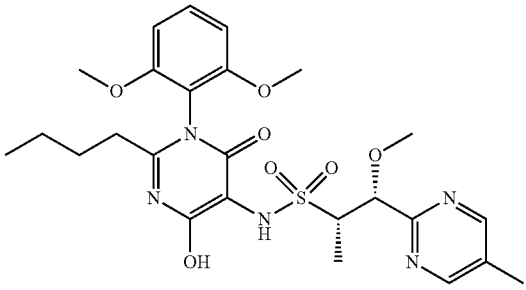 [SMILES: CCCCc1nc(O)c(NS(=O)(=O)[C@@H](C)[C@H](OC)c2ncc(C)cn2)c(=O)n1-c1c(OC)cccc1OC]<br>(1R,2S)-N-(2-butyl-1-(2,6-dimethoxyphenyl)-4-hydroxy-6-oxo-1,6-dihydropyrimidin-5-yl)-1-methoxy-1-(5-methylpyrimidin-2-yl)propane-2-sulfonamide.<br>$^1$H NMR (500 MHz, DMSO-$d_6$) δ 8.65-8.60 (m, 2H), 8.13-7.83 (m, 1H), 7.42 (t, J = 8.4 Hz, 1H), 6.83-6.77 (m, 2H), 4.88 (d, J = 3.1 Hz, 1H), 3.87-3.78 (m, 1H), 3.76-3.70 (m, 7H), 3.23 (s, 3H), 2.26 (s, 3H), 2.14 (br t, J = 7.1 Hz, 2H), 1.46-1.39 (m, 2H), 1.27 (d, J = 7.0 Hz, 3H), 1.18-1.11 (m, 2H), 0.70 (t, J = 7.3 Hz, 3H). LCMS-ESI (pos.) m/z: 548.0 (M + H)$^+$. |
| 4.9 | 5-bromo-2-butyl-3-(2,6-hydroxypyrimidin-4(3H)-one (Intermediate 3.0), cyclohexanesulfonamide (Enamine). Purification was performed by preparative HPLC: XSelect CSH Prep C18 10 um ODB 19 × 100 mm, A: Water 0.1% formic acid B: ACN 0.1% formic acid, gradient. | 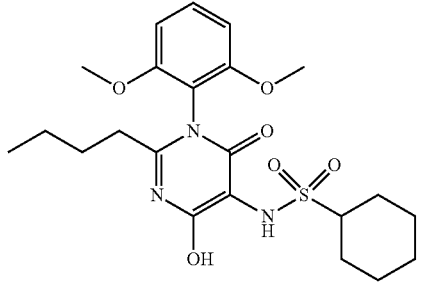 [SMILES: CCCCc1nc(O)c(NS(=O)(=O)C2CCCCC2)c(=O)n1-c1c(OC)cccc1OC]<br>N-(2-butyl-1-(2,6-dimethoxyphenyl)-4-hydroxy-6-oxo-1,6-dihydro-5-pyrimidinyl)cyclohexanesulfonamide.<br>$^1$H NMR (600 MHz, DMSO-$d_6$) δ 7.46 (t, J = 8.49 Hz, 1 H) 6.85 (d, J = 8.56 Hz, 2 H) 3.79-3.73 (m, 6 H) 2.99 (br t, J = 3.15 Hz, 1 H) 2.19 (br d, J = 8.80 Hz, 4 H) 1.75 (br d, J = 10.82 Hz, 2 H) 1.51-1.64 (m, 1 H) 1.38-1.48 (m, 2 H) 1.24-1.37 (m, 2H) 1.07-1.20 (m, 5 H) 0.70 (t, J = 7.32 Hz, 3 H), 2 protons not observed. LCMS-ESI (pos.) m/z: 466.2 (M + H)$^+$. |
| 4.17 | 5-bromo-2-cyclopentyl-3-(2,6-dimethoxyphenyl)-6-hydroxypyrimidin-4(3H)-one was prepared in an analogous to the preparation of Intermediate 3.0 using cyclopentane carbonitrile instead of pentanenitrile, 2-(5-fluoropyrimidin-2-yl)ethanesulfonamide (Intermediate 5.0). The purification was performed using the method in Example 4.2. | 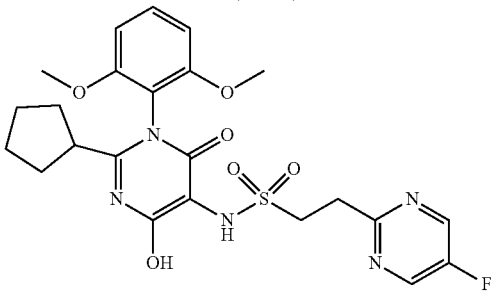<br>N-[2-cyclopentyl-1-(2,6-dimethoxyphenyl)-4-hydroxy-6-oxo-pyrimidin-5-yl]-2-(5-fluoropyrimidin-2-yl)ethanesulfonamide. 1H NMR (600 MHz, DMSO-$d_6$) δ 11.49-11.69 (m, 1 H), 8.79-8.83 (m, 2 H), 8.44 (br s, 1 H), 7.43 (t, J = 8.6 Hz, 1 H), 6.81 (d, J = 8.4 Hz, 2 H), 3.71-3.74 (m, 7 H), 3.56-3.59 (m, 2 H), 3.37-3.41 (m, 2 H), 1.74-1.81 (m, 2 H), 1.62-1.71 (m, 2 H), 1.55-1.61 (m, 2 H), 1.36-1.45 (m, 2 H). LCMS-ESI (pos.) m/z: 520.2 (M + H)$^+$. |

TABLE 1-continued

| Example | Reagents | Structure, Name and Data |
|---|---|---|
| 4.24 | 5-bromo-3-(2,6-dimethoxyphenyl)-6-hydroxy-2-phenylpyrimidin-4(3H)-one was prepared in an analogous to the preparation of Intermediate 3.0 using benzonitrile instead of pentanenitrile, 2-(5-fluoropyrimidin-2-yl)ethanesulfonamide (Intermediate 5.0). The purification was performed using the method in Example 4.2. | 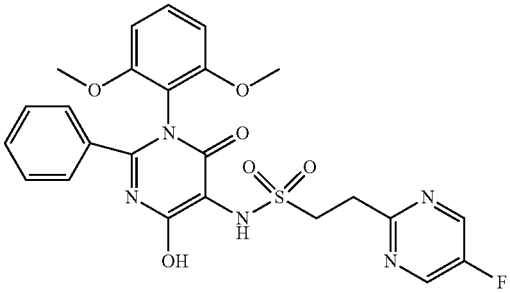 [SMILES: COc1cccc(OC)c1-n1c(-c2ccccc2)nc(O)c(NS(=O)(=O)CCc2ncc(F)cn2)c1=O]<br>N-[1-(2,6-dimethoxyphenyl)-4-hydroxy-6-oxo-2-phenyl-pyrimidin-5-yl]-2-(5-fluoropyrimidin-2-yl)ethanesulfonamide. $^1$H NMR (600 MHz, DMSO-$d_6$) δ 8.79-8.82 (m, 2 H), 8.32 (br s, 1 H), 7.09-7.21 (m, 6 H), 6.49 (d, J = 8.7 Hz, 2 H), 3.68-3.76 (m, 2 H), 3.62 (s, 6 H), 3.40-3.45 (m, 2 H). LCMS-ESI (pos.) m/z: 528.2 (M + H)$^+$. |

Following the procedure described in Example 4.0, the following compounds may be synthesized using the intermediates and conditions described in the following table (Table 2).

TABLE 2

| Example | Reagents | Structure, Name and Data |
|---|---|---|
| 4.10 | 5-bromo-2-butyl-3-(2,6-dimethoxyphenyl)-6-hydroxypyrimidin-4(3H)-one (Intermediate 3.0), (R)-1-(5-methylpyrimidin-2-yl)propane-2-sulfonamide and (S)-1-(5-methylpyrimidin-2-yl)propane-2-sulfonamide (Intermediate 5.6). | 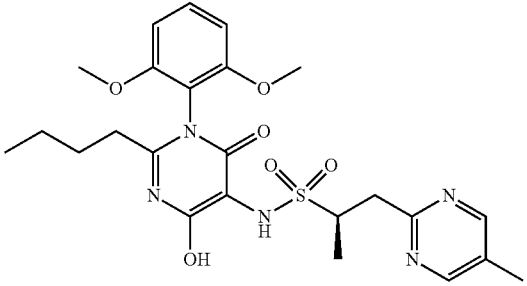 [SMILES: CCCCc1nc(O)c(NS(=O)(=O)[C@H](C)Cc2ncc(C)cn2)c(=O)n1-c1c(OC)cccc1OC]<br>and<br>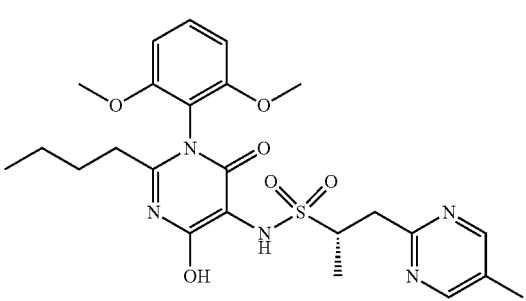 [SMILES: CCCCc1nc(O)c(NS(=O)(=O)[C@@H](C)Cc2ncc(C)cn2)c(=O)n1-c1c(OC)cccc1OC]<br>(R)-N-(2-butyl-1-(2,6-dimethoxyphenyl)-4-hydroxy-6-oxo-1,6-dihydropyrimidin-5-yl)-1-(5-methylpyrimidin-2-yl)propane-2-sulfonamide and (S)-N-(2-butyl-1-(2,6-dimethoxyphenyl)-4-hydroxy-6-oxo-1,6-dihydropyrimidin-5-yl)-1-(5-methylpyrimidin-2-yl)propane-2-sulfonamide. |

TABLE 2-continued

| Example | Reagents | Structure, Name and Data |
|---|---|---|
| 4.11 | 4,6-dimethoxypyrimdin-5-amine (CAS: 15846-15-8). | 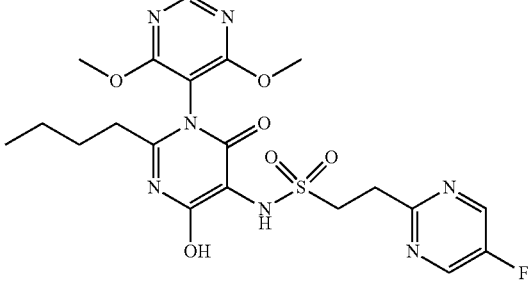<br>N-[2-butyl-1-(4,6-dimethoxypyrimidin-5-yl)-4-hydroxy-6-oxo-pyrimidin-5-yl]-2-(5-fluoropyrimidin-2-yl)ethanesulfonamide. |
| 4.12 | 2-(pyridin-2-yl)ethane-1-sulfonamide (CAS: 776287-41-3). | 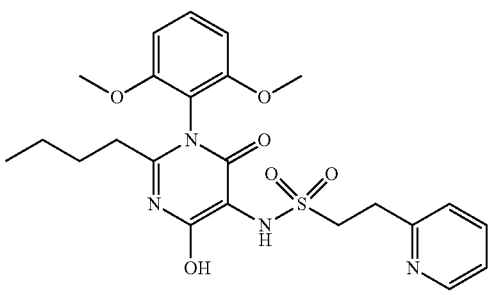 [SMILES: CCCCc1nc(O)c(NS(=O)(=O)CCc2ccccn2)c(=O)n1-c1c(OC)cccc1OC]<br>N-[2-butyl-1-(2,6-dimethoxyphenyl)-4-hydroxy-6-oxo-pyrimidin-5-yl]-2-(2-pyridyl)ethanesulfonamide. |
| 4.13 | 2-(napthalen-2-yl)ethane-1-sulfonamide (CAS: 105908-38-1). | 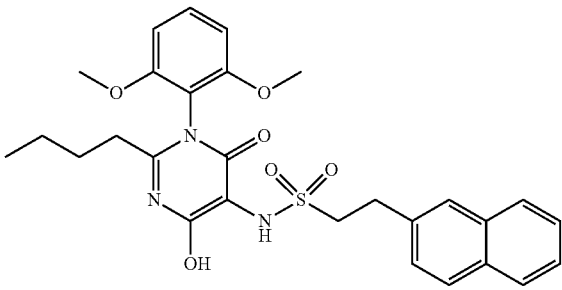 [SMILES: CCCCc1nc(O)c(NS(=O)(=O)CCc2ccc3ccccc3c2)c(=O)n1-c1c(OC)cccc1OC]<br>N-[2-butyl-1-(2,6-dimethoxyphenyl)-4-hydroxy-6-oxo-pyrimidin-5-yl]-2-(2-naphthyl)ethanesulfonamide. |
| 4.14 | 2-ethoxyacetonitrile (CAS: 62957-60-2). | 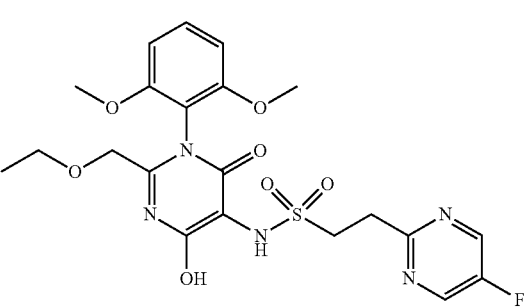 [SMILES: CCOCc1nc(O)c(NS(=O)(=O)CCc2ncc(F)cn2)c(=O)n1-c1c(OC)cccc1OC]<br>N-[1-(2,6-dimethoxyphenyl)-2-(ethoxymethyl)-4-hydroxy-6-oxo-pyrimidin-5-yl]-2-(5-fluoropyrimidin-2-yl)ethanesulfonamide. |

TABLE 2-continued

| Example | Reagents | Structure, Name and Data |
|---|---|---|
| 4.15 | 6-methoxypyridine-2-carbonitrile (CAS: 83621-01-6). | 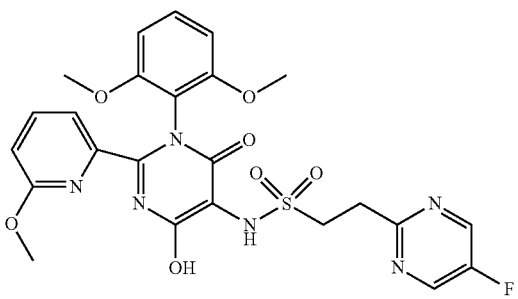 [SMILES: COc1cccc(-c2nc(O)c(NS(=O)(=O)CCc3ncc(F)cn3)c(=O)n2-c2c(OC)cccc2OC)n1]<br>N-[1-(2,6-dimethoxyphenyl)-4-hydroxy-2-(6-methoxy-2-pyridyl)-6-oxo-pyrimidin-5-yl]-2-(5-fluoropyrimidin-2-yl)ethanesulfonamide. |
| 4.16 | Tetrahydrofuran-2-carbonitrile (CAS: 14631-43-7). | 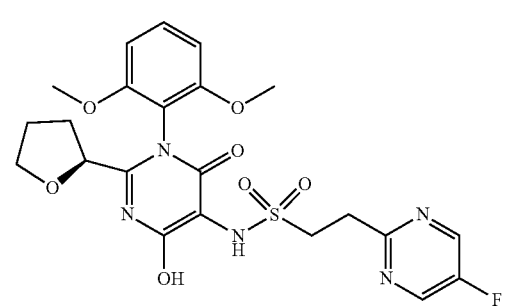 [SMILES: COc1cccc(OC)c1-n1c([C@@H]2CCCO2)nc(O)c(NS(=O)(=O)CCc2ncc(F)cn2)c1=O]<br>and<br>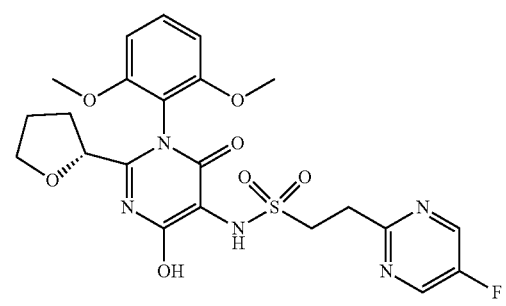 [SMILES: COc1cccc(OC)c1-n1c([C@H]2CCCO2)nc(O)c(NS(=O)(=O)CCc2ncc(F)cn2)c1=O]<br>(S)-N-[1-(2,6-dimethoxyphenyl)-4-hydroxy-6-oxo-2-tetrahydrofuran-2-yl-pyrimidin-5-yl]-2-(5-fluoropyrimidin-2-yl)ethanesulfonamide and (R)-N-[1-(2,6-dimethoxyphenyl)-4-hydroxy-6-oxo-2-tetrahydrofuran-2-yl-pyrimidin-5-yl]-2-(5-fluoropyrimidin-2-yl)ethanesulfonamide. |
| 4.18 | Tetrahydrofuran-3-carbonitrile (CAS: 14631-44-8). | 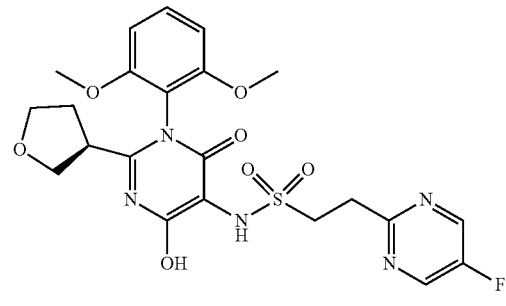 [SMILES: COc1cccc(OC)c1-n1c([C@@H]2CCOC2)nc(O)c(NS(=O)(=O)CCc2ncc(F)cn2)c1=O]<br>and |

TABLE 2-continued

| Example | Reagents | Structure, Name and Data |
|---|---|---|
| | | 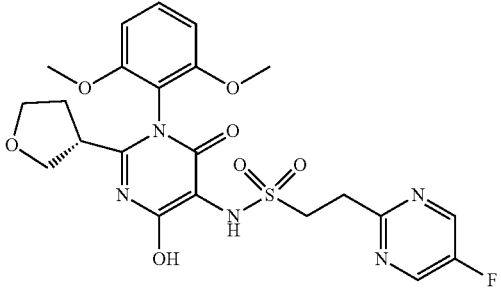 [SMILES: COc1cccc(OC)c1-n1c([C@H]2CCOC2)nc(O)c(NS(=O)(=O)CCc2ncc(F)cn2)c1=O](S)-N-[1-(2,6-dimethoxyphenyl)-4-hydroxy-6-oxo-2-tetrahydrofuran-3-yl-pyrimidin-5-yl]-2-(5-fluoropyrimidin-2-yl)ethanesulfonamide and (R)-N-[1-(2,6-dimethoxyphenyl)-4-hydroxy-6-oxo-2-tetrahydrofuran-3-yl-pyrimidin-5-yl]-2-(5-fluoropyrimidin-2-yl)ethanesulfonamide. |
| 4.19 | 1-phenylethan-1-amine (CAS: 618-36-0). | 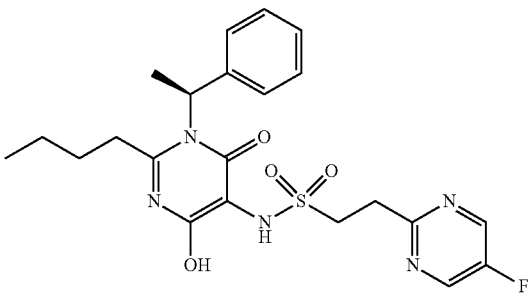 [SMILES: CCCCc1nc(O)c(NS(=O)(=O)CCc2ncc(F)cn2)c(=O)n1[C@@H](C)c1ccccc1]and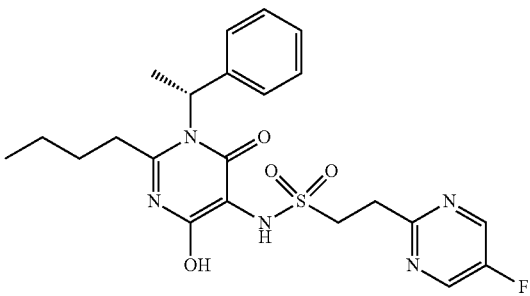 [SMILES: CCCCc1nc(O)c(NS(=O)(=O)CCc2ncc(F)cn2)c(=O)n1[C@H](C)c1ccccc1](S)-N-[2-butyl-4-hydroxy-6-oxo-1-(1-phenylethyl)pyrimidin-5-yl]-2-(5-fluoropyrimidin-2-yl)ethanesulfonamide and (R)-N-[2-butyl-4-hydroxy-6-oxo-1-(1-phenylethyl)pyrimidin-5-yl]-2-(5-fluoropyrimidin-2-yl)ethanesulfonamide. |
| 4.20 | 1-phenylpropan-1-amine (CAS: 2941-20-0). | 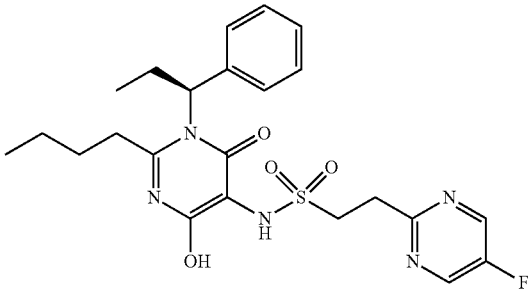 [SMILES: CCCCc1nc(O)c(NS(=O)(=O)CCc2ncc(F)cn2)c(=O)n1[C@@H](CC)c1ccccc1]and |

TABLE 2-continued

| Example | Reagents | Structure, Name and Data |
|---------|----------|--------------------------|
|         |          | 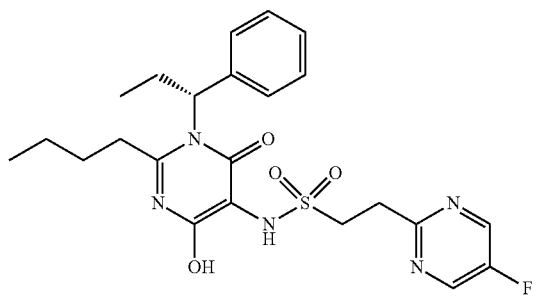 [SMILES: CCCCc1nc(O)c(NS(=O)(=O)CCc2ncc(F)cn2)c(=O)n1[C@H](CC)c1ccccc1] (S)-N-[2-butyl-4-hydroxy-6-oxo-1-(1-phenylpropyl)pyrimidin-5-yl]-2-(5-fluoropyrimidin-2-yl)ethanesulfonamide and (R)-N-[2-butyl-4-hydroxy-6-oxo-1-(1-phenylpropyl)pyrimidin-5-yl]-2-(5-fluoropyrimidin-2-yl)ethanesulfonamide. |
| 4.21    | 1-(oxan-4-yl)propan-1-amine (CAS: 854697-14-6). | 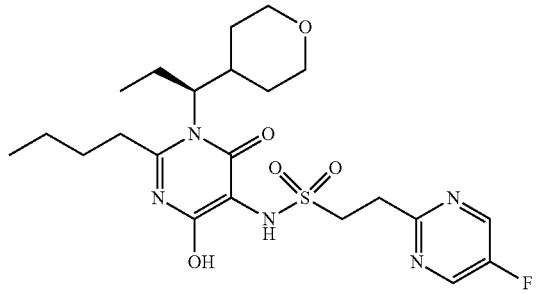 [SMILES: CCCCc1nc(O)c(NS(=O)(=O)CCc2ncc(F)cn2)c(=O)n1[C@@H](CC)C1CCOCC1] and 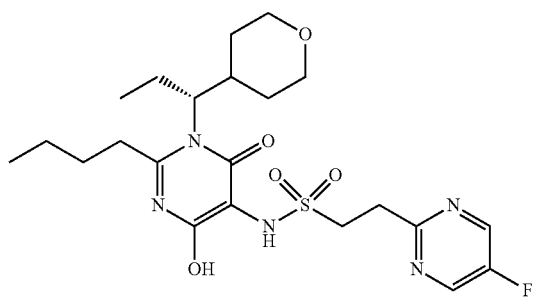 [SMILES: CCCCc1nc(O)c(NS(=O)(=O)CCc2ncc(F)cn2)c(=O)n1[C@H](CC)C1CCOCC1] (S)-N-[2-butyl-4-hydroxy-6-oxo-1-(1-tetrahydropyran-4-ylpropyl)pyrimidin-5-yl]-2-(5-fluoropyrimidin-2-yl)ethanesulfonamide and (R)-N-[2-butyl-4-hydroxy-6-oxo-1-(1-tetrahydropyran-4-ylpropyl)pyrimidin-5-yl]-2-(5-fluoropyrimidin-2-yl)ethanesulfonamide. |
| 4.22    | Oxan-3-amine (CAS: 120811-32-7). | 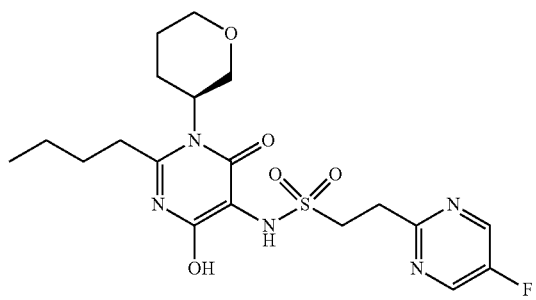 [SMILES: CCCCc1nc(O)c(NS(=O)(=O)CCc2ncc(F)cn2)c(=O)n1[C@H]1CCCOC1] and |

TABLE 2-continued

| Example | Reagents | Structure, Name and Data |
|---|---|---|
| | | 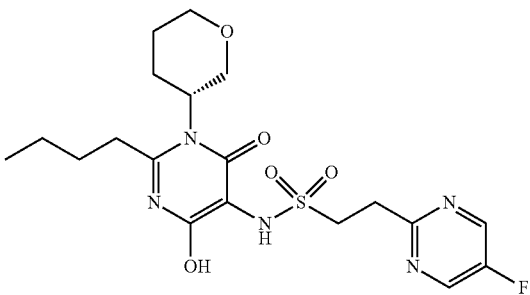 [SMILES: CCCCc1nc(O)c(NS(=O)(=O)CCc2ncc(F)cn2)c(=O)n1[C@@H]1CCCOC1]<br>(S)--(2-butyl-4-hydroxy-6-oxo-1-tetrahydropyran-3-yl-pyrimidin-5-yl)-2-(5-fluoropyrimidin-2-yl)ethanesulfonamide and (R)-N-(2-butyl-4-hydroxy-6-oxo-1-tetrahydropyran-3-yl-pyrimidin-5-yl)-2-(5-fluoropyrimidin-2-yl)ethanesulfonamide. |
| 4.23 | 2-methoxy-1-(oxan-4-yl)ethan-1-amine (CAS: 1340266-43-4). | 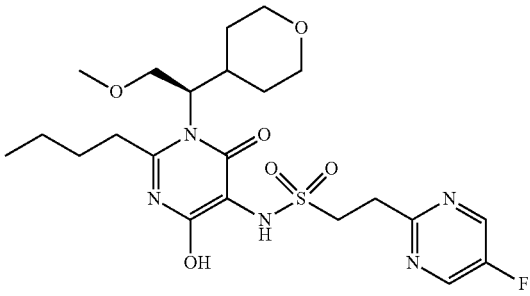 [SMILES: CCCCc1nc(O)c(NS(=O)(=O)CCc2ncc(F)cn2)c(=O)n1[C@@H](COC)C1CCOCC1]<br>and<br>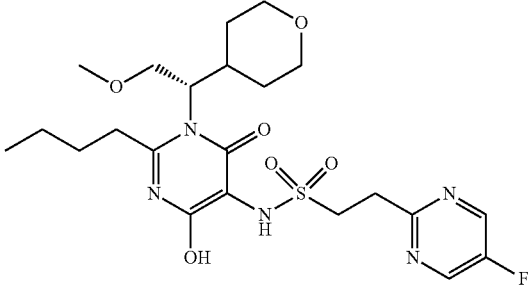 [SMILES: CCCCc1nc(O)c(NS(=O)(=O)CCc2ncc(F)cn2)c(=O)n1[C@H](COC)C1CCOCC1]<br>(R)-N-[2-butyl-4-hydroxy-1-(2-methoxy-1-tetrahydropyran-4-yl-ethyl)-6-oxo-pyrimidin-5-yl]-2-(5-fluoropyrimidin-2-yl)ethanesulfonamide and (S)-N-[2-butyl-4-hydroxy-1-(2-methoxy-1-tetrahydropyran-4-yl-ethyl)-6-oxo-pyrimidin-5-yl]-2-(5-fluoropyrimidin-2-yl)ethanesulfonamide. |
| 4.25 | 5-methyl-2-furonitrile (CAS: 13714-86-8). | 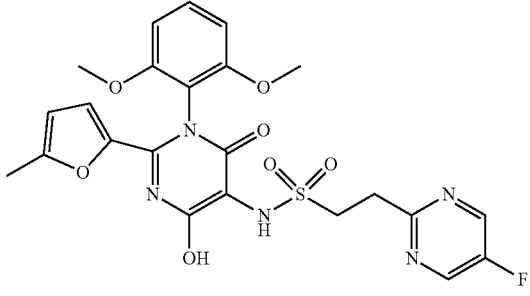 [SMILES: COc1cccc(OC)c1-n1c(-c2ccc(C)o2)nc(O)c(NS(=O)(=O)CCc2ncc(F)cn2)c1=O]<br>N-[1-(2,6-dimethoxyphenyl)-4-hydroxy-2-(5-methyl-2-furyl)-6-oxo-pyrimidin-5-yl]-2-(5-fluoropyrimidin-2-yl)ethanesulfonamide. |

TABLE 2-continued

| Example | Reagents | Structure, Name and Data |
|---|---|---|
| 4.26 | 1-methyl-1H-indazole-3-carbonitrile (CAS: 31748-44-4). | 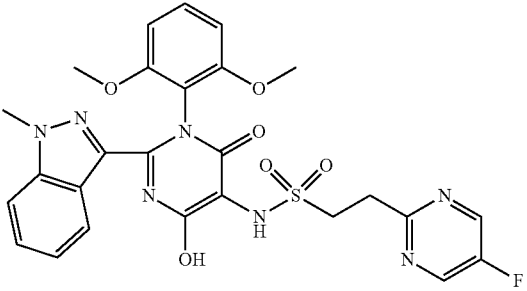 [SMILES: COc1cccc(OC)c1-n1c(-c2nn(C)c3ccccc23)nc(O)c(NS(=O)(=O)CCc2ncc(F)cn2)c1=O]<br>N-[1-(2,6-dimethoxyphenyl)-4-hydroxy-2-(1-methylindazol-3-yl)-6-oxo-pyrimidin-5-yl]-2-(5-fluoropyrimidin-2-yl)ethanesulfonamide. |
| 4.27 | (1S,2S)-1-Isopropoxy-1-(5-methylpyrimidin-2-yl)propane-2-sulfonamide (Intermediate 5.7). | 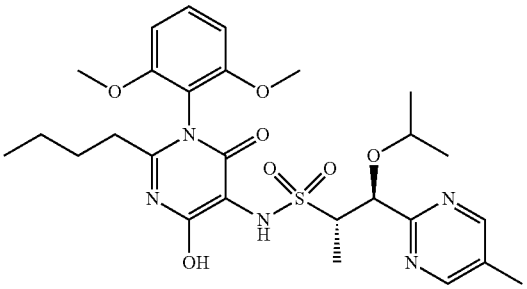 [SMILES: CCCCc1nc(O)c(NS(=O)(=O)[C@@H](C)[C@@H](OC(C)C)c2ncc(C)cn2)c(=O)n1-c1c(OC)cccc1OC]<br>(1S,2S)-N-(2-butyl-1-(2,6-dimethoxyphenyl)-4-hydroxy-6-oxo-1,6-dihydropyrimidin-5-yl)-1-isopropoxy-1-(5-methylpyrimidin-2-yl)propane-2-sulfonamide. |
| 4.28 | 5,5,5-Trifluoropentanonitrile (CAS: 89866-61-5). | 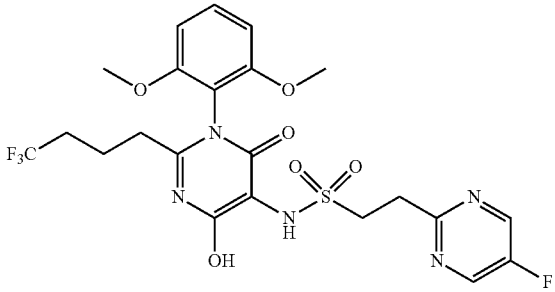 [SMILES: COc1cccc(OC)c1-n1c(CCCC(F)(F)F)nc(O)c(NS(=O)(=O)CCc2ncc(F)cn2)c1=O]<br>N-[1-(2,6-dimethoxyphenyl)-4-hydroxy-6-oxo-2-(4,4,4-trifluorobutyl)pyrimidin-5-yl]-2-(5-fluoropyrimidin-2-yl)ethanesulfonamide. |
| 4.29 | 4-hydroxybutanenitrile (CAS: 628-22-8). | 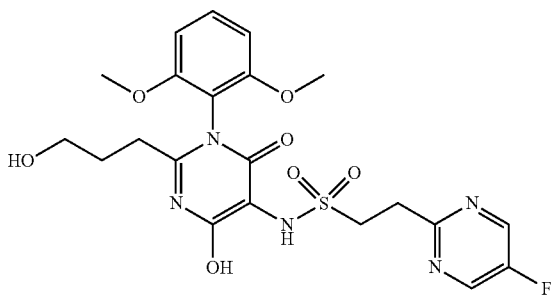 [SMILES: COc1cccc(OC)c1-n1c(CCCO)nc(O)c(NS(=O)(=O)CCc2ncc(F)cn2)c1=O]<br>N-[1-(2,6-dimethoxyphenyl)-4-hydroxy-2-(3-hydroxypropyl)-6-oxo-pyrimidin-5-yl]-2-(5-fluoropyrimidin-2-yl)ethanesulfonamide. |

TABLE 2-continued

| Example | Reagents | Structure, Name and Data |
|---|---|---|
| 4.30 | 4-(Trifluoromethoxy)butyronitrile (CAS: 1301738-94-2). | 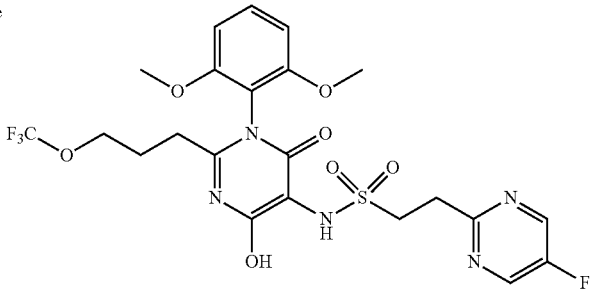<br>N-[1-(2,6-dimethoxyphenyl)-4-hydroxy-6-oxo-2-[3-(trifluoromethoxy)propyl]pyrimidin-5-yl]-2-(5-fluoropyrimidin-2-yl)ethanesulfonamide. |
| 4.31 | 2-methylpentanenitrile (CAS: 6339-13-5). | 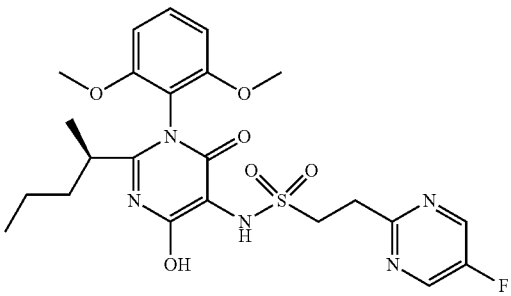 [SMILES: CCC[C@@H](C)c1nc(O)c(NS(=O)(=O)CCc2ncc(F)cn2)c(=O)n1-c1c(OC)cccc1OC]<br>and<br>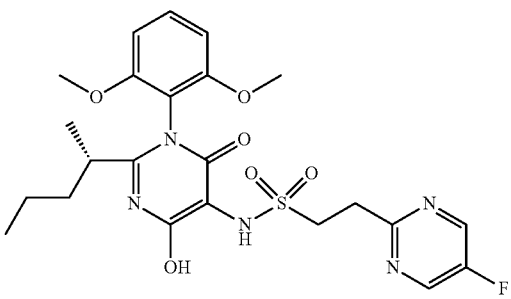 [SMILES: CCC[C@H](C)c1nc(O)c(NS(=O)(=O)CCc2ncc(F)cn2)c(=O)n1-c1c(OC)cccc1OC]<br>(R)-N-[1-(2,6-dimethoxyphenyl)-4-hydroxy-2-(1-methylbutyl)-6-oxo-pyrimidin-5-yl]-2-(5-fluoropyrimidin-2-yl)ethanesulfonamide and (S)-N-[1-(2,6-dimethoxyphenyl)-4-hydroxy-2-(1-methylbutyl)-6-oxo-pyrimidin-5-yl]-2-(5-fluoropyrimidin-2-yl)ethanesulfonamide. |
| 4.32 | Naphthalene-2-sulfonamide (CAS: 1576-47-2). | 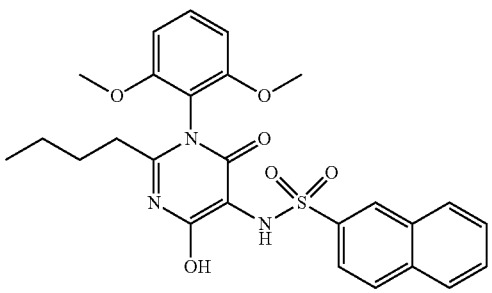 [SMILES: CCCCc1nc(O)c(NS(=O)(=O)c2ccc3ccccc3c2)c(=O)n1-c1c(OC)cccc1OC]<br>N-[2-butyl-1-(2,6-dimethoxyphenyl)-4-hydroxy-6-oxo-pyrimidin-5-yl]naphthalene-2-sulfonamide. |

Intermediate 5.0. Preparation of
2-(5-fluoropyrimidin-2-yl)ethanesulfonamide

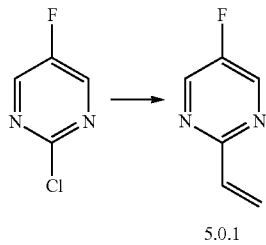

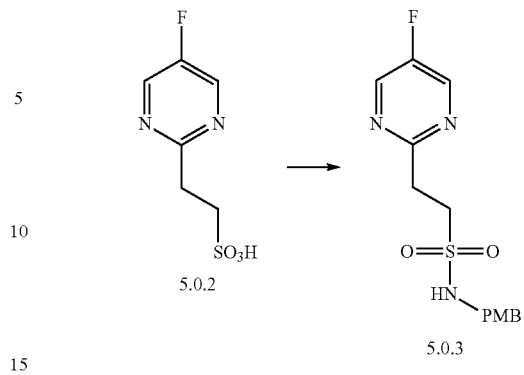

5-Fluoro-2-vinylpyrimidine, intermediate 5.0.1, To a solution of 2-chloro-5-fluoropyrimidine (Sigma Aldrich, 10.0 g, 75.46 mmol) in DMF (100 mL) was added tributyl (vinyl)tin (31.1 g, 98.09 mmol) at RT. The reaction mixture was pinged with $N_2$ for 5 min and Pd(PPh$_3$)$_4$ (2.62 g, 2.26 mmol) was added. The reaction mixture was degassed with $N_2$ for 5 min and stirred at 100° C. for 24 h. After completion of the reaction (monitored by TLC), the reaction mixture was cooled to RT and quenched with water (100 mL). The aqueous layer was extracted with diethyl ether (2×100 mL). The combined organic layer was washed with brine (100 mL), dried over anhydrous $Na_2SO_4$ and concentrated under reduced pressure to give the product, which was purified by combi-flash chromatography (redisep column 120 g; elution: 6% EtOAc in hexane) to provide Intermediate 5.0.1 (8.0 g, 85.1%) as an oil. $^1$H NMR (400 MHz, CDCl$_3$) δ 8.58-8.49 (m, 2H), 6.86 (dd, J=17.4, 10.6 Hz, 1H), 6.53 (d, J=17.3 Hz, 1H), 5.70 (d, J=10.6 Hz, 1H). MS (ESI, positive ion) m/z: 125.1.

2-(5-Fluoropyrimidin-2-yl)-N-(4-methoxybenzyl)ethanesulfonamide, Intermediate 5.0.3, To a suspension of Intermediate 5.0.2 (16.0 g, 77.30 mmol) in DCM (385 mL) was added oxalyl chloride (29.4 g, 231.8 mmol) followed by DMF (1 mL) at 0° C. The reaction mixture was stirred at RT for 1 h and then concentrated under reduced pressure. The reaction mixture was azeotroped with cyclopentylmethylether to remove traces of oxalyl chloride. The reaction mixture was diluted with DCM (385 mL), cooled to 0° C. and 4-methoxybenzylamine (31.8 g, 231.88 mmol) followed by TEA (39.1 g, 386.4 mmol) were added. The reaction mixture was stirred at RT for 12 h. After completion of the reaction (monitored by TLC), the reaction mixture was quenched with water (500 mL). The aqueous layer was extracted with DCM (2×400 mL). The organic layer was washed with brine (1.0 L), dried over anhydrous $Na_2SO_4$ and concentrated under reduced pressure to obtain the initial product which was purified by column chromatography (silica, 100-200 mesh; elution 55% EtOAc in hexane) to provide Intermediate 5.0.3 (13.5 g, 53.5%) as an off yellow solid. MS (ESI, positive ion) m/z: 326.1.

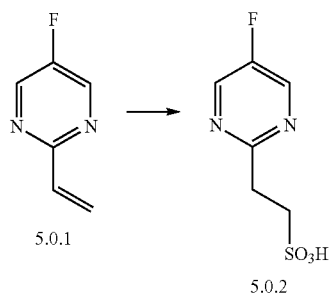

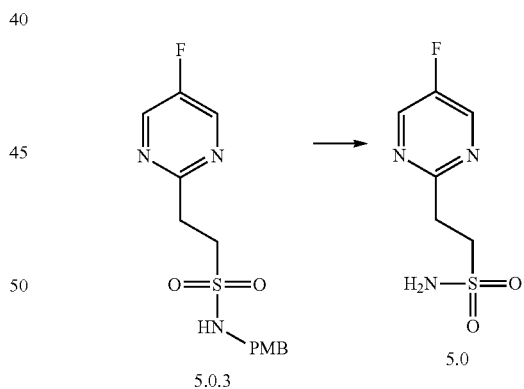

2-(5-Fluoropyrimidin-2-yl) ethanesulfonic acid, Intermediate 5.0.2, A solution of Intermediate 5.0.1 (20.0 g, 16.12 mmol) in a saturated aqueous solution of NaHSO$_3$ (80 mL) was stirred at RT for 12 h. After completion of the reaction (monitored by TLC), the reaction mixture was concentrated under reduced pressure to give the initial product which was purified by flash chromatography on (120 g Redisep elution: 4-10% H$_2$O in MeCN) to provide Intermediate 5.0.2 (16.0 g, 47.9%) as a white solid. $^1$H NMR (400 MHz, DMSO) δ 8.89-8.73 (m, 2H), 3.17 (t, J=8.2 Hz, 2H), 2.85 (t, J=8.2 Hz, 2H).

2-(5-Fluoropyrimidin-2-yl)ethanesulfonamide, Intermediate 5.0. To a suspension of Intermediate 5.0.3 (13.5 g, 41.41 mmol) in DCM (46 mL) was added TFA (207 mL) at 0° C. The reaction mixture was stirred at RT for 12 h. After completion of the reaction (monitored by TLC), the reaction mixture was concentrated under reduced pressure to give the residue which was purified by flash chromatography (elution: 65% EtOAc in hexane) to provide Intermediate 5.0 (5.3 g, 62.5%) as an off yellow solid. MS (ESI, positive ion) m/z: 206.0. $^1$H NMR (400 MHz, DMSO) δ 8.77 (s, 2H), 6.92 (s, 2H), 3.54-3.48 (m, 2H), 3.24-3.20 (s, 2H).

Intermediate 5.1. Preparation of (2S,3R)-3-(5-fluoropyrimidin-2-yl)butane-2-sulfonamide

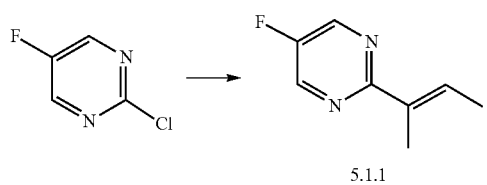

5.1.1

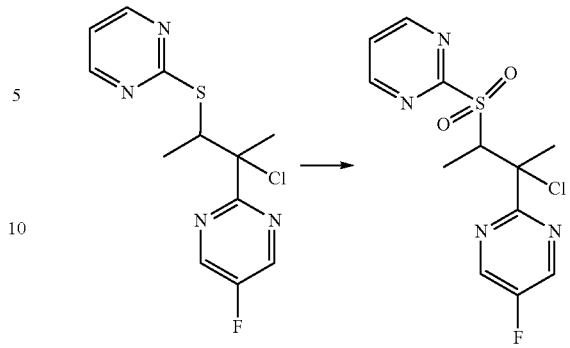

(E)-2-(But-2-en-2-yl)-5-fluoropyrimidine, Intermediate 5.1.1, 2-Chloro-5-fluoro-pyrimidine (14.45 ml, 117 mmol), potassium (Z)-but-2-en-2-yltrifluoroborate (24.63 g, 152 mmol), tricyclohexylphosphine (6.56 g, 23.39 mmol), and Pd$_2$(dba)$_3$ (10.71 g, 11.70 mmol) were added to a vial and then degassed and backfilled with nitrogen. To the vial, 1,4-dioxane (195 ml,) and aqueous potassium phosphate tribasic (29.0 ml, 351 mmol) were added by syringe. The resulting reaction was heated to 100° C. for 16 h. The reaction was cooled to RT. The organics were concentrated under reduced pressure. The residue was filtered through a plug of silica gel, then loaded onto silica gel (0-20% EtOAc in hexanes) to afford Intermediate 5.1.1 (14.24 g, 94 mmol, 80% yield). LCMS-ESI (POS.) M/Z: 153.1 (M+H)$^+$.

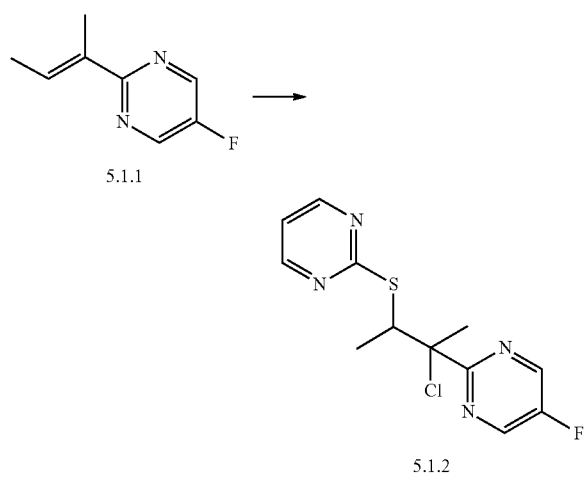

2-(2-Chloro-3-(pyrimidin-2-ylthio)butan-2-yl)-5-fluoropyrimidine, Intermediate 5.1.2, To a solution of pyrimidine-2-thiol (13.27 g, 118 mmol) in DCM (329 ml) was added sulfuryl dichloride (9.62 ml, 118 mmol). The reaction was stirred at 0° C. for 1 h and a further 1 h at 23° C. To the cloudy reaction was added Intermediate 5.1.1 (15 g, 99 mmol) dropwise. The reaction was further stirred for 1 h. The reaction mixture was then concentrated in vacuo. A saturated aqueous solution of sodium bicarbonate was added to the mixture to neutralize the reaction mixture. The reaction was extracted with EtOAc and concentrated in vacuo. The residue was purified on silica gel with 0-25% EtOAc in hexanes to give the desired product Intermediate 5.1.2 (21 g, 70.3 mmol, 71.3% yield). LCMS-ESI (POS.) M/Z: 291.1 (M+H)$^+$.

2-(2-Chloro-3-(pyrimidin-2-ylsulfonyl)butan-2-yl)-5-fluoropyrimidine, Intermediate 5.1.3, To a solution of Intermediate 5.1.2 (21 g, 70.3 mmol) in DCM (201 mL) was added 3-chlorobenzoperoxoic acid (24.26 g, 141 mmol) at 0° C. The reaction was stirred at 23° C. for 1 day. The reaction was concentrated in vacuo and an aqueous solution of sodium bicarbonate and sodium thiosulfate was added. The mixture was extracted with EtOAc and concentrated in vacuo and purified on silica gel eluting with 0-100% EtOAc in hexane to give the desired product Intermediate 5.1.3 (18 g, 54.4 mmol, 77% yield). LCMS-ESI (POS.) M/Z: 331.1 (M+H)$^+$.

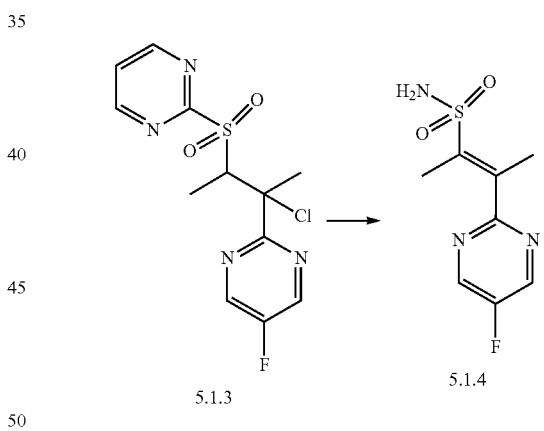

(E)-3-(5-Fluoropyrimidin-2-yl)but-2-ene-2-sulfonamide, Intermediate 5.1.4, To a stirred solution of Intermediate 5.1.3 (18 g, 54.4 mmol) in MeOH (136 ml) was added potassium carbonate (15.04 g, 109 mmol). The reaction was stirred at 23° C. for 16 h and was then concentrated in vacuo. The sulfinate was dissolved in water (231 mL, 46.3 mmol) and potassium acetate (4.54 g, 46.3 mmol) was added, followed by (aminooxy)sulfonic acid (10.47 g, 93 mmol). The reaction was stirred at 23° C. for 3 h and was then extracted with EtOAc and concentrated in vacuo. The product was purified on silica gel eluting with 0-80% EtOAc in hexanes to give the desired product Intermediate 5.1.4 (11.77 g, 46.3 mmol). LCMS-ESI (POS.) M/Z: 232.1 (M+H)$^+$.

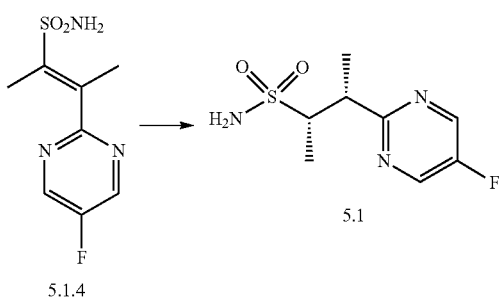

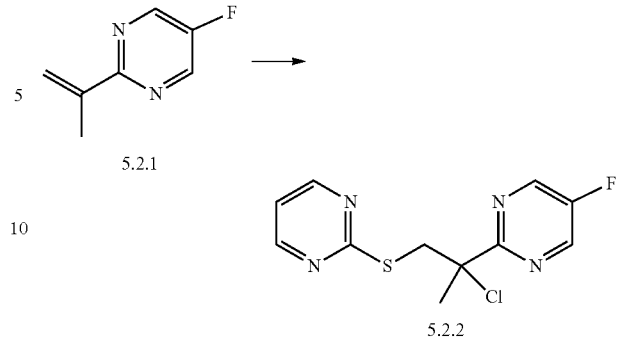

(2S,3R)-3-(5-Fluoropyrimidin-2-yl)butane-2-sulfonamide, Intermediate 5.1. To a solution of Intermediate 5.1.4 (0.77 g, 3.33 mmol) in EtOH (8.32 ml) was added zinc(II) trifluoromethanesulfonate (0.121 g, 0.333 mmol), and (R)-(−)-4,12-Bis(diphenylphosphino)[2.2]paracyclophane(1,5-cyclooctadiene)rhodium(I) tetrafluoroborate, min. 97% (Strem chemicals, 45-0217, 0.116 g, 0.133 mmol). The reaction mixture was placed under an atmosphere of hydrogen. The reaction was stirred for 16 h and was then filtered, concentrated in vacuo, and purified on silica gel eluting with 0-80% EtOAc in hexanes to give the desired product. The combined product was recrystallized from EtOH to give the desired product (0.46 g, 60%, 99% ee) Intermediate 5.1. LCMS-ESI (POS.) M/Z: 234.2 (M+H)$^+$.

Intermediate 5.2.5. Preparation of (R)-2-(5-fluoropyrimidin-2-yl)propane-1-sulfonamide and (S)-2-(5-fluoropyrimidin-2-yl)propane-1-sulfonamide

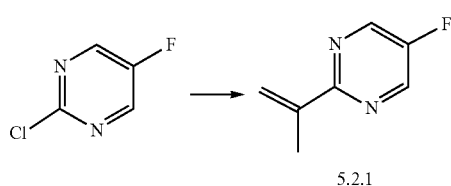

5-Fluoro-2-(prop-1-en-2-yl)pyrimidine, Intermediate 5.2.1, A mixture of 2-chloro-5-fluoropyrimidine (50.0 g, 377.0 mmol. CAS: 62802-42-0), potassium trifluoro(prop-1-en-2-yl)borate (84.0 g, 566.0 mmol) and K$_2$CO$_3$ (78.0 g, 566.0 mmol) in 1,4-dioxane (400 mL) and water (100 mL) were added to a sealed tube (1 L). The reaction mixture was degassed and purged with nitrogen for 20 min. PdCl$_2$(dppf) (7.70 g, 9.43 mmol) was added and the reaction tube was sealed and heated to 70° C. After 18 h, the reaction mixture was cooled to RT, diluted with diethyl ether (500 mL), and filtered through Celite® filter aid. The filter cake was washed with diethyl ether (500 mL). The combined filtrate was extracted with diethyl ether (2×2 L). The organic layer was washed with cold water (2×2 L), dried over Na$_2$SO$_4$ and concentrated under reduced pressure at 35° C. The material was purified by column chromatography over silica gel (60-120 mesh) using 5% EtOAc in hexanes as an eluent to give Intermediate 5.2.1 (41.0 g, 297.0 mmol, 79% yield) as a colourless oil. $^1$H NMR (400 MHz, CDCl$_3$) δ 8.59 (s, 2H), 6.38 (t, J=1.2 Hz, 1H), 5.54 (t, T=1.2 Hz, 1H), 2.26 (dd, J=1.2, 0.8 Hz, 3H).

2-(2-Chloro-1-(pyrimidin-2-ylthio)propan-2-yl)-5-fluoropyrimidine, Intermediate 5.2.2, To a stirred solution of pyrimidine-2-thiol (49.9 g, 356.0 mmol, CAS: 1450-85-7) in DCM (750 mL) was added sulfuryl chloride (36.2 mL, 356.0 mmol) slowly at 0° C. The reaction mixture was stirred at 0° C. for 2 h followed by stirring at RT for 2 h. A solution of Intermediate 5.2.1 (41.0 g, 297.0 mmol) in DCM (410 mL) was added slowly to the reaction mixture and stirred at RT for 16 h. The reaction mixture was quenched with saturated aqueous NaHCO$_3$ solution (1 L) and extracted with DCM (2×1.0 L). The organic layer was dried over anhydrous Na$_2$SO$_4$, filtered, and concentrated under reduced pressure. The residue was purified by column chromatography over silica gel (60-120 mesh) using 1% to 15% EtOAc in hexanes as an eluent to give Intermediate 5.2.2 (37.5 g, 44% yield). $^1$H NMR (400 MHz, CDCl$_3$) δ 8.64 (s, 2H), 8.54 (d, J=4.8 Hz, 2H), 7.00 (t, J=4.8 Hz, 1H), 4.48 (d, J=13.6 Hz, 1H), 4.39 (d, J=13.6 Hz, 1H), 2.16 (s, 3H).

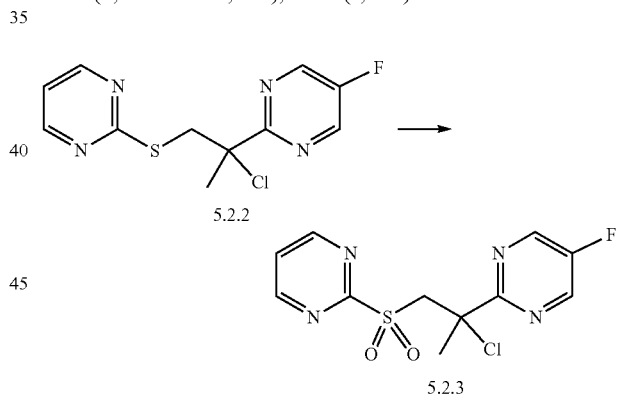

2-(2-Chloro-1-(pyrimidin-2-ylsulfonyl)propan-2-yl)-5-fluoropyrimidine, Intermediate 5.2.3, To a stirred solution of Intermediate 5.2.2 (75.0 g, 263.0 mmol) in DCM (750 mL) was added mCPBA (114.0 g, 658.0 mmol) under N$_2$ atmosphere, and the mixture was stirred at RT for 16 h. The reaction mixture was quenched with water (1 L) and extracted with DCM (4×1 L). The organic layer was washed with saturated aqueous NaHCO$_3$ solution (4×2 L) followed by brine solution (2 L), dried over anhy. Na$_2$SO$_4$, filtered and concentrated under reduced pressure. The solid residue was triturated with diethyl ether (1 L), filtered and dried under vacuum to give Intermediate 5.2.3 (55 g, 66% yield. $^1$H NMR (400 MHz, CDCl$_3$) δ 8.98 (d, J=4.8 Hz, 2H), 8.56 (s, 2H), 7.59 (t, J=4.8 Hz, 1H), 5.17 (d, T=14.6 Hz, 1H), 4.72 (dd, J=14.6 Hz, 1H), 2.30 (s, 3H). LCMS-ESI (pos.) m/z: 317.0 (M+H)$^+$.

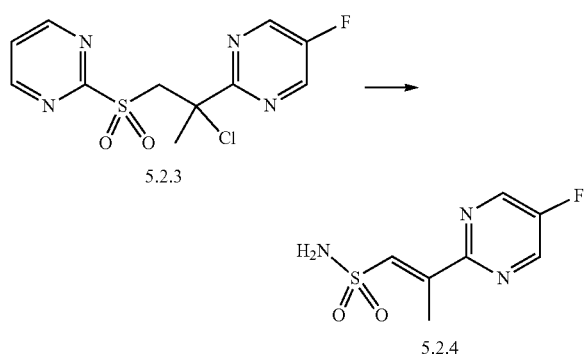

2-(5-Fluoropyrimidin-2-yl)prop-1-ene-1-sulfonamide, Intermediate 5.2.4, To a stirred solution of Intermediate 5.2.3 (50.0 g, 158.0 mmol) in MeOH (500.0 mL) was added potassium carbonate (43.6 g, 316 mmol). The mixture was then stirred at RT for 16 h. The reaction was concentrated under reduced pressure. The solid was triturated with diethyl ether (1 L), filtered and dried under vacuum. The solid was added to water (350 mL) followed by addition of potassium acetate (28.6 g, 291.0 mmol) and (aminooxy)sulfonic acid (65.9 g, 583.0 mmol) in portions at 0° C. After the addition was complete, the reaction mixture was warmed to RT and stirred for 2 h. The reaction mixture was extracted with 10% MeOH in EtOAc (2×500 mL). The organic layer was washed with brine (250.0 mL), dried over anhydrous Na$_2$SO$_4$, filtered and concentrated under reduced pressure. The material was absorbed onto a plug of silica gel and purified by flash chromatography through a Redi-Sep pre-packed silica gel column (80.0 g), eluting with a gradient of 0% to 50% EtOAc in hexanes, to give Intermediate 5.2.4 (22.0 g, 64% yield). $^1$H NMR (400 MHz, CDCl$_3$) δ 8.64 (d, J=5.0 Hz, 2H), 7.81 (s, 1H), 4.93 (s, 2H), 2.611 (s, 3H). LCMS-ESI (POS.) m/z: 218.0 (M+H)$^+$.

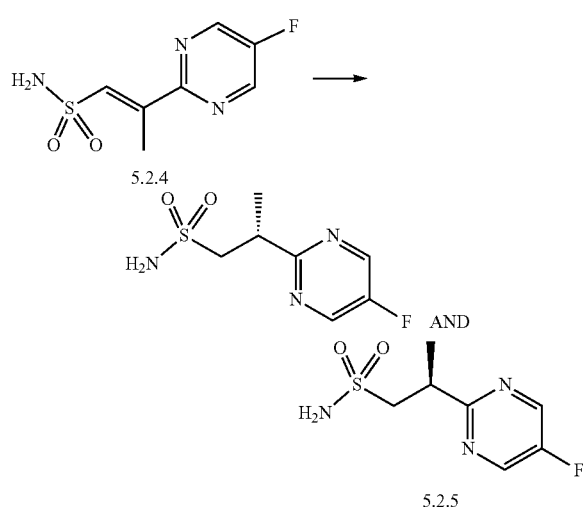

(R)-2-(5-Fluoropyrimidin-2-yl)propane-1-sulfonamide and (S)-2-(5-fluoropyrimidin-2-yl)propane-1-sulfonamide, Intermediate 5.2.5, To a solution of Intermediate 5.2.4 (22.0 g, 101.0 mmol) in MeOH (225.0 mL) was added zinc trifluoromethanesulfonate (9.20 g, 25.3 mmol), bis(1,5-cyclooctadiene)rhodium(I)tetrafluoroborate (1.028 g, 2.53 mmol) and Josiphos-1 (1.62 g, 2.53 mmol). The reaction mixture was degassed and purged with argon for 10 min. The reaction vessel was purged with hydrogen and kept under hydrogen pressure (3-4 bar) in an autoclave (450 mL) at 80° C. for 48 h. The reaction mixture was concentrated under reduced pressure. The residue was absorbed onto a plug of silica gel (60-120 mesh) and purified by flash chromatography through a Redi-Sep pre-packed silica gel column (80.0 g), eluting with a gradient of 0% to 50% EtOAc in hexanes to give Intermediate 5.2.5, Intermediate 5.2. Preparation of (R)-2-(5-fluoropyrimidin-2-yl)propane-1-sulfonamide or (N)-2-(5-fluoropyrimidin-2-yl)propane-1-sulfonamide

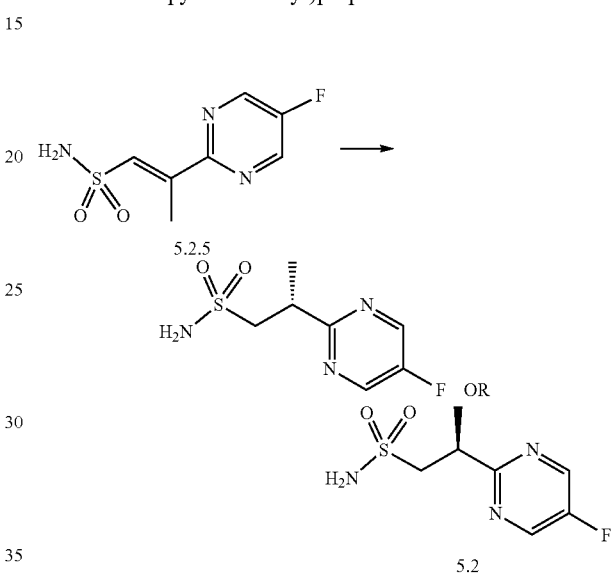

(R)-2-(5-Fluoropyrimidin-2-yl)propane-1-sulfonamide or (S)-2-(5-fluoropyrimidin-2-yl)propane-1-sulfonamide, Intermediate 5.2. Intermediate 5.2.5 was separated using chiral SFC (YMC Amylose SA (250×4.6 mm, 5 μm column), 70:30 liquid CO$_2$ and MeOH, 3 mL/min, 100 bar) to give Intermediate 5.2 (99.6% ee). $^1$H NMR (400 MHz, CDCl$_3$) δ 8.58 (s, 2H), 4.77 (s, 2H), 3.94 (dd, J=14.1, 8.8 Hz, 1H), 3.85-3.75 (m, 1H), 3.41 (dd, J=14.1, 4.3 Hz, 1H), 1.50 (d, J=6.9 Hz, 3H). LCMS-ESI (pos.) m/z: 220.1 (M+H)$^+$.

Intermediate 5.3. Preparation of (R)-2-(5-fluoropyrimidin-2-yl)propane-1-sulfonamide or (S)-2-(5-fluoropyrimidin-2-yl)propane-1-sulfonamide

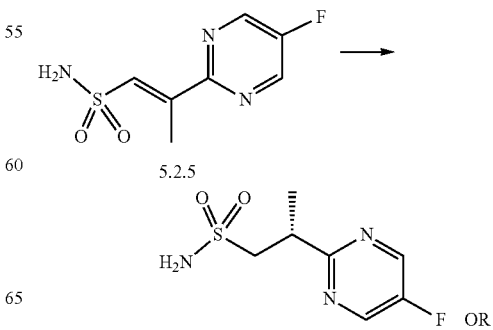

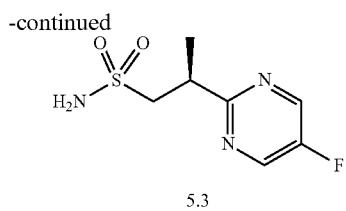

5.3

(R)-2-(5-fluoropyrimidin-2-yl)propane-1-sulfonamide or (S)-2-(5-fluoropyrimidin-2-yl)propane-1-sulfonamide, Intermediate 5.3. Further purification under the conditions described in Intermediate 5.2 delivered Intermediate 5.3 (98.8% ee). $^1$H NMR (400 MHz, CDCl$_3$) δ 8.58 (s, 2H), 4.77 (s, 2H), 3.94 (dd, J=14.1, 8.8 Hz, 1H), 3.85-3.75 (m, 1H), 3.41 (dd, J=14.1, 4.3 Hz, 1H), 1.50 (d, J=6.9 Hz, 3H). LCMS-ESI (pos.) m/z: 220.1 (M+H)$^+$.

Intermediate 5.4. Preparation of (S)-1-(5-fluoropyrimidin-2-yl)piperidine-3-sulfonamide or (R)-1-(5-fluoropyrimidin-2-yl)piperidine-3-sulfonamide

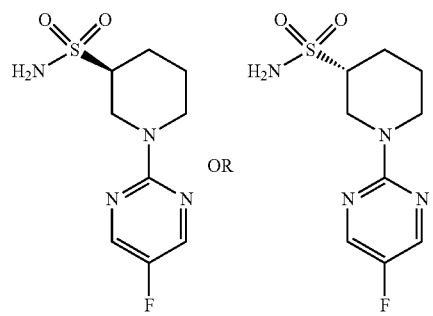

5.4

(S)-1-(5-Fluoropyrimidin-2-yl)piperidine-3-sulfonamide or (R)-1-(5-fluoropyrimidin-2-yl)piperidine-3-sulfonamide, Intermediate 5.4. To a solution of piperidine-3-sulfonamide hydrochloride (1.00 g, 4.98 mmol) in DMSO (24.9 mL) was added 2-chloro-5-fluoropyrimidine (3.30 g, 24.9 mmol) followed by Hunig's base (8.67 mL, 49.8 mmol). The flask was fitted with a condenser and placed into a reaction block preheated to 100° C. After 2 h, the mixture was cooled to RT and was diluted with DCM and water and the layers were separated. The organic layer was washed with water (×3) and brine (×2). The combined organic layers were washed with brine (×1), dried with magnesium sulfate, filtered and concentrated under reduced pressure. The solids were triturated with IPA and the solid was purified by chiral separation method (SFC: 100×4.6 mm AD-H column with 25% MeOH (20 mM NH$_3$), 5 mL/min) to give Intermediate 5.4. $^1$H NMR (400 MHz, DMSO-d$_6$) δ 8.47 (2H, d, J=0.83 Hz) 6.93 (2H, s) 4.94-5.06 (1H, m) 4.56 (1H, br d, J=12.23 Hz) 2.88-3.00 (2H, m) 2.81 (1H, td, J=12.83, 2.75 Hz) 2.18 (1H, br d, J=12.75 Hz) 1.76-1.85 (1H, m) 1.63-1.75 (1H, m) 1.38-1.52 (1H, m).

Intermediate 5.5. Preparation of (1R,2S)-1-methoxy-1-(5-methylpyrimidin-2-yl)propane-2-sulfonamide

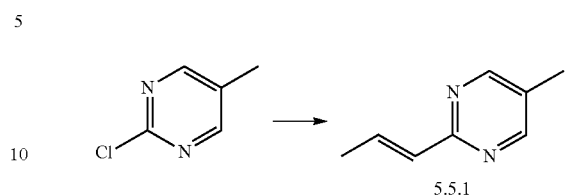

5.5.1

(E)-5-Methyl-2-(prop-1-en-1-yl)pyrimidine, Intermediate 5.5.1, To a 500 mL round bottomed flask was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was pinged with N$_2$ (5×), then 1,4-dioxane (200 ml), and water (20.00 ml) were added. The resulting yellow suspension was bubbled with Ar for 15 min and then 1,1-bis[(di-t-butyl-p-methylaminophenyl]palladium(ii) chloride (Amphos, commercially available from Strem, 2.64 g, 3.73 mmol) was added. A reflux condenser was attached and the reaction was warmed to 90° C. in an oil bath and stirred under N$_2$ for 16.5 h. The reaction was then cooled to RT. The reaction was diluted with water (250 mL), and extracted with EtOAc (2×250 mL). The organic layers were combined, dried (MgSO$_4$), and concentrated in vacuo. The residue was purified by flash chromatography on silica gel eluting with 0-20% EtOAc/hexanes) to afford Intermediate 5.5.1 (12.96 g, 97 mmol, 100% yield) as a yellow/orange oily solid. $^1$H NMR (300 MHz, CDCl$_3$) δ 8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 1H). MS (ESI pos. ion) m/z: 135.2 (M+H).

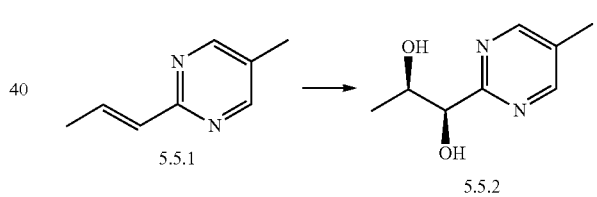

(1R,2R)-1-(5-Methylpyrimidin-2-yl)propane-1,2-diol, Intermediate 5.5.2, Racemic conditions: To a solution of (E)-5-methyl-2-(prop-1-en-1-yl)pyrimidine (Intermediate 5.5.1, 5.75 g, 42.9 mmol) and 4-methylmorpholine-4-oxide (7.53 g, 64.3 mmol) in acetone (60 mL) and water (6 mL) was added osmium tetroxide, 4 wt. %, in water (0.681 mL, 0.111 mmol). The reaction was stirred at RT under N$_2$ 21.5 h. LCMS showed complete conversion to a product corresponding to the mass of the desired product (M+H=169). The reaction was passed through a Varian Chem-Elut cartridge to remove water and then concentrated in vacuo. Water was still present. The residue was dissolved in DCM, dried (MgSO$_4$), and concentrated. The residue was purified by flash chromatography (120 g SiO$_2$, 0-10% MeOH/DCM) to give the racemic syn-diol (1R,S),(2R,S)-1-(5-methylpyrimidin-2-yl)propane-1,2-diol (5.85 g, 34.8 mmol, 81% yield) as a light yellow solid. $^1$H NMR (300 MHz, CDCl$_3$) δ 8.59 (s, 2H), 4.67 (br. s., 1H), 4.33 (br. s., 1H), 4.09-4.25 (m, 1H), 2.86 (d, J=7.2 Hz, 1H), 2.36 (s, 3H), 1.30 (d, J=6.6 Hz, 3H). MS (ESI pos. ion) m/z: 169.2 (M+H).

Chiral conditions: Prepared a batch of AD-mix-beta from: (26 mg, 0.07 mmol) K$_2$OsO$_2$(OH)$_4$; (16.4 g, 49.9 mmol)

$K_3Fe(CN)_6$; (6.89 g, 49.9 mmol) $K_2CO_3$; (125 mg, 0.16 mmol) $(DHQD)_2PHAL$. In a 50 mL round bottom flask was added t-BuOH (5 mL), water (5.00 mL), and 1.4 g of AD-mix-beta (prepared above) and methanesulfonamide (95 mg, 1.000 mmol). The mixture was stirred at RT until clear and then cooled to 0° C. (E)-5-Methyl-2-(prop-1-en-1-yl) pyrimidine (Intermediate 5.5.1, 168 mg, 1 mmol) in t-BuOH (1 mL) was added and the slurry was stirred at 0° C. 2 h. LCMS (1.5 h) shows 10% conversion. The reaction was warmed slowly to RT as the ice bath melted and stirred an additional 22 h. LCMS showed 90% conversion. The reaction was quenched with saturated aqueous sodium sulfite (10 mL) and extracted with EtOAc (2×20 mL). The combined organic layers were washed with 2 N NaOH (10 mL), dried ($MgSO_4$), and concentrated. The isolated product was only 60 mg of clear oil. LCMS of the aqueous layer showed a large peak corresponding to the desired diol remained in the aqueous layer. The aqueous layer was extracted with DCM (2×50 mL), EtOAc (2×50 mL), and 10% IPA in $CHCl_3$ (2×50 mL). The aqueous layer still showed presence of diol. The combined organic layers were concentrated and the residue purified by flash column chromatography (12 g $SiO_2$, 5-100% 3:1 EtOAc:EtOH/heptane) to give Intermediate 5.5.2 (88.6 mg, 0.527 mmol, 52.7% yield) as a clear, colorless oil. Chiral Analysis: SFC Chiral Analysis shows the % ee to be 94.8% using a AS-H (100×2.1 mm, 3 um), 10% organic modifier (iPrOH with 20 mM ammonia), 90% carbon dioxide. F=1.0 mL/min, column temp=RT, BRP=105 bar,

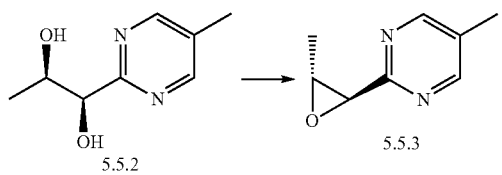

5-Methyl-2-((2R,3R)-3-methyloxiran-2-yl)pyrimidine, intermediate 5.5.3, To a solution of Intermediate 5.5.2 (1.46 g, 8.68 mmol) in DCM (25 mL) (cooled with a RT water bath) was added 1,1,1-trimethoxyethane (2.50 mL, 2.29 mmol), then chlorotrimethylsilane (2.50 mL, 19.7 mmol) was added in 2 portions 5 min apart. The reaction had a small exotherm on the first portion of addition of TMSCl (23-28° C.). The reaction was stirred at RT under $N_2$ 23 h. LCMS indicated incomplete conversion. An additional 1.25 equiv. of 1,1,1-trimethoxy ethane (1.25 mL, 9.95 mmol) and chlorotrimethylsilane (1.25 mL, 9.85 mmol) were added, and the reaction was stirred an additional 24 h. LCMS (24 h) showed 75% conversion to chloroacetate (M+H=229). The reaction was concentrated in vacuo. The residue was dissolved in MeOH (20 mL) and potassium carbonate (1.500 g, 10.85 mmol) was added. The reaction was then stirred at RT for 4 h. LCMS (4 h) showed complete conversion to product corresponding to the desired epoxide (M+H=151) with some residual orthoacetate (M-OMe+H2O=211) with the same retention time as the product. The reaction was filtered, the filter cake washed with DCM (5 mL), and the combined filtrates concentrated in vacuo. The reaction product was purified by flash column chromatography on silica gel eluting with 0-100% EtOAc/hexanes) to afford Intermediate 5.5.3 (1.00 g, 6.6 mmol, 77%) as a clear, light yellow oil. $^1$H NMR (300 MHz, $CDCl_3$) δ 8.54 (s, 2H), 3.81 (d, J=1.9 Hz, 1H), 3.32-3.53 (m, 1H), 2.31 (s, 3H), 1.50 (d, J=5.1 Hz, 3H). MS (LSI pos. ion) m/z: 151.2 (M+H).

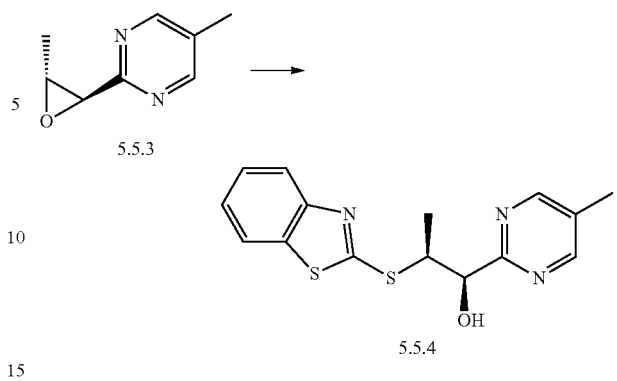

(1R,2S)-2-(Benzo[d]thiazol-2-ylthio)-1-(5-methylpyrimidin-2-yl)propan-1-ol, Intermediate 5.5.4, To a solution of Intermediate 5.5.3 (250 mg, 1.332 mmol) in DCM (5 mL) was added benzo[d]thiazole-2-thiol (245 mg, 1.465 mmol), followed by tris(((trifluoromethyl)sulfonyl)oxy)ytterbium (83 mg, 0.133 mmol). The suspension was heated in a 35° C. heating block 17 h, after 10 min, the reaction became a clear, colorless solution. LCMS (1 h) showed 80% conversion to a peak corresponding to the mass of desired product (M+H=318). LCMS (17 h) showed 100% conversion to desired product. The reaction was cooled to RT and then loaded on a plug of silica and purified by flash chromatography (12 g $SiO_2$, 5-100% 3:1 EtOAc:EtOH/heptane) to afford Intermediate 5.5.4 (428 mg, 1.348 mmol, 101% yield) as a clear, colorless oil. $^1$H NMR (300 MHz, $CDCl_3$) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). MS (ESI pos. ion) m/z: 318.2 (M+H).

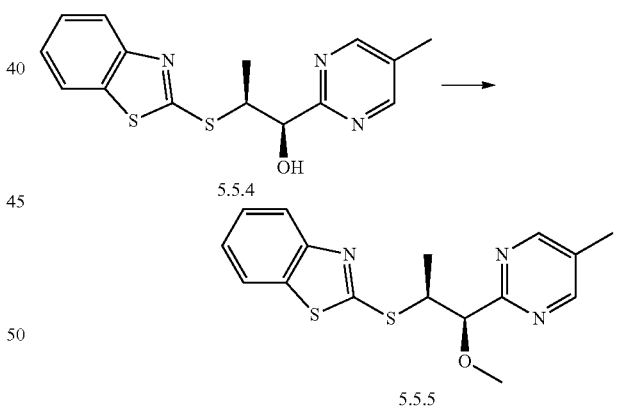

2-(((1R,2S)-1-Methoxy-1-(5-methylpyrimidin-2-yl)propan-2-yl)thio)benzo[d]thiazole, Intermediate 5.5.5, To a 50 mL flask equipped with a magnetic stirrer was charged a solution of racemic Intermediate 5.5.4 (350 mg, 1.103 mmol) in 2-MeTHF (1.1 mL). The reaction mixture was cooled to −78° C. and potassium bis(trimethylsilyl)amide, (1M solution in THF, 1.32 μL, 1.32 mmol) was added dropwise (total addition time: 2 min, turned to a yellow solution). The resulting mixture was stirred for 1 h and then methyl trifluoromethanesulfonate (374 μl, 3.31 mmol) was added dropwise (turned a lighter yellow solution). The reaction mixture was stirred at −78° C. for 15 min. LCMS showed complete conversion of starting material to the product. The reaction mixture was quenched with saturated aqueous NH$_4$Cl solution (30 mL) at −78° C. The reaction was then warmed to RT and the aqueous layer was back extracted with EtOAc (3×75 mL). The combined organic layers were washed with brine, dried (Na$_2$SO$_4$), and concentrated. The material obtained was purified by chromatography through a Biotage 50 g ultra silica gel column, eluting with a gradient of 0% to 25% EtOAc in hexane, to provide Intermediate 5.5.5 (0.32 g, 75%) as a light-yellow oil.

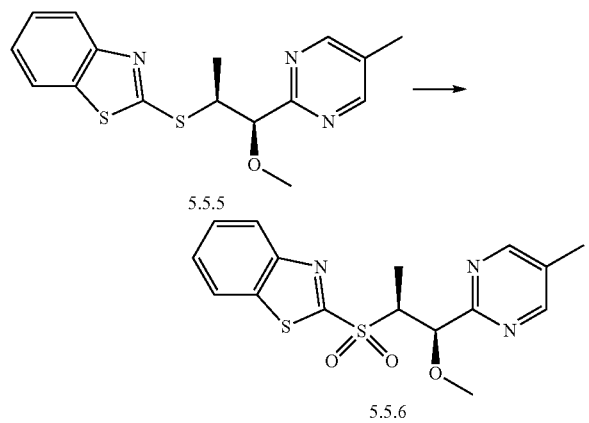

2-(((1R,2S)-1-Methoxy-1-(5-methylpyrimidin-2-yl)propan-2-yl)sulfonyl)benzo[d]thiazole, Intermediate 5.5.6. A solution of Intermediate 5.5.5 (313 mg, 0.944 mmol) in DCM (2.8 mL) at 0° C. was treated with 3-chloroperoxybenzoic acid, (77% max, 476 mg, 2.125 mmol). The reaction was stirred at 0° C. for 1 h before the ice bath was removed. LCMS showed desired product, sulfoxide, and the presumed sulfoxide/sulfone. The mixture was allowed to warm to RT and was stirred for an additional 40 h. The reaction was quenched with saturated aqueous sodium bisulfite (6 mL), followed by addition of saturated aqueous sodium bicarbonate (5 mL) and the resulting mixture was stirred for 10 min. The reaction was extracted with EtOAc (2×20 mL) and the organic layers combined, washed with saturated aqueous NaHCO$_3$ (10 mL), brine (10 mL), dried (MgSO$_4$) and filtered. Iodide/starch strip indicator shows no peroxide present. The filtrates were concentrated to give a clear, colorless oil (360 mg). Purification of the residue by flash chromatography (40 g SiO$_2$, 0-100% 3:1 EtOAc:EtOH/heptane) gave Intermediate 5.5.6 (285 mg, 0.784 mmol, 83% yield, 77% purity) as a white foam. $^1$H NMR (300 MHz, CDCl$_3$) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=1.2 Hz, 3H). MS (ESI pos. ion) m/z: 364.0 (M+H).

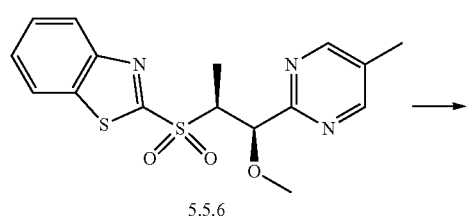

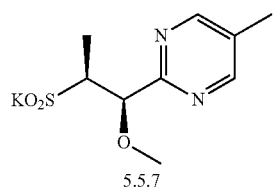

Potassium (1R,2S)-1-methoxy-1-(5-methylpyrimidin-2-yl)propane-2-sulfinate, Intermediate 5.5.7, To a solution of racemic Intermediate 5.5.6 (268 mg, 0.74 mmol) in MeOH (1.84 mL) was added potassium carbonate (204 mg, 1.48 mmol). The reaction was stirred at RT for 17 h. LCMS showed desired Intermediate 5.5.7, The reaction was concentrated in vacuo (yellow solid) and used directly in the following step. Epimerization occurred in this reaction (~15%).

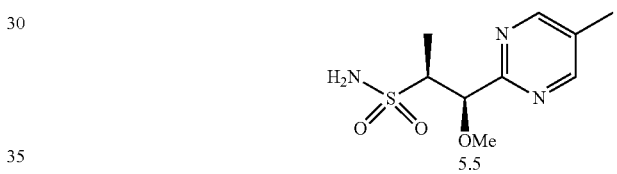

(1R,2S)-1-methoxy-1-(5-methylpyrimidin-2-yl)propane-2-sulfonamide, Intermediate 5.5. To a suspension of Intermediate 5.5.7 (198 mg, 0.738 mmol) in water (3.7 mL) was added potassium acetate (72.4 mg, 0.738 mmol), followed by hydroxylamine-o-sulfonic acid, 97% (167 mg, 1.476 mmol). The reaction mixture was stirred at RT for 4.5 h. LCMS showed desired product formation plus a small peak that corresponded to the stereoisomer. The reaction mixture was extracted with EtOAc (2×) and the organics were combined, dried (Na$_2$SO$_4$), and concentrated. The residue was loaded onto a silica gel column eluting with 0-30% (3:1 EtOAc:EtOH)/DCM to afford Intermediate 5.5 (114 mg, 0.465 mmol, 63.0% yield) as a white solid, (contained 15% other diastereomer). $^1$H NMR (300 MHz, CDCl$_3$) δ 8.63 (s, 2H), 5.10 (d, J=3.3 Hz, 1H), 4.78 (br. s., 2H), 3.74 (qd, J=7.1, 3.3 Hz, 1H), 3.51 (s, 3H), 2.36 (s, 3H), 1.33 (d, J=7.1 Hz, 3H). MS (ESI pos. ion) m/z: 246.1 (M+H).

Intermediate 5.6. Preparation of (R)-1-(5-fluoropyrimidin-2-yl)propane-2-sulfonamide and (S)-1-(5-fluoropyrimidin-2-yl)propane-2-sulfonamide

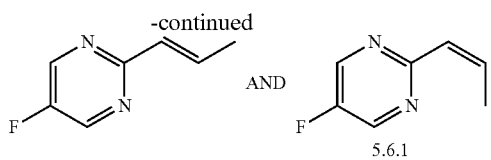

5.6.1

(E)-5-Fluoro-2-(prop-1-en-1-yl)pyrimidine and (Z)-5-fluoro-2-(prop-1-en-1-yl)pyrimidine, Intermediate 5.6.1, To magnesium turnings (9.0 g, 371.9 mmol) was added 1-2 crystals of iodine under anhydrous conditions. The mixture was heated at 60° C. for 5 min under reduced pressure to activate the magnesium. The flask was then cooled to RT and THF (370 mL) was added. The resulting mixture was heated to 65° C., (Z/E)-1-bromo-1-propene (45 g, 371.9 mmol) was added dropwise, and the mixture was then stirred at 65° C. for 2 h under nitrogen atmosphere. Thereafter, the mixture was cooled to RT and transferred to an ice bath. Zinc chloride (1M in diethyl ether, 283 mL, 283 mmol) was then added dropwise over 10 min (The internal temperature of the reaction was kept ~10° C.-15° C. dining the addition) and the resulting organozinc reagent was stirred at RT for 45 min. In a separate round bottom flask, a solution of 2-chloro-5-fluoropyrimidine (commercially available from Novochemy, Jupiter, FL, USA) (25 g, 189 mmol), S-phos (7.7 g, 18.8 mmol) and palladium (II) acetate (2.1 g, 9.4 mmol) in THF (38 mL) was degassed with nitrogen gas for 5 min. The organozinc reagent was then added dropwise. The resulting mixture was heated at 60° C. for 12 h. After completion of reaction (monitored by TLC), the reaction mixture was quenched with water (50 mL) and acidified with 1N hydrochloric acid (700 mL) pH ~2. The mixture was then extracted with diethyl ether (2×500 mL). The combined organic layers were washed with brine (200 mL), dried over sodium sulphate and concentrated under reduced pressure at 20° C. to a volume of approximately 50 mL, which was used as in the next step without further purification.

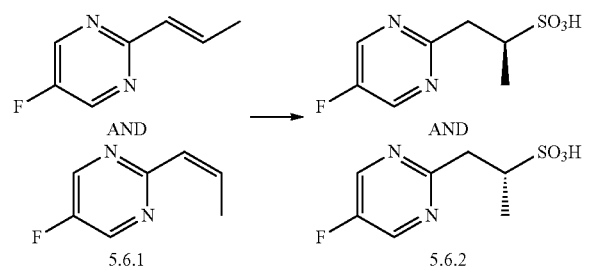

(S)-1-(5-Fluoropyrimidin-2-yl)propane-2-sulfonic acid and (R)-1-(5-fluoropyrimidin-2-yl)propane-2-sulfonic acid, Intermediate 5.6.2, To a solution of Intermediate 5.6.1 (188.6 mmol) in THF (ca. 50 mL) was added an aqueous solution of sodium bisulfite (19.6 g, 188.6 mmol in 100 mL of H$_2$O). The reaction mixture was stirred at RT for 20 h. Once the reaction was complete (monitored by TLC), the mixture was acidified to approximately pH1 with concentrated HCl (10 mL). The aqueous layer was then concentrated under reduced pressure to furnish the product which was suspended in EtOH (250 mL). The product was heated to reflux, filtered hot and rinsed with hot EtOH (100 mL). The filtrate was concentrated under reduced pressure to give a brown solid which was recrystallized from IPA (50 mL) to afford Intermediate 5.6.2 (20 g, 48%) as a brown solid. $^1$H NMR (400 MHz, D$_2$O) δ 8.69 (s, 2H), 3.47 (td, J=9.8, 8.2, 4.0 Hz, 2H), 3.06 (dd, J=16.1, 10.2 Hz, 1H), 1.24 (d, J=6.5 Hz, 3H). MS-ESI (neg.) m/z: 118.9 (M−H)$^-$.

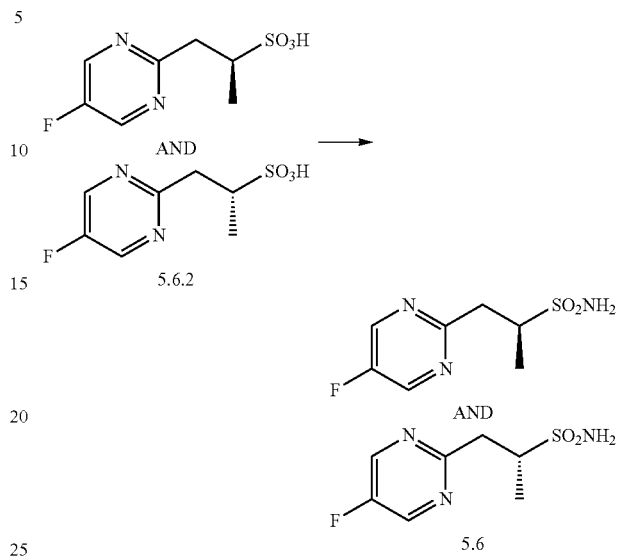

(R)-1-(5-Fluoropyrimidin-2-yl)propane-2-sulfonamide and (S)-1-(5-fluoropyrimidin-2-yl)propane-2-sulfonamide, Intermediate 5.6. A solution of Intermediate 5.6.2 (80 g, 360 mmol) in thionyl chloride (268 mL, 3600 mmol) was heated at 60° C. for 3 h. The reaction was concentrated under reduced pressure to afford the sulfonyl chloride, which was azeotroped with toluene (3×300 mL). The residue was diluted with DCM (1.0 L) and ammonia gas was bubbled through for 15 min at −78° C. The mixture was then stirred at RT for 1 h. Thereafter, the reaction mixture was filtered through a pad of Celite® filter aid and the pad was washed with DCM (100 mL) and EtOAc (100 mL). The combined filtrate was then concentrated under reduced pressure to obtain the material, which was purified by column chromatography (silica; 100-200, elution 0-60% EtOAc in hexane) to give Intermediate 5.6 (43 g, 54%) as a white solid. $^1$H NMR (400 MHz, DMSO-d6) δ 8.86 (d, J=1.1 Hz, 2H), 6.90 (s, 2H), 3.57-3.51 (m, 2H), 2.93 (dd, J=15.4, 11.1 Hz, 1H), 1.19 (d, J=6.5 Hz, 3H). MS-ESI (pos.) m/z: 220.0 (M+H)$^+$.

Intermediate 5.7. Preparation of (1S,2S)-1-(5-fluoropyrimidin-2-yl)-1-isopropoxypropane-2-sulfonamide

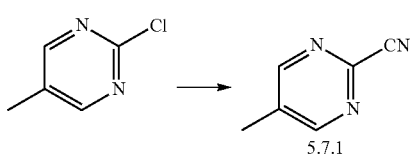

5-Methylpyrimidine-2-carbonitrile, Intermediate 5.7.1. A solution of 2-chloro-5-methylpyrimidine (500 g, 3889 mmol, 1.0 equiv) in DMF (5.0 L) was degassed with N$_2$ for 20 min and dppf (108 g, 194 mmol, 0.05 equiv) and Pd$_2$(dba)$_3$ (178 g, 194 mmol, 0.05 equiv) were added to the reaction mixture. Zn(CN)$_2$ (685 g, 5834 mmol, 1.5 equiv) was added, and the reaction mixture was heated at 100° C.

for 16 h. The reaction was quenched with water (5.0 L) and stirred for 10 min. The reaction mixture was then filtered through a pad of Celite® brand filter agent. The filtrate was diluted with water (4.0 L) and extracted with EtOAc (2×4.0 L). The combined organic layers were washed with brine (4 L), dried over Na₂SO₄, filtered, and concentrated under reduced pressure to give the product which was further purified by column chromatography using silica gel (60-120 mesh) and 0-10% EtOAc in hexanes to obtain Intermediate 5.7.1 (330 g, 71%) as off white solid. $^1$H NMR (400 MHz, DMSO-d$_6$) δ 8.89 (s, 2H), 2.39 (s, 3H).

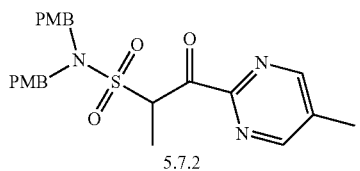

N,N-Bis(4-methoxybenzyl)-1-(5-methylpyrimidin-2-yl)-1-oxopropane-2-sulfonamide, Intermediate 5.7.2, To a solution of Intermediate 5.8 (293 g, 839 mmol, 2.0 equiv) in THF (2.0 L) was added isopropylmagnesium chloride (420 mL, 839 mmol, 2.0 equiv, 2.0 M in diethyl ether) at 0° C. The reaction mixture was stirred at 25° C. for 3 h. To the reaction mixture was added 5-methylpyrimidine-2-carbonitrile (50 g, 420 mmol, 1.0 equiv) in THF (100 mL) at 0° C. The resulting mixture was then stirred at RT for 2 h. The reaction was quenched with 1.5 N HCl (500 mL), and water (2.0 L) was added. The resulting mixture was then stirred for 10 min. The mixture was extracted with EtOAc (2×1 L) and the combined organic layers were washed with brine (500 mL), dried over Na₂SO₄ and filtered. The organic layer was concentrated under reduced pressure to provide the compound which was purified by column chromatography using silica gel (100-200 mesh) and 0-50% EtOAc in hexanes as eluent to obtain Intermediate 5.7.2 (60 g, 30% yield) as a brown liquid. $^1$H NMR (400 MHz, DMSO-d$_6$) δ 8.90 (s, 2H), 7.15-7.09 (m, 4H), 6.85-6.80 (m, 4H), 4.34-4.18 (m, 5H), 3.71 (app s, 6H), 2.39 (s, 3H), 1.50 (d, J=6.9 Hz, 3H). MS (ESI+ve ion) m/z: (M+H)$^+$: 470.0.

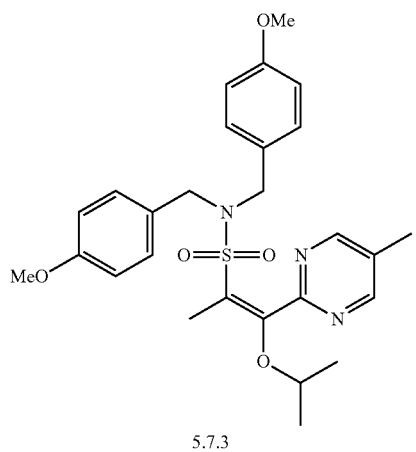 [SMILES: COc1ccc(CN(Cc2ccc(OC)cc2)S(=O)(=O)/C(C)=C(/OC(C)C)c2ncc(C)cn2)cc1]

(E)-1-Isopropoxy-N,N-bis(4-methoxybenzyl)-1-(5-methylpyrimidin-2-yl)prop-1-ene-2-sulfonamide, Intermediate 5.7.3, To a solution of Intermediate 5.7.2 (120 g, 256 mmol, 1.0 equiv) in DMF (1.2 L) was added 2-iodopropane (129 mL, 1278 mmol, 5.0 equiv) and potassium carbonate (70.6 g, 511 mmol, 2.0 equiv). The reaction mixture was then stirred at 60° C. for 14 h. The reaction was quenched with water (1.0 L), stirred for 10 min, and extracted with EtOAc (2×1 L). The combined organic layers were washed with brine (1 L), dried over Na₂SO₄, filtered and concentrated under reduced pressure to give the material. The product thus obtained was purified by column chromatography using silica gel (100-200 mesh) and 0-50% EtOAc in hexanes as eluent to obtain Intermediate 5.7.3 (75 g, 57.4% yield) as an off white solid. $^1$H NMR (400 MHz, DMSO-d$_6$) δ 8.72 (s, 2H), 7.09 (d, J=8.3 Hz, 4H), 6.86 (d, J=8.3 Hz, 4H), 4.16 (s, 4H), 3.73 (s, 3H), 3.73 (s, 3H), 3.71-3.67 (m, 1H), 2.31 (s, 3H), 1.87 (s, 3H), 1.19-1.16 (m, 6H). MS (ESI+ve ion) m/z: (M+H)$^+$: 512.1.

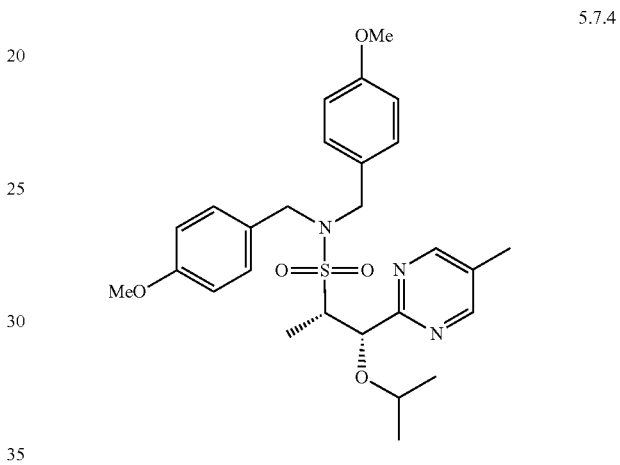

(1S,2R)-1-Isopropoxy-N,N-bis(4-methoxybenzyl)-1-(5-methylpyrimidin-2-yl)propane-2-sulfonamide, Intermediate 5.7.4, To a solution of Intermediate 5.7.3 (180 g, 352 mmol, 1.0 equiv) in MeOH (1.8 L) was added zinc triflate (256 g, 704 mmol, 2.0 equiv) and (S)—RuCl[(p-cymene(BINAP)]Cl (6.54 g, 7.04 mmol, 0.02 equiv). The resulting mixture was then heated at 60° C. under H₂ pressure (60 psi) for 16 h. The reaction mixture was concentrated under reduced pressure to obtain an initial product which was further purified by column chromatography using silica gel (60-120 mesh) and 0-50% EtOAc in DCM as eluent to obtain Intermediate 5.7.4 (140 g, 77%, 92% ee) as an off white solid. $^1$H NMR (400 MHz, DMSO-d$_6$) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (app s, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). MS (ESI+ve ion) m/z: (M+H)$^+$: 514.2.

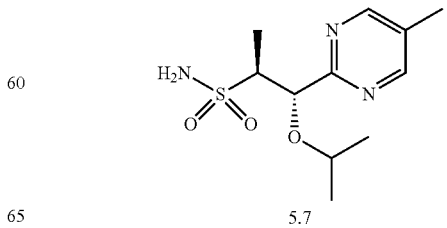

(1S,2S)-1-Isopropoxy-1-(5-methylpyrimidin-2-yl)propane-2-sulfonamide, Intermediate 5.7. To a solution of Intermediate 5.7.4 (140.0 g, 273 mmol, 1.0 equiv) in DCM (500 mL) was added TFA (250 mL) at 0° C. The resulting reaction mixture was then stirred at RT for 16 h. Next, the reaction mixture was concentrated under reduced pressure, dissolved in DCM (1.0 L) and washed with a saturated aqueous NaHCO$_3$ solution (1.0 L). The organic layer was dried over Na$_2$SO$_4$, filtered and concentrated under reduced pressure to obtain the initial material which was further purified by column chromatography using silica gel (60-120 mesh) and 0-2% MeOH in DCM to obtain Intermediate 5.7 (72 g, 97% yield, 90% ee) as an off white solid. Intermediate 5.7 (72 g, 90% ee) was suspended in IPA (500 mL) and heated to 70° C. until the mixture became homogeneous. Once the solution became homogeneous, the mixture was cooled to RT overnight. The white solid thus obtained was filtered, dried under vacuum to obtain Intermediate 5.7 (30 g, >99%). The mother liquor was concentrated, and the solid obtained was recrystallized again utilizing the same procedure. $^1$H NMR (400 MHz, DMSO-d$_6$) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). MS (ESI+ve ion) m/z: (M+H)$^+$: 274.1.

Intermediate 5.8: Preparation of
N,N-bis(4-methoxybenzyl)ethanesulfonamide

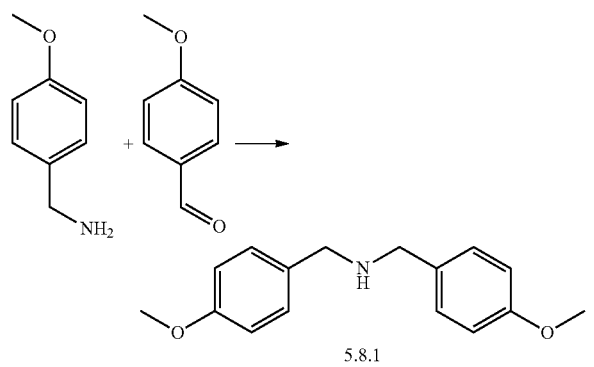

Bis(4-methoxybenzyl)amine, Intermediate 5.8.1. 4-Methoxybenzylamine (neat, 600 g, 4.37 mol, 1 eq) and 4-methoxybenzaldehyde (532 mL, 4.37 mol, 1 eq) were added to a 10 L round bottomed flask at RT with stirring. The reaction spontaneously warmed and a white precipitate was observed. The mixture was stirred for 1 h. To the above mixture was added anhydrous EtOH (4.8 L) and stirring was continued at RT for 15-30 min. This was followed by the addition of sodium borohydride granules (99 g, 2.62 mol, 0.6 eq) portionwise over ~2 h. During the addition of NaBH$_4$, the internal temperature of the reaction rose to 42° C. The resulting mixture was then stirred at RT overnight. Next, the reaction was quenched slowly with water (600 mL). The mixture was then concentrated on a rotary evaporator at 50° C. The residue was partitioned between water (4 L) and DCM (4 L). The aqueous layer was extracted with more DCM (2×2 L). The combined organic layers were dried over Na$_2$SO$_4$, filtered and concentrated in vacuo to give Intermediate 5.8.1 (1112 g, 99% yield) as a semi-solid. The material was used directly in the next step without further purification. $^1$H-NMR (400 MHz, CDCl$_3$) δ 7.28 (t, J=7.12 Hz, 4H), 6.89 (d, J=8.60 Hz, 4H), 3.83 (app s, 6H), 3.76 (s, 4H) (—NH proton not observed). MS (ESI pos. ion) m/z: =258.4 (M+H)$^+$.

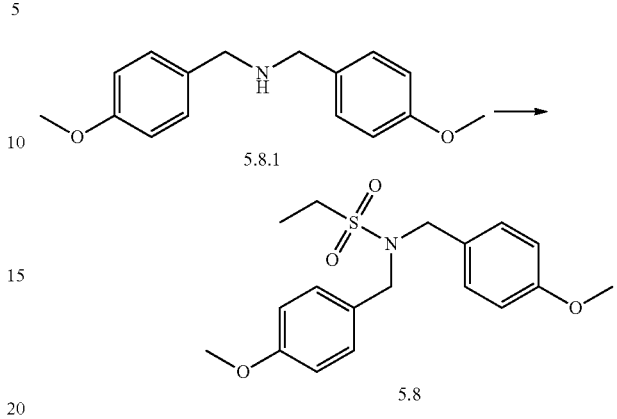

N,N-Bis(4-methoxybenzyl)ethanesulfonamide, Intermediate 5.8. To a solution of bis(4-methoxybenzyl)amine Intermediate 5.8.1 (900 g, 3.49 mol, 1 eq) in DCM (9 L) was added TEA (634 mL, 4.55 mol, 1.3 eq), followed by dropwise addition of ethanesulfonyl chloride (399 mL, 4.19 mol, 1.2 eq). The internal temperature was kept between 5-10° C. during the addition of the ethane sulfonyl chloride. Once the addition was complete, the cooling bath was removed. After 1.5 h, TLC showed complete loss of starting material. The reaction was quenched by the addition of water (4 L) to the reaction mixture. The layers were separated and the aqueous layer extracted with DCM (2×2 L). The combined organic layers were washed with brine (2×1 L), dried over Na$_2$SO$_4$, and concentrated in vacuo. The material thus obtained was adsorbed onto a plug of silica gel and purified by chromatography (silica gel (60-120 mesh) eluting with a gradient of 10-80% EtOAc in hexanes) to provide the title compound Intermediate 5.8 (1125 g, 3.22 mol, 92%) as a white solid. $^1$H-NMR (400 MHz, CDCl$_3$) δ 7.23 (dd, J=2.08, 6.62 Hz, 4H), 6.90 (dd, J=2.12, 6.60 Hz, 4H), 4.29 (s, 4H), 3.83 (app s, 6H), 2.92 (q, J=7.40 Hz, 2H), 1.33 (t, J=7.40 Hz, 3H). GC-MS (ESI pos. ion) m/z: =372.2 (M+Na)$^+$.

Biological Activity
[$^{35}$S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, MgCl$_2$, and NaCl in the assay buffer were initially determined. The assay was performed in 9 μL assay buffer [20 mM HEPES, pH 7.5, 5 mM MgCl$_2$, 100 mM NaCl and 0.1% (w/v) BSA], 1 μL of diluted test compound (starting with 0.75 mM, 2-fold serial dilution with DMSO, total 22 points), 10 μL of 18 μM GDP (final concentration of 3 μM GDP), 20 μL of 0.25 μg/m L membrane protein expressing human APJ receptor captured with WGA PS beads (final concentration of 5 μg per well), and 20 μL of 0.3 nM [$^{35}$S]GTPγS (final concentration is 0.1 nM [$^{35}$S]GTPγS)(Perkin Elmer Life and Analytical Sciences, Waltham USA). One column of the plate was 1 μL of DMSO as background and another column of the plate was 1 μL of 180 μM Pyr-Apelin-13 which was used as control at a final concentration of 3 μM. Incubation was at RT for 90 min and the microplate was read using a ViewLux™ ultra HTS Microplate Imager (PerkinElmer, Inc.). All the results presented are means of several independent experiments and analyzed by non-linear regression methods using the commercially available program Prism (GraphPad, San Diego, Calif.) providing the $EC_{50}$ values detailed in Table 3.

The following table includes biological activity data obtained using the procedures and assays set forth above for the Example compounds described herein.

TABLE 3

Biological Activity Information for Example Compounds.

| Example | Activity hAPJ SPA $EC_{50}$ IP (nM) |
|---|---|
| 4.0 | 30 |
| 4.1 | 745 |
| 4.2 | 27 |
| 4.3 | 194 |
| 4.4a | 244 |
| 4.4b | 193 |
| 4.5 | 11 |
| 4.6 | 20 |
| 4.7 | 78 |
| 4.8 | 86 |
| 4.9 | 193 |
| 4.10 | Prophetic |
| 4.11 | Prophetic |
| 4.12 | Prophetic |
| 4.13 | Prophetic |
| 4.14 | Prophetic |
| 4.15 | Prophetic |
| 4.16 | Prophetic |
| 4.17 | 2.8 |
| 4.18 | Prophetic |
| 4.19 | Prophetic |
| 4.20 | Prophetic |
| 4.21 | Prophetic |
| 4.22 | Prophetic |
| 4.23 | Prophetic |
| 4.24 | 1.5 |
| 4.25 | Prophetic |
| 4.26 | Prophetic |
| 4.27 | Prophetic |
| 4.28 | Prophetic |
| 4.29 | Prophetic |
| 4.30 | Prophetic |
| 4.31 | Prophetic |
| 4.32 | Prophetic |

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun., 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sim, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117(2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of the APJ pathway resulted in positive cooperativity of AngII by shifting its potency to the left and also increasing the efficacy of the IP response (see methods and results section below). Conversely, blocking the AT1R receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signalling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor such as captopril which may play an important role in providing greater efficacy in treating heart failure patients, for example in improving contractility and ejection fraction without changing the heart rate.

Evidence for Allosteric Interaction Between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F12 and 10% FBS at a density of 15 k/well in a 96 well plate overnight. The next day, the culture medium was replaced with medium containing no serum for 4 hours. The compound AngII at a range of concentrations (1 pM-10 μM) with or without different concentrations of APJ agonists were diluted in stimulation buffer and added to the cell plate. The plate was sealed and incubated for 1 hour. This was followed by addition of IP-d2 conjugate followed by europium cryptate antibody conjugate into the wells. The plate was sealed, followed with incubation for 2 hours at RT. Time-resolved fluorescence resonance energy (TR-FRET) at 620 nm and 665 nm was measured after 2 horns with an Envision reader. The signal ratios and delta F were calculated and the amount of IP1 produced was inversely proportional to the TR-FRET ratio, 665/620 nm.

RESULTS

In cells expressing both APJ and the AT1R receptor, addition of APJ agonists at different concentrations increased the maximal response of AngII and also shifted the potency to the left. The increase in IP1 response reached a maximal effect both in potency and Emax indicating a ceiling effect which is a hallmark for allosteric cooperativity between the AT1R and APJ receptor (FIG. 1). However, this effect of cooperativity was not observed in either APJ or AT1R recombinant stable cell lines indicating that there is functional cross-talk between the two receptors through physical interaction or with downstream effectors (FIG. 2 and FIG. 3). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound of Formula I or Formula II:

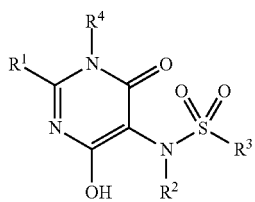

I

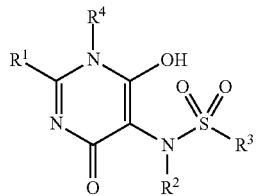

II or a pharmaceutically acceptable salt thereof, a tautomer thereof, a pharmaceutically acceptable salt of the tautomer, a stereoisomer of any of the foregoing, or a mixture thereof, wherein:
$R^1$ is selected from $R^{1a}$, $R^{1b}$, $R^{1c}$, $R^{1d}$, $R^{1e}$, $R^{1f}$, or $R^{1g}$;
$R^{1a}$ is an unsubstituted $C_1$-$C_8$ straight or branched chain alkyl or $R^{1a}$ is a $C_1$-$C_8$ straight or branched chain alkyl substituted with 1, 2, or 3 $R^{1a'}$ substituents;
$R^{1b}$ is an unsubstituted monocyclic $C_3$-$C_8$ cycloalkyl, an unsubstituted $C_5$-$C_8$ polycyclic cycloalkyl, an unsubstituted monocyclic $C_4$-$C_8$ cycloalkenyl, a monocyclic $C_3$-$C_8$ cycloalkyl substituted with 1, 2, 3, or 4 $R^{1b'}$ substituents, a $C_5$-$C_8$ polycyclic cycloalkyl substituted with 1, 2, or 3 $R^{1b'}$ substituents, or a monocyclic $C_4$-$C_8$ cycloalkenyl substituted with 1, 2, or 3 $R^{1b'}$ substituents;
$R^{1c}$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1c'}$ substituents;
$R^{1d}$ is a phenyl group that is unsubstituted or is substituted with 1, 2, or 3 $R^{1d'}$ substituents;
$R^{1e}$ is an unsubstituted furanyl, or is a furanyl substituted with 1, 2, or 3 $R^{1e'}$ substituents;
$R^{1f}$ is a 5- or 6-membered heteroaryl group that is unsubstituted or is substituted with 1, 2, or 3 $R^{1f}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;
$R^{1g}$ is an unsubstituted pyridyl, pyridonyl, or pyridine N-oxide, or is a pyridyl, pyridonyl, or pyridine N-oxide substituted with 1, 2, 3, or 4 $R^{1g'}$ substituents;
$R^{1a'}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a'}$ groups that include a $C_6$-$C_{10}$ aryl group, the heteroaryl of any of the $R^{1a'}$ groups that include a heteroaryl group, the $C_3$-$C_8$ cycloalkyl of any of the $R^{1a'}$ groups that include a —$C_3$-$C_8$ cycloalkyl group, and the heterocyclyl of any of the $R^{1a'}$ groups that include a heterocyclyl group are unsubstituted or are substituted with 1, 2, or 3 $R^{1a''}$ substituents; and further wherein the $C_3$-$C_8$ cycloalkyl of any of the $R^{1a'}$ groups that include a —$C_3$-$C_8$ cycloalkyl group, and the heterocyclyl of any of the $R^{1a'}$ groups that include a heterocyclyl group may additionally be substituted with 1 or 2 oxo substituents, and the S atom of the heterocyclyl of any of the $R^{1a'}$ groups that include a heterocyclyl group may contain one or two oxo substituents, and still further wherein, the heteroaryl of any of the $R^{1a'}$ groups that include a heteroaryl group may include an N-oxide if the heteroaryl includes a N heteroatom;

$R^{1a'''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1b'}$ in each instance is independently selected from —F, —Cl, —Br, —I, —CN, —OH, =O, —O—($C_1$-$C_6$ alkyl), —O—($C_1$-$C_6$ haloalkyl), perhaloalkyl), —$C_1$-$C_6$ alkyl, —$C_1$-$C_6$ haloalkyl, perhaloalkyl, alkenyl, =$CH_2$, =CH—($C_1$-$C_6$ alkyl), —($C_1$-$C_6$ alkyl)-OH, alkyl)-O—($C_1$-$C_6$ alkyl), —($C_1$-$C_6$ haloalkyl)-OH, haloalkyl)-O—($C_1$-$C_6$ alkyl), —($C_1$-$C_6$ perhaloalkyl)-OH, perhaloalkyl)-O—($C_1$-$C_6$ alkyl), —O—($C_1$-$C_6$ alkyl)-OH, alkyl)-O—($C_1$-$C_6$ alkyl), —O—($C_1$-$C_6$ haloalkyl)-OH, $C_6$ haloalkyl)-O—($C_1$-$C_6$ alkyl), —O—($C_1$-$C_6$ perhaloalkyl)-OH, perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a phenyl group, or a monocyclic heteroaryl group with 5 or 6 ring members containing 1, 2, or 3 heteroatoms independently selected from N, O, or S, wherein the $R^{1b'}$ phenyl and $R^{1b'}$ heteroaryl groups are unsubstituted or are substituted with 1, 2, or 3, $R^{1b''}$ substituents; and further wherein two $R^{1b'}$ groups on a single carbon atom of a monocyclic $C_3$-$C_8$ cycloalkyl $R^{1b}$ group may join together with the carbon atom to which they are attached to form a heterocyclic ring having 3 to 6 members of which 1 or 2 are heteroatoms independently selected from O, N, and S;

$R^{1b''}$ is in each instance, independently selected from —F, —Cl, —Br, —I, —CN, —OH, O—($C_1$-$C_6$ alkyl), —O—($C_1$-$C_6$ haloalkyl), perhaloalkyl), —$C_1$-$C_6$ alkyl, —$C_1$-$C_6$ haloalkyl, perhaloalkyl, alkenyl, alkyl)-OH, alkyl)-O—($C_1$-$C_6$ alkyl), —($C_1$-$C_6$ haloalkyl)-OH, haloalkyl)-O—($C_1$-$C_6$ alkyl), —($C_1$-$C_6$ perhaloalkyl)-OH, perhaloalkyl)-O—($C_1$-$C_6$ alkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, haloalkyl)-O—($C_1$-$C_6$ alkyl), —O—($C_1$-$C_6$ perhaloalkyl)-OH, perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl);

$R^{1c'}$ in each instance is independently selected from —F, —Cl, —Br, —I, —$C_1$-$C_6$ alkyl, —$C_1$-$C_6$ haloalkyl, perhaloalkyl, alkyl)-O—($C_1$-$C_6$ alkyl), —CN, —OH, —O—($C_1$-$C_6$ alkyl), —O—($C_1$-$C_6$ haloalkyl), perhaloalkyl), alkenyl, alkyl)-OH, alkyl)-O—($C_1$-$C_6$ alkyl), —O—($C_1$-$C_6$ haloalkyl)-OH, haloalkyl)-O—($C_1$-$C_6$ alkyl), —O—($C_1$-$C_6$ perhaloalkyl)-OH, perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1c'}$ may also be oxo unless $R^{1c}$ is a 6-membered heterocyclic group that includes one N atom and includes at least one double bond, and further wherein two $R^{1c'}$ substituents on adjacent carbon atoms or on an adjacent carbon atom and an adjacent N atom of a 5- or 6-membered heterocyclic $R^{1c}$ group may join to form a 6 membered ring that may be saturated, partially saturated, or aromatic and may include 0, 1, or 2 N atoms and may further optionally be substituted with 1 or 2 $R^{1c''}$ substituent and may include an oxo substituent if the ring is not an aromatic ring and further wherein two $R^{1c'}$ substituents on adjacent carbon atoms or on an adjacent carbon atom and an adjacent N atom of a 5- or 6-membered heterocyclic $R^{1c}$ group may join to form a 5 membered ring that may be saturated, partially saturated, or aromatic and may include 0, 1, or 2 heteroatoms selected from N, O, or S and may further optionally be substituted with 1 or 2 $R^{1c''}$ substituent and may include an oxo substituent if the ring is not an aromatic ring;

$R^{1c''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl, alkyl)-O—($C_1$-$C_6$ alkyl), —CN, —OH, —O—($C_1$-$C_6$ alkyl), —O—($C_1$-$C_6$ haloalkyl), perhaloalkyl), —$C_2$-$C_6$ alkenyl, alkyl)-OH, alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R_{1d'}$ in each instance is independently selected from —F, —Cl, —Br, —I, —$C_1$-$C_6$ alkyl, —$C_1$-$C_6$ haloalkyl, —$C_1$-$C_6$ perhaloalkyl, alkyl)-OH, haloalkyl)-OH, perhaloalkyl)-OH, alkyl)-O—($C_1$-$C_6$ alkyl), —CN, —OH, —O—($C_1$-$C_6$ alkyl), —O—($C_1$-$C_6$ haloalkyl), perhaloalkyl), —$C_2$-$C_6$ alkenyl, alkyl)-OH, alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, -Q=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, or —O— phenyl, wherein the phenyl of the —O-phenyl $R^{1d'}$ group may optionally be substituted with 1 or 2 $R^{1d''}$ substituents; and further wherein two $R^{1d'}$ substituents on adjacent carbon atoms of the phenyl $R^{1d}$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1d'''}$ substituent and may include an oxo substituent if the ring is not an aromatic ring;

$R^{1d''}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1d'''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1e'}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), or —C(=O)N($C_1$-$C_6$ alkyl)$_2$;

$R^{1f}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1f''}$ substituents; and further wherein two $R^{1f}$ substituents on adjacent carbon atoms or on an adjacent carbon atom and an adjacent N atom of the 5- or 6-membered heteroaryl $R^{1f}$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1f'}$ substituent and may include an oxo substituent if the ring is not an aromatic ring;

$R^{1f'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1f''}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^{1g'}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_1$-$C_6$ alkyl —OH, —$C_1$-$C_6$ haloalkyl-OH, —$C_1$-$C_6$ perhaloalkyl-OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$ $N(C_1$-$C_6$ alkyl)$_2$, phenyl, —C(=O)-(heterocyclyl), a $C_3$-$C_6$ cycloalkyl group or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

$R^2$ is selected from —H, or $C_1$-$C_4$ alkyl;

$R^3$ is selected from an unsubstituted $C_1$-$C_{10}$ alkyl, a $C_1$-$C_{10}$ alkyl substituted with 1, 2, or 3 $R^{3a}$ substituents, an unsubstituted $C_3$-$C_8$ cycloalkyl, a $C_3$-$C_8$ cycloalkyl substituted with 1, 2, or 3 $R^{3a}$ substituents, a group of formula —(CR$^{3b}$R$^{3c}$)-Q, a group of formula —(CR$^{3d}$R$^{3e}$)—(CR$^{3f}$R$^{3g}$)-Q, a group of formula —(CR$^{3b}$=CR$^{3c}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, -Q, a group of formula —($C_3$-$C_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), $C_2$-$C_6$ alkenyl, $C_2$-$C_6$ alkynyl, —NH$_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, $C_1$-$C_6$ alkyl, $C_1$-$C_6$ haloalkyl, $C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3d}$ and $R^{3g}$ are independently selected from —H, —F, —Cl, —CN, $C_1$-$C_6$ alkyl, $C_1$-$C_6$ haloalkyl, $C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, $C_1$-$C_6$ alkyl, $C_1$-$C_6$ haloalkyl, $C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, $C_1$-$C_6$ alkyl, $C_1$-$C_6$ haloalkyl, $C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^{3h}$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, $C_1$-$C_6$ alkyl, $C_1$-$C_6$ haloalkyl, $C_1$-$C_6$ perhaloalkyl, $C_2$-$C_6$ alkenyl, $C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-NH$_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, $C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Br, —I, —CN, $C_1$-$C_6$ alkyl, $C_1$-$C_6$ haloalkyl, $C_1$-$C_6$ perhaloalkyl, alkyl)-OH, alkyl)-O—($C_1$-$C_6$ alkyl), —OH, —O—($C_1$-$C_6$ alkyl), haloalkyl), perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and $R^{4b}$ in each instance is selected from —F, —Cl, —Br, —I, —CN, —OH, oxo, —O—($C_1$-$C_6$ alkyl), —O—($C_1$-$C_6$ haloalkyl), perhaloalkyl), —S—($C_1$-$C_6$ alkyl), —S—($C_1$-$C_6$ haloalkyl), perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4b}$ group, the 3 to 6 membered heterocyclyl $R^{4b}$ group, the phenyl $R^{4b}$ group, and the a 5 or 6 membered heteroaryl $R^{4b}$ ring are unsubstituted or are substituted with 1 or 2 $R^{4c}$ substituents; and further wherein the 3 to 6 membered cycloalkyl $R^{4b}$ group and the 3 to 6 membered heterocyclyl $R^{4b}$ group may optionally be additionally substituted with an oxo substituent; and $R^{4c}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$.

2. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is $R^{1a}$.

3. The compound of claim 2 or the pharmaceutically acceptable salt thereof, the tautomer thereof, the pharmaceutically acceptable salt of the tautomer, the stereoisomer of any of the foregoing, or the mixture thereof, wherein $R^{1a}$ is an unsubstituted $C_2$-$C_6$ straight or branched chain alkyl or $R^{1a}$ is a $C_1$-$C_6$ straight or branched chain alkyl substituted with 1, 2, or 3 $R^{1a'}$ substituents, wherein $R^{1a'}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl).

4. The compound of claim 3 or the pharmaceutically acceptable salt thereof, the tautomer thereof, the pharmaceutically acceptable salt of the tautomer, the stereoisomer of any of the foregoing, or the mixture thereof, wherein $R^{1a}$ is an unsubstituted $C_2$-$C_6$ straight or branched chain alkyl or $R^{1a}$ is a $C_1$-$C_6$ straight or branched chain alkyl substituted with 1, 2, or 3 $R^{1a'}$ substituents, wherein $R^{1a'}$ in each instance is independently selected from —F, —Cl, —Br, —I, —CN, —OH, —O—($C_1$-$C_6$ alkyl), —O—($C_1$-$C_6$ haloalkyl), or —O—($C_1$-$C_6$ perhaloalkyl).

5. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is $R^{1b}$.

6. The compound of claim 5 or the pharmaceutically acceptable salt thereof, the tautomer thereof, the pharmaceutically acceptable salt of the tautomer, the stereoisomer of any of the foregoing, or the mixture thereof, wherein $R^{1b}$ is an unsubstituted monocyclic $C_3$-$C_8$ cycloalkyl or is a monocyclic $C_3$-$C_8$ cycloalkyl substituted with 1, 2, or 3 $R^{1b'}$ substituents.

7. The compound of claim 6 or the pharmaceutically acceptable salt thereof, the tautomer thereof, the pharmaceutically acceptable salt of the tautomer, the stereoisomer of any of the foregoing, or the mixture thereof, wherein $R^{1b}$ is an unsubstituted monocyclic $C_3$-$C_6$ cycloalkyl or is a monocyclic $C_3$-$C_7$ cycloalkyl substituted with 1 or 2 $R^{1b'}$ substituents, wherein $R^{1b'}$ in each instance is independently selected from —F, —Cl, —Br, —I, —CN, —OH, =O, —O—($C_1$-$C_6$ alkyl), —O—($C_1$-$C_6$ haloalkyl), —O—($C_1$-$C_6$ perhaloalkyl), —$C_1$-$C_6$ alkyl, —$C_1$-$C_6$ haloalkyl, or —$C_1$-$C_6$ perhaloalkyl.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is $R^{1c}$.

9. The compound of claim 8 or the pharmaceutically acceptable salt thereof, the tautomer thereof, the pharmaceutically acceptable salt of the tautomer, the stereoisomer of any of the foregoing, or the mixture thereof, wherein $R^{1c}$ a 5- or 6-membered saturated or partially saturated heterocyclic group that includes 1, 2, or 3 heteroatoms independently selected from N, O, or S that is unsubstituted or is substituted with 1, 2, or 3 $R^{1c'}$ substituents.

10. The compound of claim 8 or the pharmaceutically acceptable salt thereof, the tautomer thereof, the pharmaceutically acceptable salt of the tautomer, the stereoisomer of any of the foregoing, or the mixture thereof, wherein $R^{1c}$ a 5- or 6-membered saturated or partially saturated heterocyclic group that includes 1, 2, or 3 heteroatoms independently selected from N, O, or S that is unsubstituted or is substituted with 1, 2, or 3 $R^{1c'}$ substituents, wherein the substituted or unsubstituted $R^{1c}$ is selected from tetrahydrofuranyl, pyrrolidinyl, tetrahydropyranyl, piperidinyl, piperazinyl, or morpholinyl.

11. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is $R^{1d}$.

12. The compound of claim 11 or the pharmaceutically acceptable salt thereof, the tautomer thereof, the pharmaceutically acceptable salt of the tautomer, the stereoisomer of any of the foregoing, or the mixture thereof, wherein $R^{1d}$ is an unsubstituted phenyl or is a phenyl substituted with 1 or 2 $R^{1d'}$ substituents, wherein the $R^{1d'}$ substituents are independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —(C$_1$-C$_6$ alkyl)-O—(C$_1$-C$_6$ alkyl), —CN, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —S(=O)$_2$—(C$_1$-C$_6$ alkyl), —S(=O)$_2$NH$_2$, —S(=O)$_2$NH(C$_1$-C$_6$ alkyl), or —S(=O)$_2$N(C$_1$-C$_6$ alkyl)$_2$.

13. The compound of claim 1 or the pharmaceutically acceptable salt thereof, the tautomer thereof, the pharmaceutically acceptable salt of the tautomer, the stereoisomer of any of the foregoing, or the mixture thereof, wherein R$^1$ is R$^{1e}$.

14. The compound of claim 13 or the pharmaceutically acceptable salt thereof, the tautomer thereof, the pharmaceutically acceptable salt of the tautomer, the stereoisomer of any of the foregoing, or the mixture thereof, wherein R$^{1e}$ is an unsubstituted furanyl substituted with 1 or 2 R$^{1e'}$ substituents.

15. The compound of claim 1 or the pharmaceutically acceptable salt thereof, the tautomer thereof, the pharmaceutically acceptable salt of the tautomer, the stereoisomer of any of the foregoing, or the mixture thereof, wherein R$^1$ is R$^{1f}$.

16. The compound of claim 15 or the pharmaceutically acceptable salt thereof, the tautomer thereof, the pharmaceutically acceptable salt of the tautomer, the stereoisomer of any of the foregoing, or the mixture thereof, wherein R$^{1f}$ is selected from

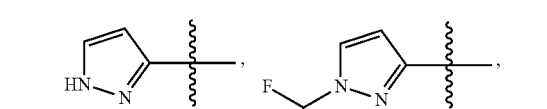

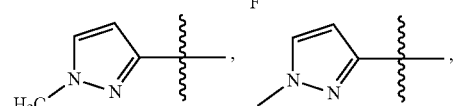

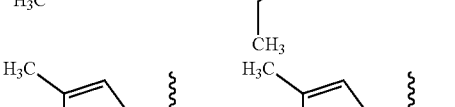

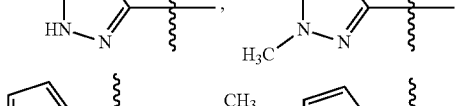

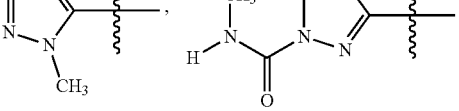

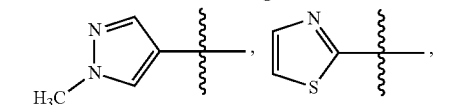

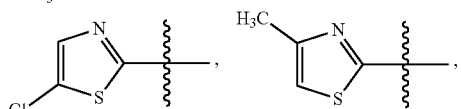

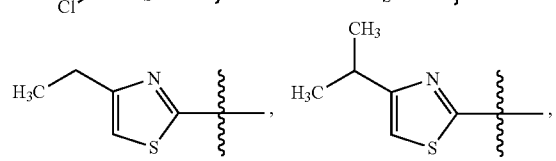

-continued

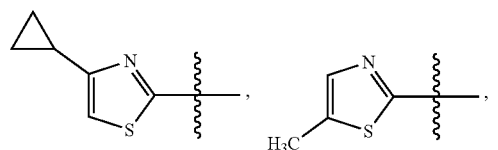

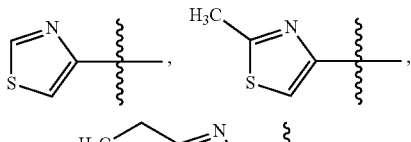

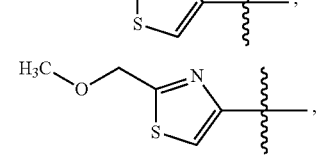

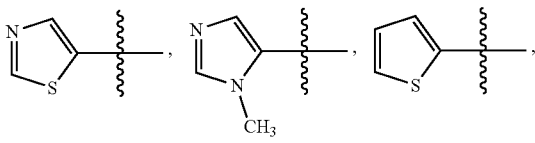

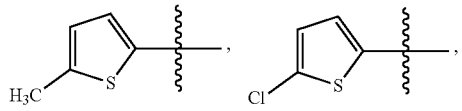

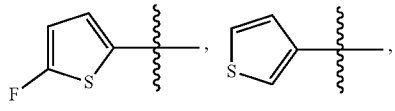

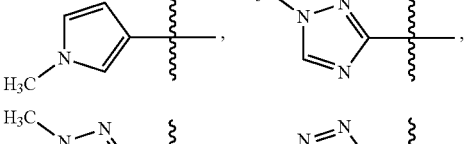

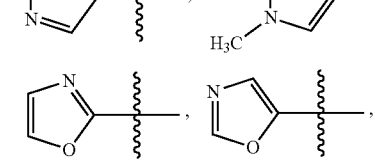

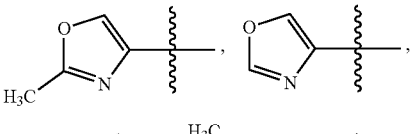

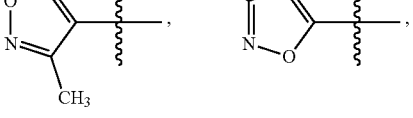

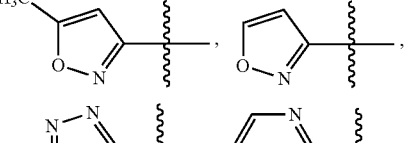

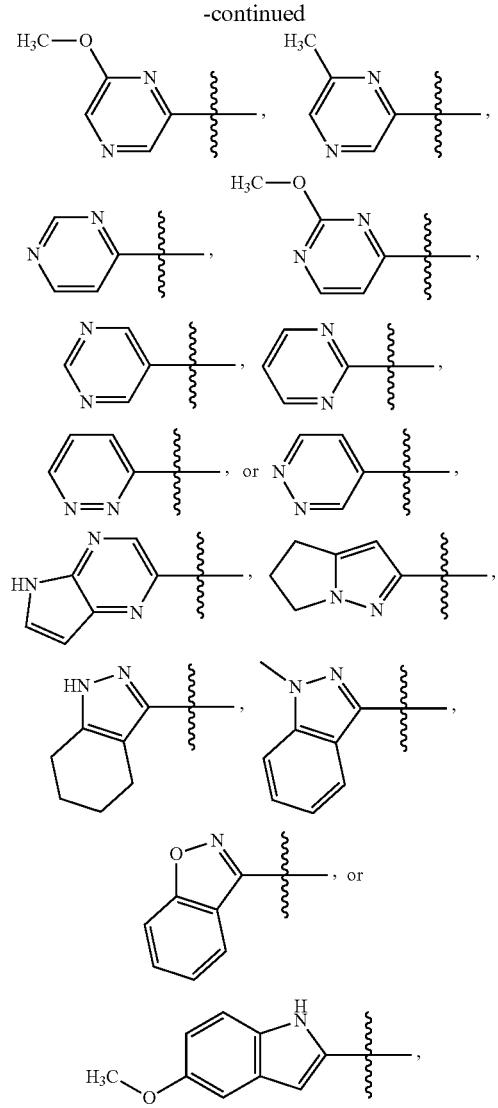

wherein the symbol ⌇⌇, when drawn across a bond, indicates the point of attachment to the rest of the molecule.

17. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is $R^{1g}$.

18. The compound of claim 17 or the pharmaceutically acceptable salt thereof, the tautomer thereof, the pharmaceutically acceptable salt of the tautomer, the stereoisomer of any of the foregoing, or the mixture thereof, wherein $R^{1g}$ is selected from

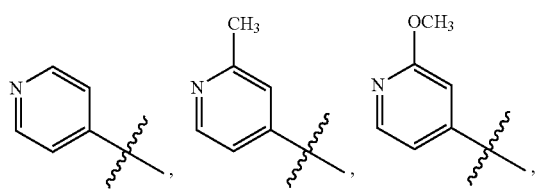

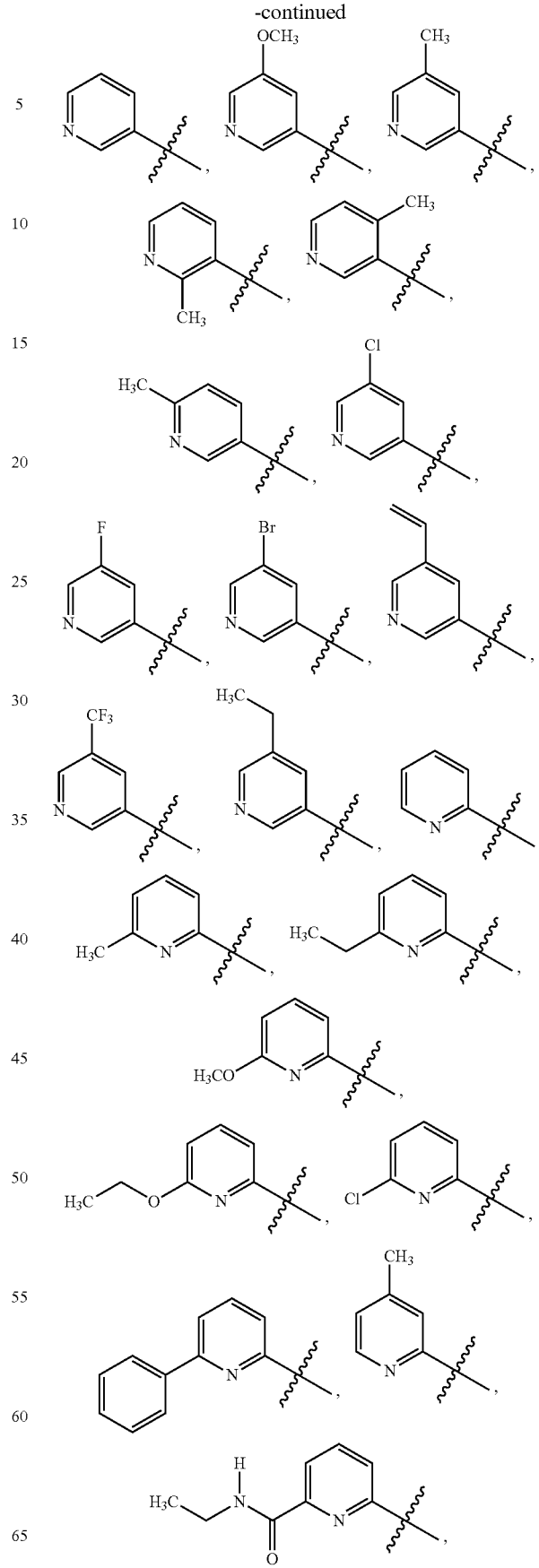

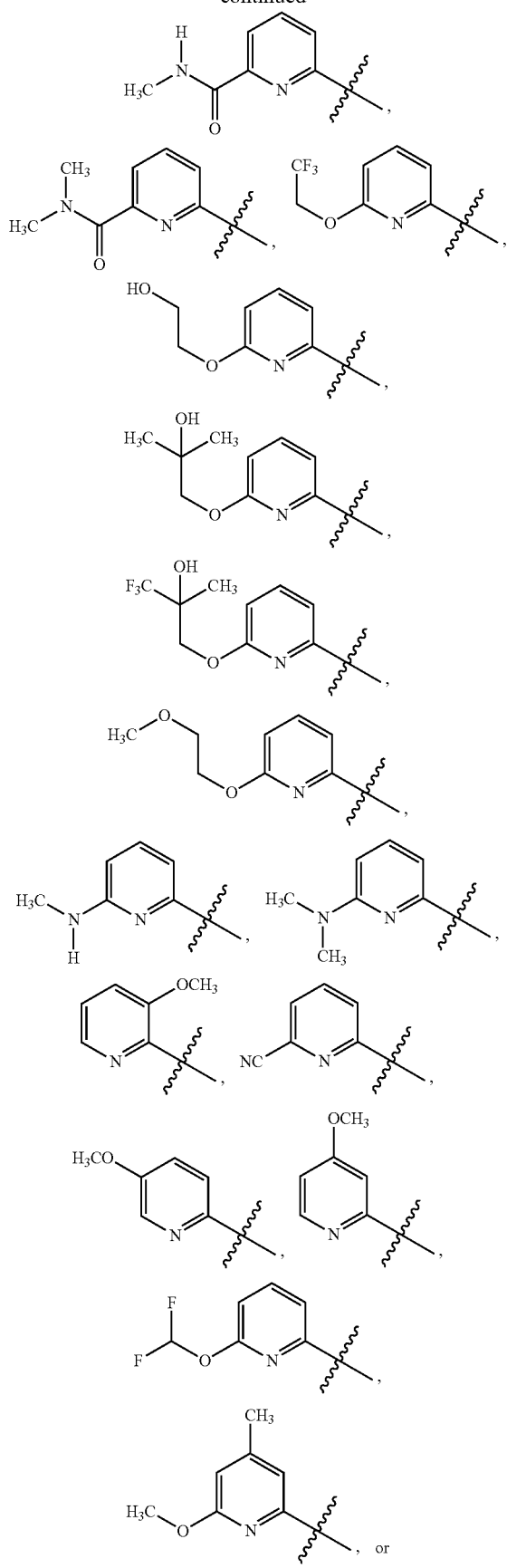

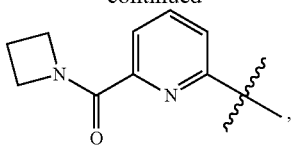

wherein the symbol ⌇, when drawn across a bond, indicates the point of attachment to the rest of the molecule.

19. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is an unsubstituted $C_1$-$C_{10}$ alkyl or is a $C_1$-$C_{10}$ alkyl substituted with 1, 2, or 3 $R^{3a}$ substituents.

20. The compound of claim 19 or the pharmaceutically acceptable salt thereof, the tautomer thereof, the pharmaceutically acceptable salt of the tautomer, the stereoisomer of any of the foregoing, or the mixture thereof, wherein $R^3$ is selected from —$CH_3$, —$CH_2CH_3$, —$CH_2CH_2CH_3$, —$CH_2CH_2CH_2CH_3$, or —$CH(CH_3)_2$.

21. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula a group of formula —$(CR^{3b}R^{3c})$-Q.

22. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q.

23. The compound of claim 22 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

24. The compound of claim 22 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, or —$C_1$-$C_6$ alkyl; and $R^{1f}$ and $R^{3g}$ are independently selected from —H, —$C_1$-$C_6$ alkyl, —OH, or —O—($C_1$-$C_6$ alkyl).

25. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from

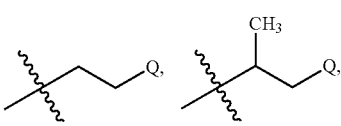

-continued

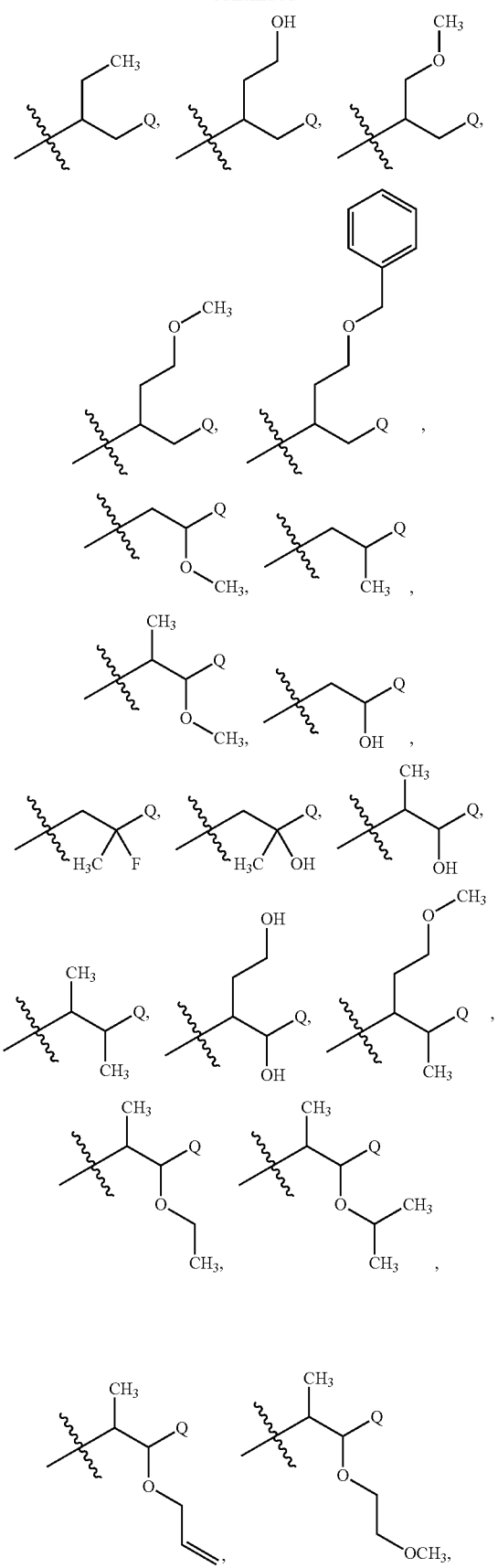

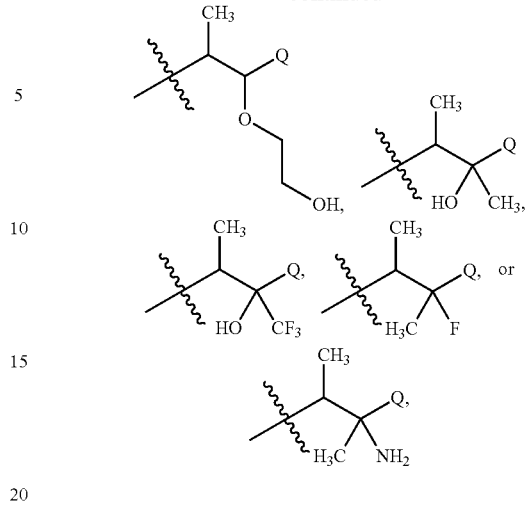

wherein the symbol ⌇, when drawn across a bond, indicates the point of attachment to the rest of the molecule.

26. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, phenyl, naphthalenyl, or cyclohexyl any of which may be unsubstituted or substituted with 1, 2, or 3 $R^Q$ substituents.

27. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), or —O—($C_1$-$C_6$ perhaloalkyl).

28. The compound of claim 1 the pharmaceutically acceptable salt thereof, the tautomer thereof, the pharmaceutically acceptable salt of the tautomer, the stereoisomer of any of the foregoing, or the mixture thereof, wherein Q is selected from

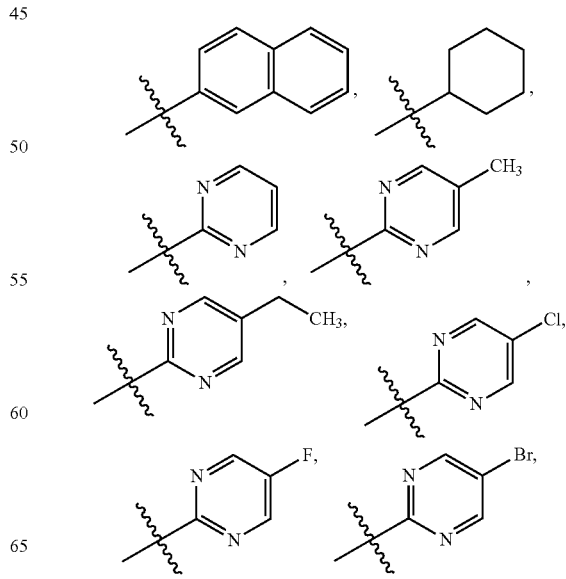

-continued

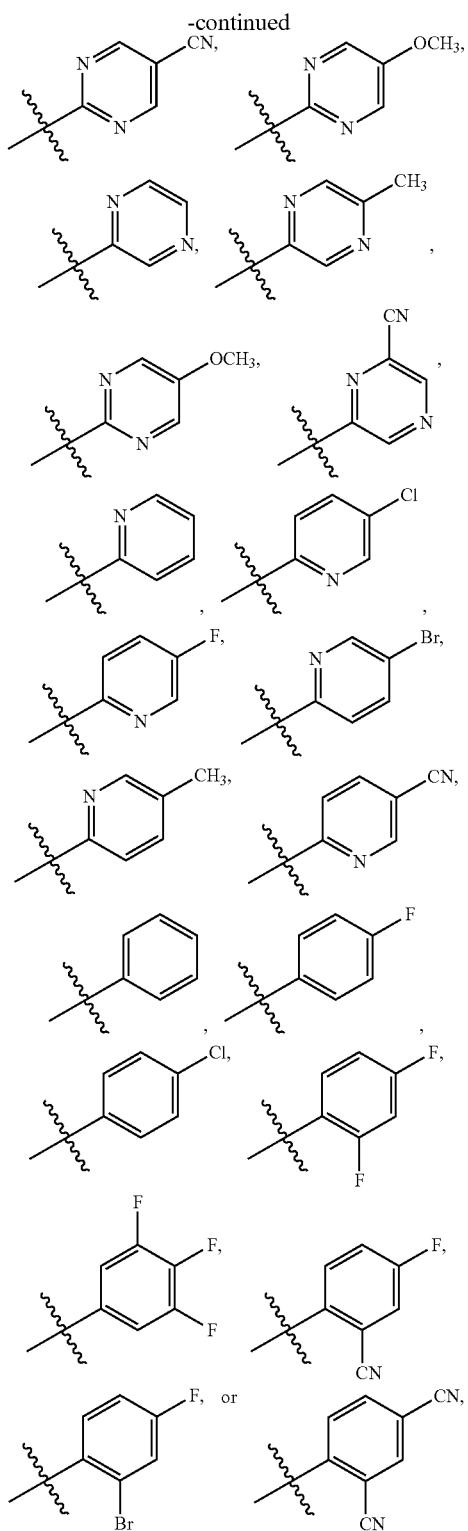

wherein the symbol ~~~, when drawn across a bond, indicates the point of attachment to the rest of the molecule.

29. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is —H.

30. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, or 3 $R^{4a}$ substituents.

31. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, —NH($C_1$-$C_6$ alkyl-OH), —C(=O)$NH_2$, —C(=O)NH($C_1$-$C_6$ alkyl), or —C(=O)N($C_1$-$C_6$ alkyl)$_2$.

32. The compound of claim 1 or the pharmaceutically acceptable salt thereof, the stereoisomer of any of the foregoing, or the mixture thereof, wherein $R^4$ is selected from

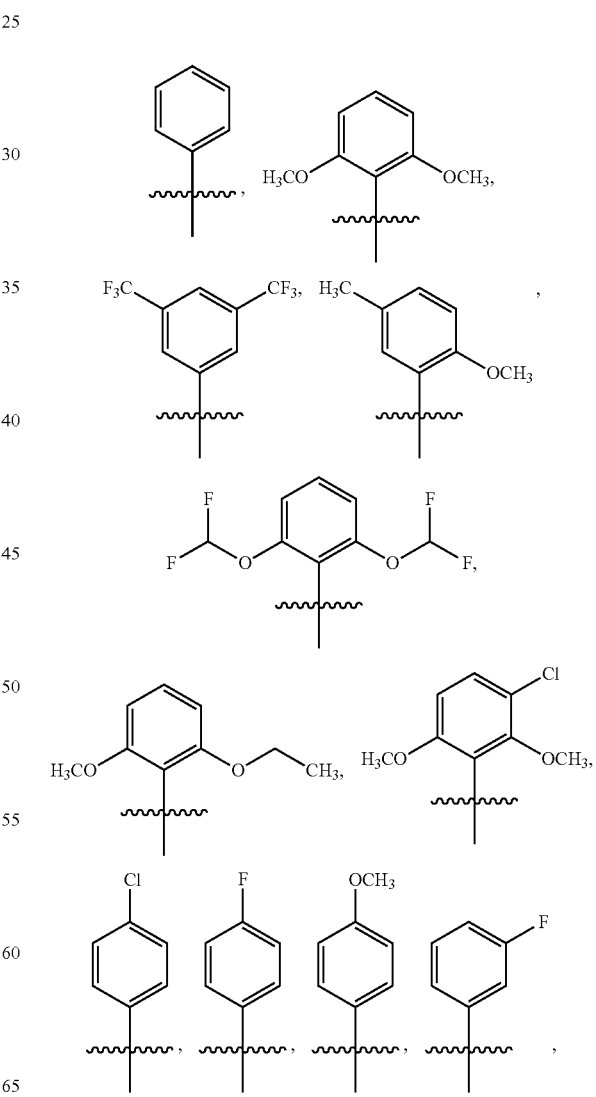

-continued
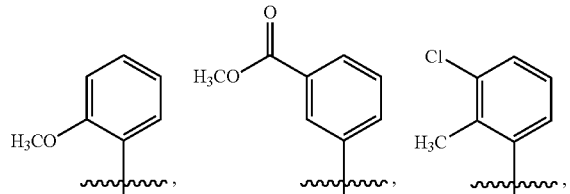
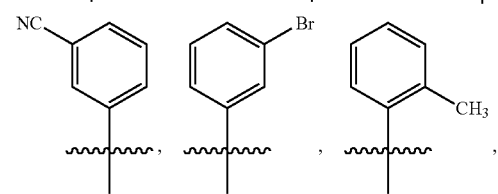
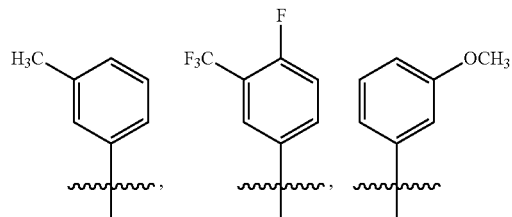
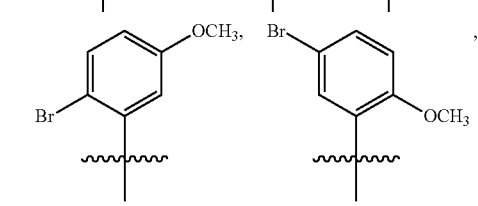
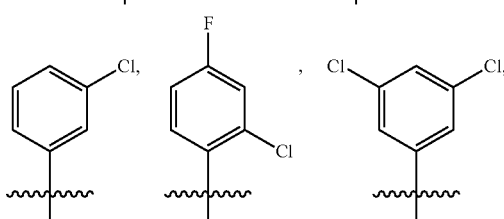
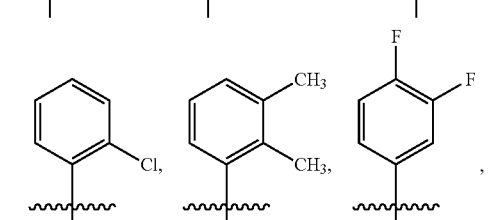
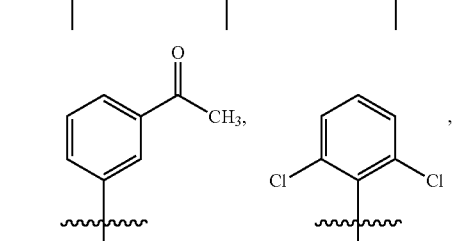
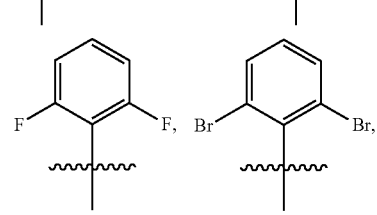
-continued
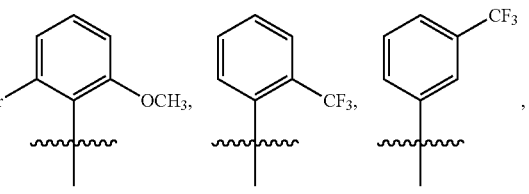
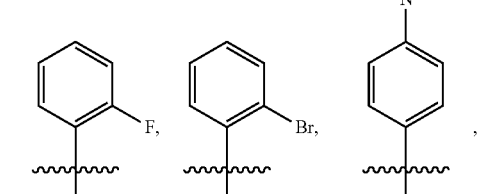
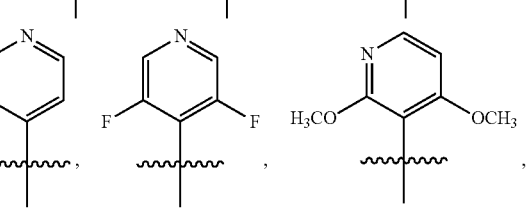
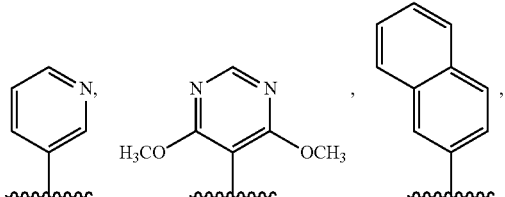
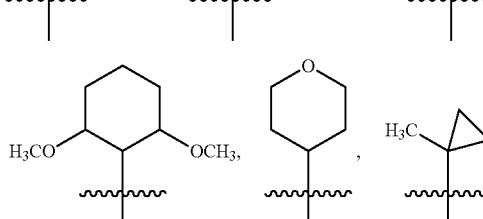
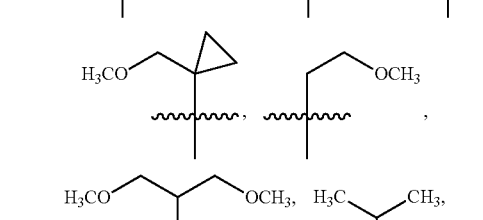
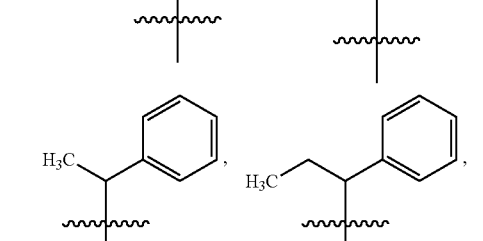
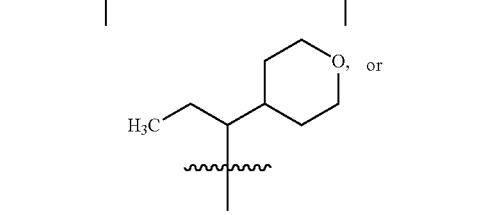

-continued
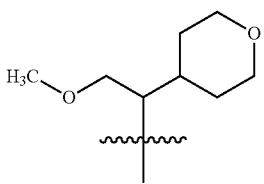
wherein the symbol ~~~, when drawn across a bond, indicates the point of attachment to the rest of the molecule.
33. The compound of claim 1, wherein the compound is selected from one of the following:
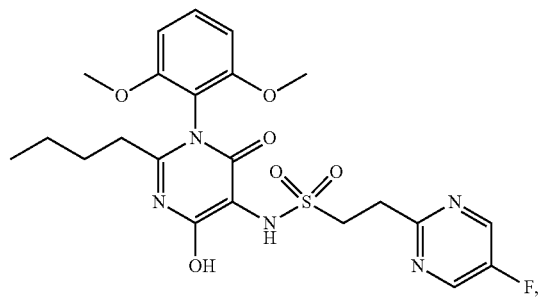
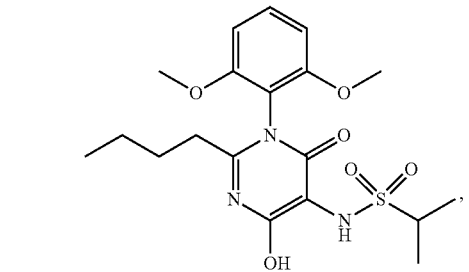
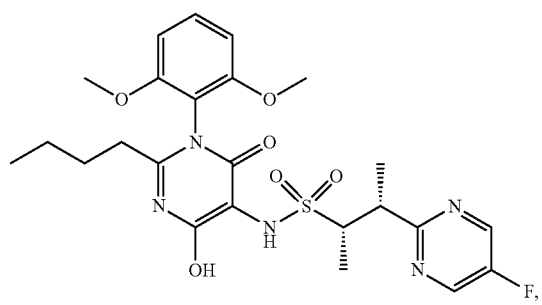
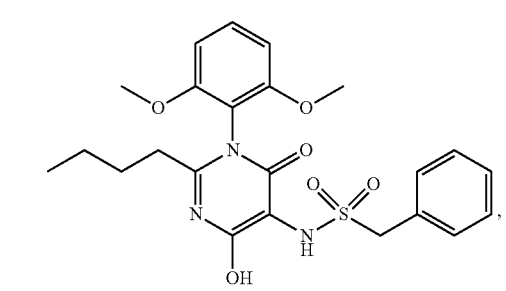
-continued
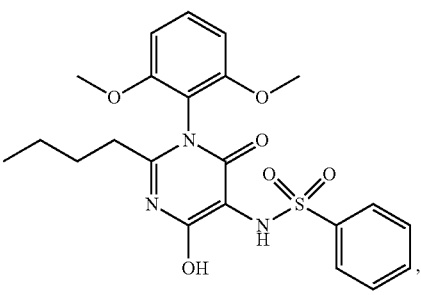
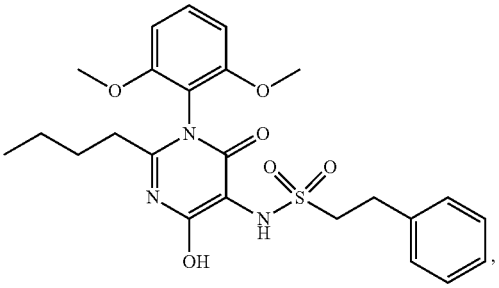
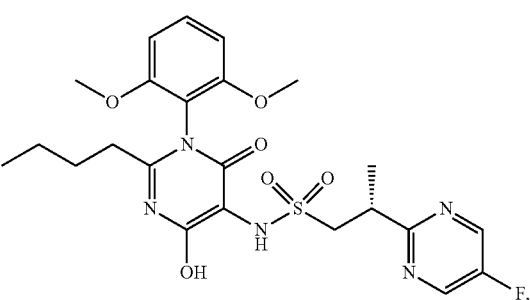
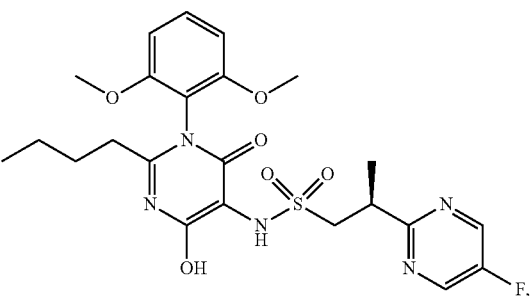
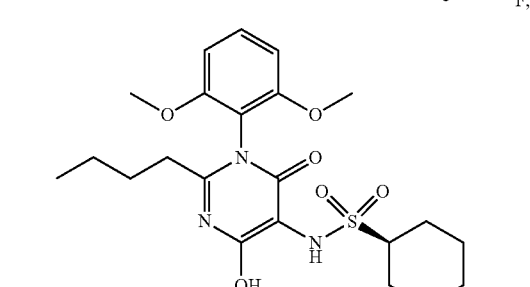
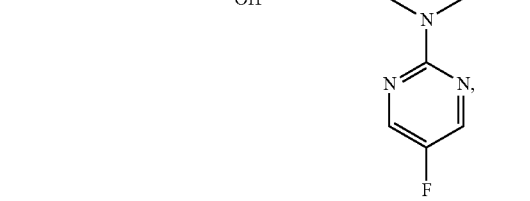

145
-continued
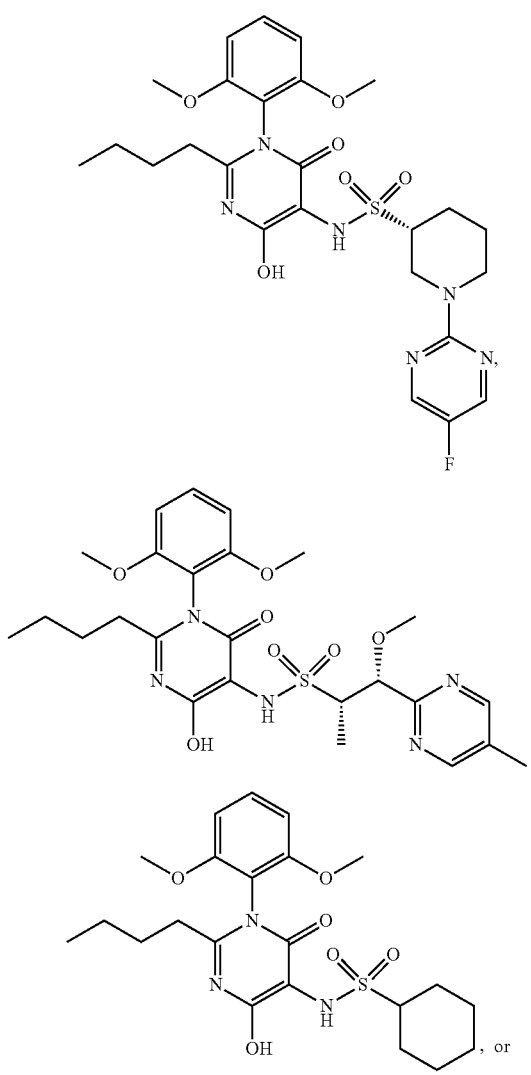
, or
the pharmaceutically acceptable salt thereof, or the mixture thereof.
34. The compound of claim 1, wherein the compound is selected from one of the following:
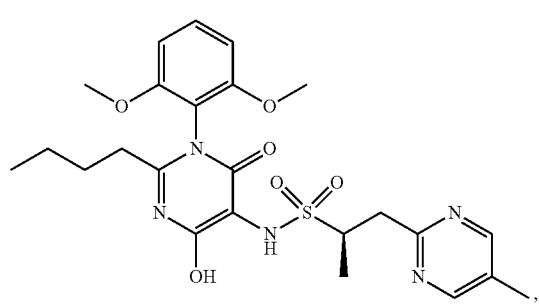
146
-continued
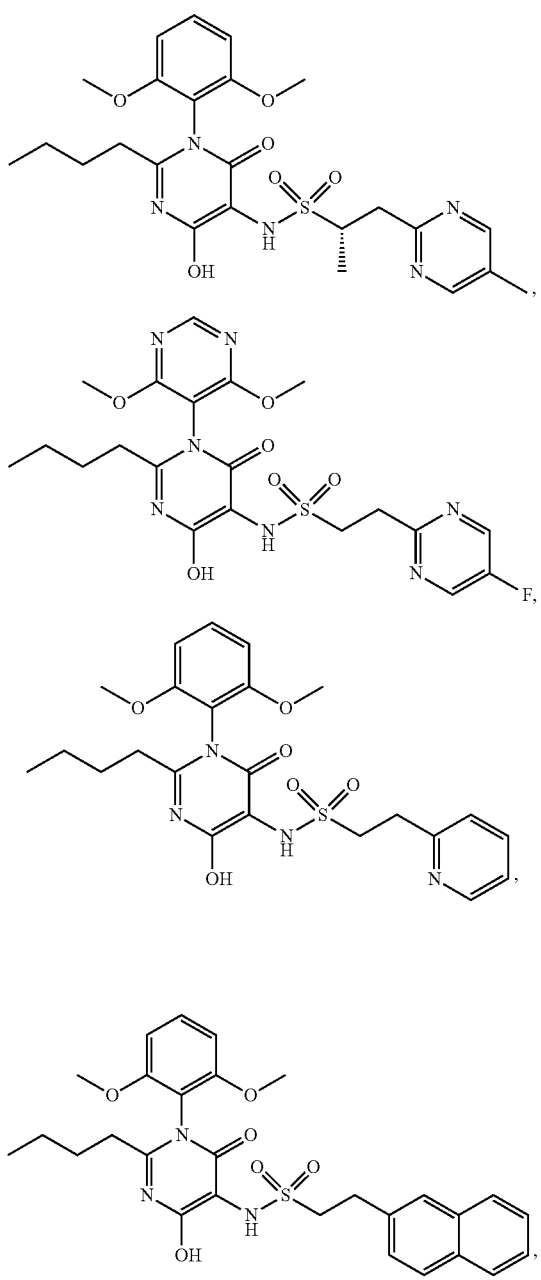
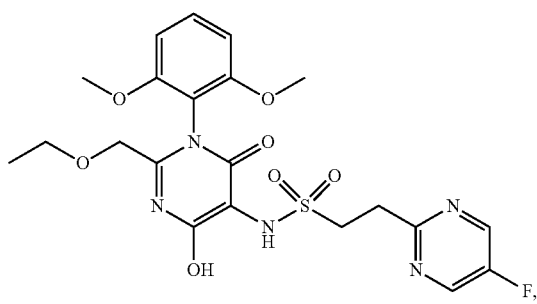

147
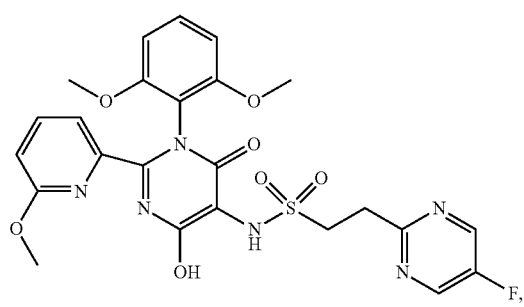
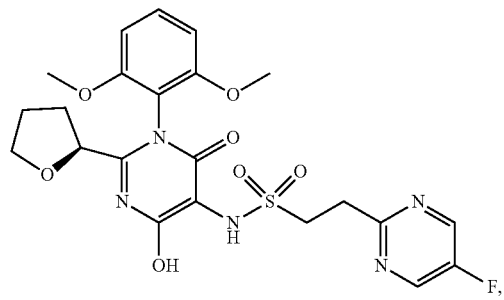
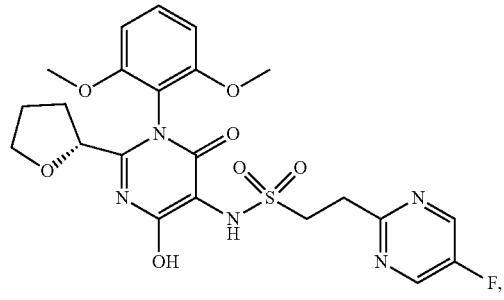
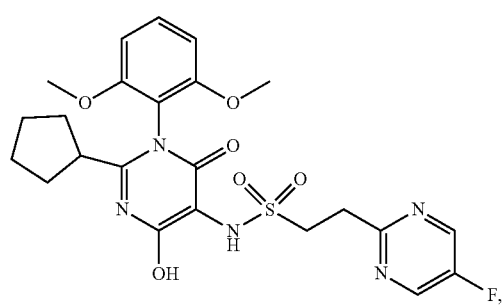
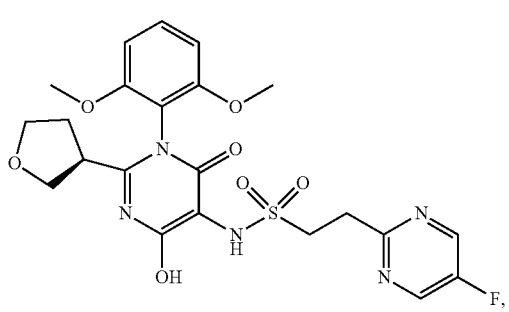
148
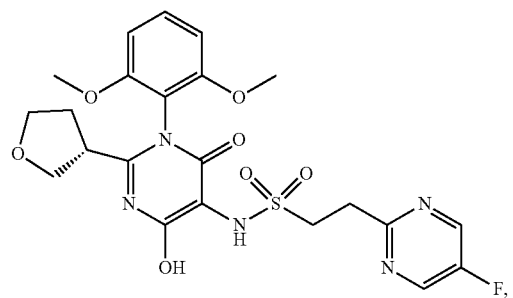
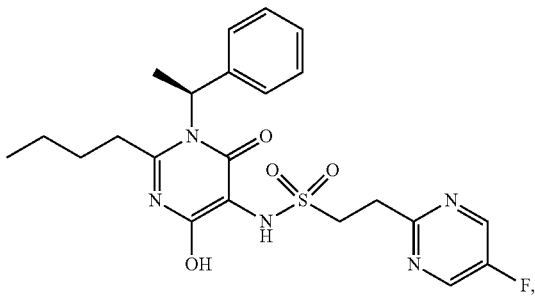
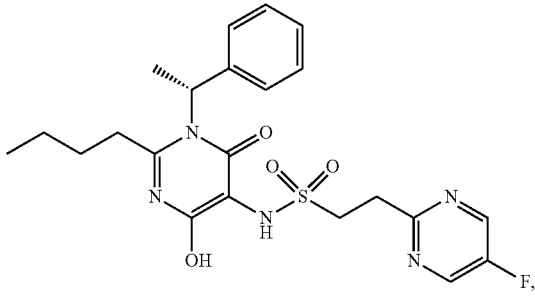
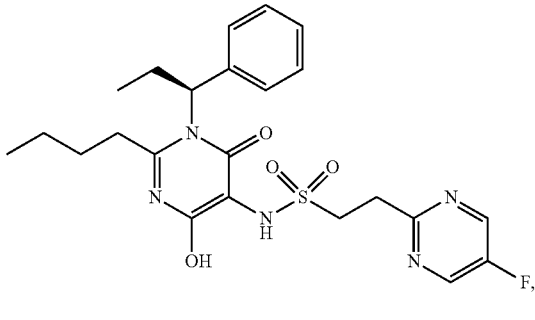
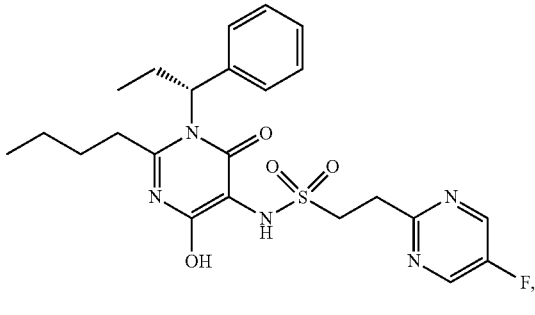

149
-continued
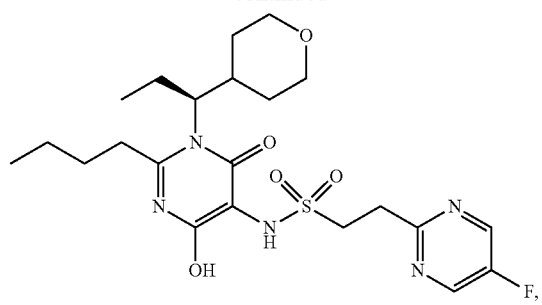
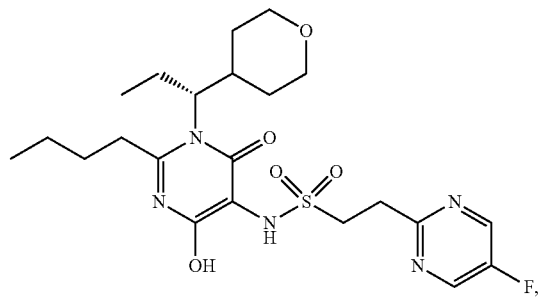
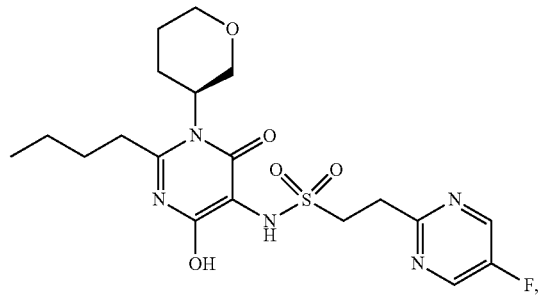
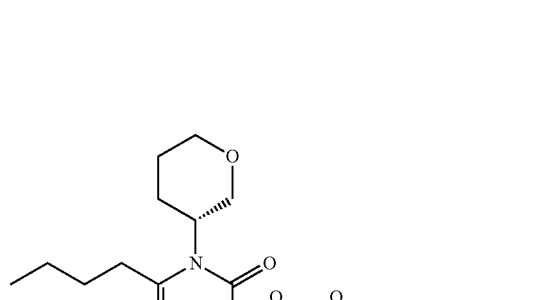
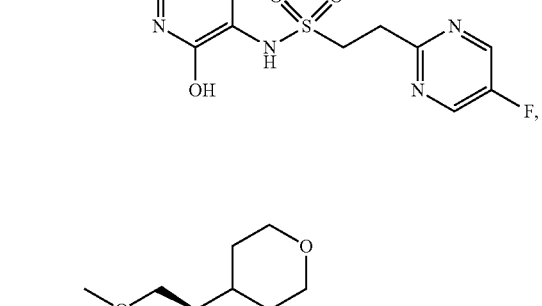
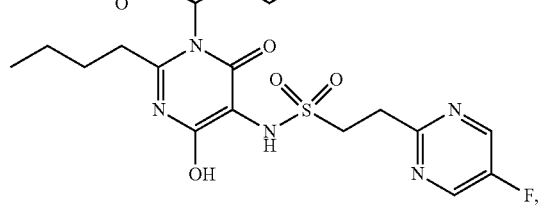
150
-continued
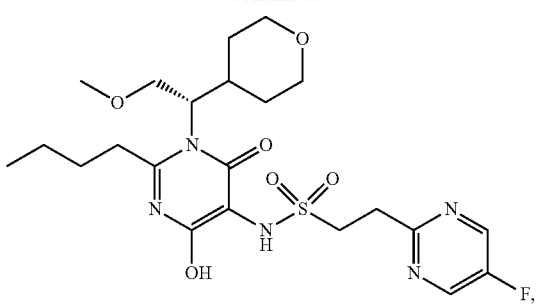
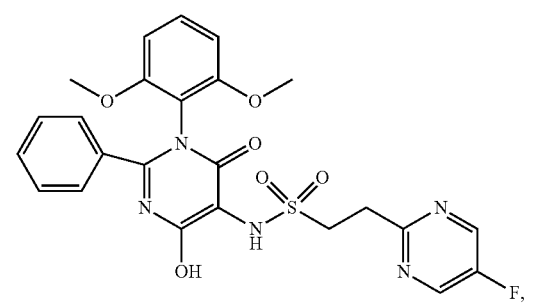
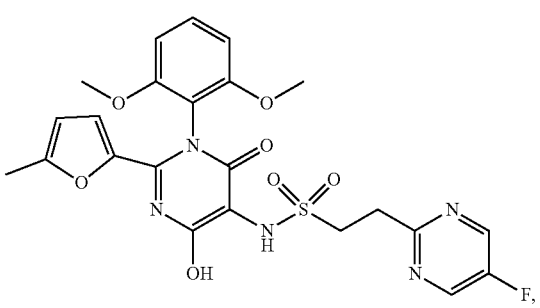
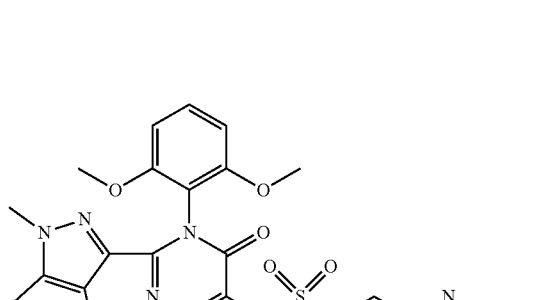
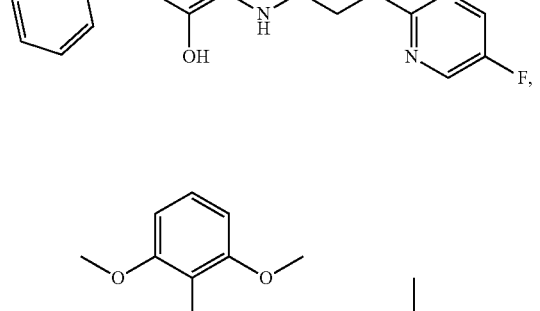
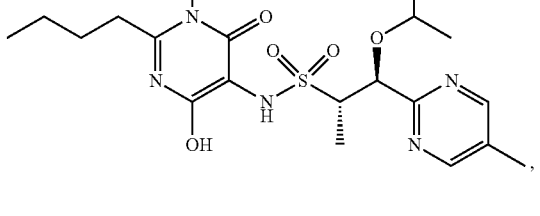

151
-continued

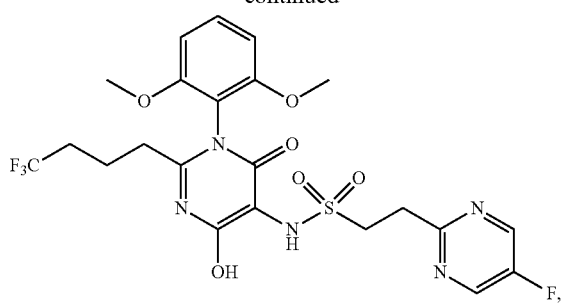

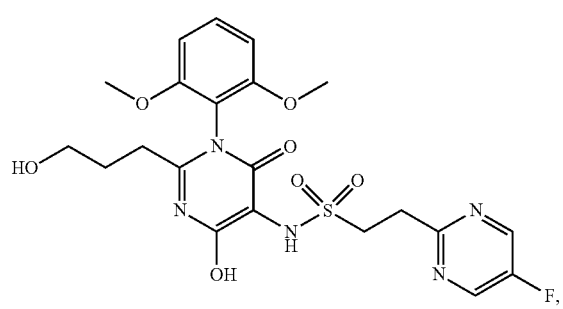

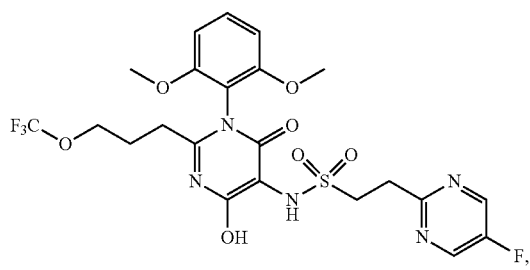

152
-continued

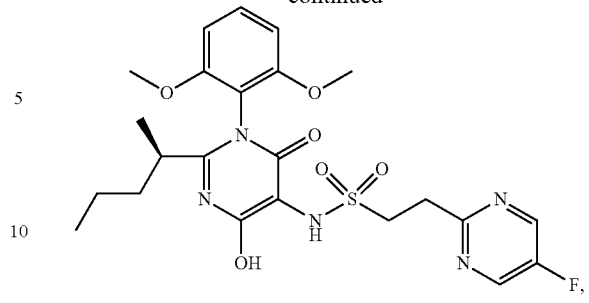

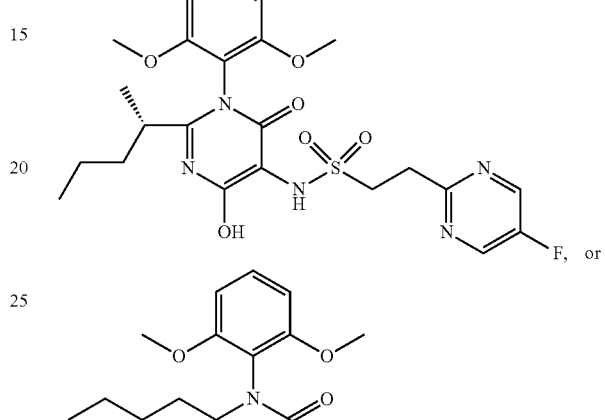

the pharmaceutically acceptable salt thereof, or the mixture thereof.

35. A pharmaceutical composition, comprising the compound of claim 1 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

* * * * *

UNITED STATES PATENT AND TRADEMARK OFFICE
CERTIFICATE OF CORRECTION

PATENT NO. : 11,807,624 B2
APPLICATION NO. : 17/051212
DATED : November 7, 2023
INVENTOR(S) : Vatee Pattaropong et al.

It is certified that error appears in the above-identified patent and that said Letters Patent is hereby corrected as shown below:

In the Claims

In Column 122, Claim 1, Line 38, delete "3 $R^{1f"}$" and insert -- 3 $R^{1f}$ --, therefor.

In Column 123, Claim 1, Line 32, delete "$R^{1a'"}$" and insert -- $R^{1a"}$ --, therefor.

In Column 123, Claim 1, Line 48, delete "perhaloalkyl)," and insert -- -O-($C_1$-$C_6$ perhaloalkyl), --, therefor.

In Column 123, Claim 1, Line 49, delete "perhaloalkyl, alkenyl," and insert -- -$C_1$-$C_6$ perhaloalkyl, -$C_2$-$C_4$ alkenyl, --, therefor.

In Column 123, Claim 1, Line 51, delete "alkyl)" and insert -- -($C_1$-$C_6$ alkyl), --, therefor.

In Column 123, Claim 1, Line 52, delete "haloalkyl)" and insert -- -($C_1$-$C_6$ haloalkyl) --, therefor.

In Column 123, Claim 1, Line 53, delete "perhaloalkyl)" and insert -- -($C_1$-$C_6$ perhaloalkyl) --, therefor.

In Column 123, Claim 1, Line 54, delete "alkyl)" and insert -- -O-($C_1$-$C_6$ alkyl) --, therefor.

In Column 123, Claim 1, Line 55, delete "$C_6$ haloalkyl)" and insert -- -O-($C_1$-$C_6$ haloalkyl) --, therefor.

In Column 123, Claim 1, Line 56, delete "perhaloalkyl)" and insert -- -O-($C_1$-$C_6$ perhaloalkyl) --, therefor.

In Column 124, Claim 1, Line 8, delete "perhaloalkyl)," and insert -- -O-($C_1$-$C_6$ perhaloalkyl), --, therefor.

In Column 124, Claim 1, Line 9, delete "perhaloalkyl, alkenyl," and insert -- -$C_1$-$C_6$ perhaloalkyl, Signed and Sealed this
Thirtieth Day of July, 2024

*Katherine Kelly Vidal*
*Director of the United States Patent and Trademark Office*

CERTIFICATE OF CORRECTION (continued)
U.S. Pat. No. 11,807,624 B2

-$C_2$-$C_4$ alkenyl, --, therefor.

In Column 124, Claim 1, Line 9, delete "alkyl)" and insert -- -($C_1$-$C_6$ alkyl) --, therefor.

In Column 124, Claim 1, Line 10, delete "alkyl)" and insert -- -($C_1$-$C_6$ alkyl) --, therefor.

In Column 124, Claim 1, Line 11, delete "haloalkyl)" and insert -- -($C_1$-$C_6$ haloalkyl) --, therefor.

In Column 124, Claim 1, Line 12, delete "perhaloalkyl)" and insert -- -($C_1$-$C_6$ perhaloalkyl) --, therefor.

In Column 124, Claim 1, Line 14, delete "haloalkyl)" and insert -- -O-($C_1$-$C_6$ haloalkyl) --, therefor.

In Column 124, Claim 1, Line 15, delete "perhaloalkyl)-" and insert -- -O-($C_1$-$C_6$ perhaloalkyl)- --, therefor.

In Column 124, Claim 1, Line 25, delete "perhaloalkyl," and insert -- -$C_1$-$C_6$ perhaloalkyl, --, therefor.

In Column 124, Claim 1, Line 25, delete "alkyl)" and insert -- ($C_1$-$C_6$ alkyl) --, therefor.

In Column 124, Claim 1, Lines 26-27, delete "perhaloalkyl," and insert -- -O-($C_1$-$C_6$ perhaloalkyl), --, therefor.

In Column 124, Claim 1, Line 27, delete "alkenyl, alkyl)" and insert -- -$C_2$-$C_6$ alkenyl, -O-($C_1$-$C_6$ alkyl) --, therefor.

In Column 124, Claim 1, Line 27, delete "alkyl)" and insert -- -O-($C_1$-$C_6$ alkyl) --, therefor.

In Column 124, Claim 1, Line 28, delete "haloalkyl)" and insert -- -O-($C_1$-$C_6$ haloalkyl) --, therefor.

In Column 124, Claim 1, Line 29, delete "perhaloalkyl)-" and insert -- -O-($C_1$-$C_6$ perhaloalkyl)- --, therefor.

In Column 124, Claim 1, Line 57, delete "alkyl)" and insert -- ($C_1$-$C_6$ alkyl) --, therefor.

In Column 124, Claim 1, Line 59, delete "perhaloalkyl)," and insert -- -O-($C_1$-$C_6$ perhaloalkyl), --, therefor.

In Column 124, Claim 1, Line 60, delete "alkyl)" and insert -- -O-($C_1$-$C_6$ alkyl) --, therefor.

In Column 124, Claim 1, Line 63, delete "perhaloalkyl)" and insert -- -O-($C_1$-$C_6$ perhaloalkyl) --, therefor.

In Column 125, Claim 1, Line 1, delete "$R_{1d'}$" and insert -- $R^{1d'}$ --, therefor.

CERTIFICATE OF CORRECTION (continued)
U.S. Pat. No. 11,807,624 B2

In Column 125, Claim 1, Line 3, delete "alkyl)" and insert -- -($C_1$-$C_6$ alkyl) --, therefor.

In Column 125, Claim 1, Line 3, delete "haloalkyl)" and insert -- -($C_1$-$C_6$ haloalkyl) --, therefor.

In Column 125, Claim 1, Lines 3-4, delete "perhaloalkyl)," and insert -- ($C_1$-$C_6$ perhaloalkyl), --, therefor.

In Column 125, Claim 1, Line 4, delete "alkyl)" and insert -- -($C_1$-$C_6$ alkyl) --, therefor.

In Column 125, Claim 1, Lines 5-6, delete "perhaloalkyl)," and insert -- -O-($C_1$-$C_6$ perhaloalkyl), --, therefor.

In Column 125, Claim 1, Line 6, delete "alkyl)" and insert -- -O-($C_1$-$C_6$ alkyl) --, therefor.

In Column 125, Claim 1, Line 11, delete "-Q=O)" and insert -- -C(=O) --, therefor.

In Column 125, Claim 1, Line 28, delete "alkyl)" and insert -- -($C_1$-$C_6$ alkyl) --, therefor.

In Column 125, Claim 1, Line 33, delete "haloalkyl)" and insert -- -O-($C_1$-$C_6$ haloalkyl) --, therefor.

In Column 126, Claim 1, Line 1, delete "$R^{1f}$" and insert -- $R^{1f}$ --, therefor.

In Column 126, Claim 1, Line 16, delete "$R^{1f}$" and insert -- $R^{1f}$ --, therefor.

In Column 126, Claim 1, Line 24, delete "2 $R^{1f}$" and insert -- 2 $R^{1f}$ --, therefor.

In Column 126, Claim 1, Line 27, delete "$R^{1f}$" and insert -- $R^{1f}$ --, therefor.

In Column 126, Claim 1, Line 41, delete "$R^{1f}$" and insert -- $R^{1f}$ --, therefor.

In Column 127, Claim 1, Line 41, delete "$R^{3g}$" and insert -- $R^{3e}$ --, therefor.

In Column 128, Claim 1, Line 57, delete "alkyl)" and insert -- -($C_1$-$C_6$ alkyl) --, therefor.

In Column 128, Claim 1, Line 58, delete "haloalkyl)," and insert -- -O-($C_1$-$C_6$ haloalkyl), --, therefor.

In Column 128, Claim 1, Lines 58-59, delete "perhaloalkyl)," and insert -- -O-($C_1$-$C_6$ perhaloalkyl), --, therefor.

In Column 129, Claim 1, Line 7, delete "perhaloalkyl)." and insert -- -O-($C_1$-$C_6$ perhaloalkyl), --, therefor.

In Column 129, Claim 1, Line 8, delete "perhaloalkyl)," and insert -- -S-($C_1$-$C_6$ perhaloalkyl), --, therefor.

In Column 136, Claim 24, Line 54, delete "$R^{1f}$" and insert -- $R^{3f}$ --, therefor.